US011369569B2

(12) United States Patent
Klibanov et al.

(10) Patent No.: US 11,369,569 B2
(45) Date of Patent: Jun. 28, 2022

(54) TARGET-SPECIFIC DELIVERY OF THERAPEUTIC AGENTS

(71) Applicant: University of Virginia Patent Foundation, Charlottesville, VA (US)

(72) Inventors: Alexander L. Klibanov, Charlottesville, VA (US); Brent A. French, Charlottesville, VA (US); Kimberly A. Kelly, Crozet, VA (US); Siva Sai Krishna Dasa, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/737,047

(22) PCT Filed: Jun. 15, 2016

(86) PCT No.: PCT/US2016/037668
§ 371 (c)(1),
(2) Date: Dec. 15, 2017

(87) PCT Pub. No.: WO2016/205397
PCT Pub. Date: Dec. 22, 2016

(65) Prior Publication Data
US 2018/0360755 A1 Dec. 20, 2018

Related U.S. Application Data

(60) Provisional application No. 62/175,922, filed on Jun. 15, 2015.

(51) Int. Cl.
| A61K 47/64 | (2017.01) |
| A61K 47/69 | (2017.01) |
| A61K 9/127 | (2006.01) |
| A61K 9/00 | (2006.01) |
| A61K 47/62 | (2017.01) |
| C07K 7/06 | (2006.01) |
| A61P 9/00 | (2006.01) |

(52) U.S. Cl.
CPC ............ *A61K 9/127* (2013.01); *A61K 9/0019* (2013.01); *A61K 47/62* (2017.08); *A61K 47/64* (2017.08); *A61K 47/6911* (2017.08); *A61K 47/6913* (2017.08); *A61P 9/00* (2018.01); *C07K 7/06* (2013.01)

(58) Field of Classification Search
CPC ..... A61K 38/08; A61K 47/64; A61K 47/6911
See application file for complete search history.

(56) References Cited

U.S. PATENT DOCUMENTS

| 6,303,573 | B1 * | 10/2001 | Ruoslahti | ............... | A61K 47/62 |
| | | | | | 424/185.1 |
| 8,178,110 | B2 * | 5/2012 | Sellers | .................. | A61P 37/04 |
| | | | | | 424/215.1 |
| 8,344,211 | B2 * | 1/2013 | Alexandrov | ........... | A23K 10/30 |
| | | | | | 435/320.1 |
| 10,463,711 | B2 * | 11/2019 | Hamill | ..................... | A61P 31/14 |
| 2003/0181692 | A1 * | 9/2003 | Ni | .......................... | C07K 14/47 |
| | | | | | 536/23.1 |
| 2004/0098767 | A1 * | 5/2004 | Spangenberg | ..... | C12N 15/8214 |
| | | | | | 800/320 |
| 2005/0084491 | A1 * | 4/2005 | Shealy | ..................... | C07K 7/06 |
| | | | | | 424/144.1 |
| 2005/0176097 | A1 * | 8/2005 | Andersen | ....... | C12Y 302/01001 |
| | | | | | 435/69.1 |
| 2007/0044171 | A1 * | 2/2007 | Kovalic | .................. | A01G 22/00 |
| | | | | | 800/278 |
| 2007/0083334 | A1 * | 4/2007 | Mintz | .................... | G16B 40/00 |
| | | | | | 702/19 |
| 2011/0021748 | A1 | 1/2011 | Cunningham et al. | | |
| 2013/0116215 | A1 * | 5/2013 | Coma | .................... | A61K 31/51 |
| | | | | | 514/108 |
| 2014/0107062 | A1 * | 4/2014 | Shenoy | ................ | A61K 31/513 |
| | | | | | 514/50 |
| 2014/0343148 | A1 * | 11/2014 | Kohsaka | .................. | A61P 21/00 |
| | | | | | 514/561 |
| 2016/0272987 | A1 * | 9/2016 | Gil | ...................... | C12N 15/8273 |

FOREIGN PATENT DOCUMENTS

| WO | WO-9937770 A1 * | 7/1999 | ......... A01K 67/0275 |
| WO | WO-0155339 A2 * | 8/2001 | ............. C07K 14/47 |
| WO | WO-02098465 A2 | 12/2002 | |
| WO | WO-2009008727 A2 | 1/2009 | |
| WO | WO-2015006874 A1 | 1/2015 | |
| WO | WO-2016205397 A2 | 12/2016 | |
| WO | WO-2016205397 A3 | 12/2016 | |

OTHER PUBLICATIONS

Wittman et al. The endolysins of bacteriophages CMP1 and CN77 are specific for the lysis of Clavibacter michiganensis strains. Microbiology. 2010, vol. 156, pp. 2366-2373. (Year: 2010).*

"International Application Serial No. PCT/US2016/037668, International Search Report dated Feb. 16, 2017", 9 pgs.

"International Application Serial No. PCT/US2016/037668, Invitation to Pay Add'l Fees and Partial Search Rpt dated Dec. 20, 2016", 6 pgs.

"International Application Serial No. PCT/US2016/037668, Written Opinion dated Feb. 16, 2017", 10 pgs.

Anwer, K, et al., "Peptide-mediated gene transfer of cationic lipid/plasmid DNA complexes to endothelial cells", Journal of Drug Targeting, vol. 12, No. 4, XP009141015, ISSN: 1061-186X, (May 1, 2004), 215-221.

(Continued)

*Primary Examiner* — Jeffrey E. Russel
(74) *Attorney, Agent, or Firm* — Schwegman Lundberg & Woessner, P.A.

(57) ABSTRACT

Isolated peptides targeting cardiovascular disease are described herein or one or more conservative amino acid substitutions, deletions or additions of such peptides and methods of use thereof for delivering payloads to specific cell types or tissues.

19 Claims, 46 Drawing Sheets

Specification includes a Sequence Listing.

(56) References Cited

OTHER PUBLICATIONS

Dasa, Siva Sai Krishna, et al., "Development of target-specific liposomes for delivering small molecule drugs after reperfused myocardial infarction", Journal of Controlled Release, vol. 220, XP029341088, ISSN: 0168-3659, (Jun. 27, 2015), 556-567.

Longmuir, K J, et al., "Liposomal delivery of doxorubicin to hepatocytes in vivo by targeting heparan sulfate", International Journal of Pharmaceutics, Elsevier, Amsterdam, NL, vol. 382, No. 1-2, XP026708563, ISSN: 0378-5173,, (Dec. 1, 2009), 222-223.

\* cited by examiner

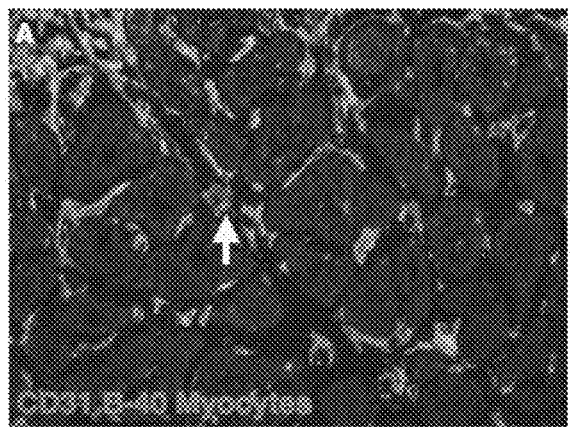
FIG. 2A
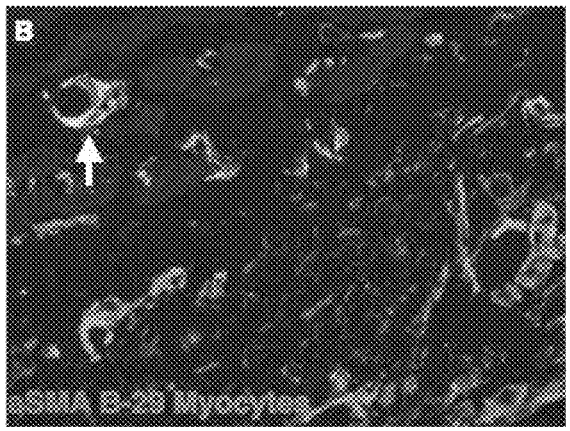
FIG. 2B
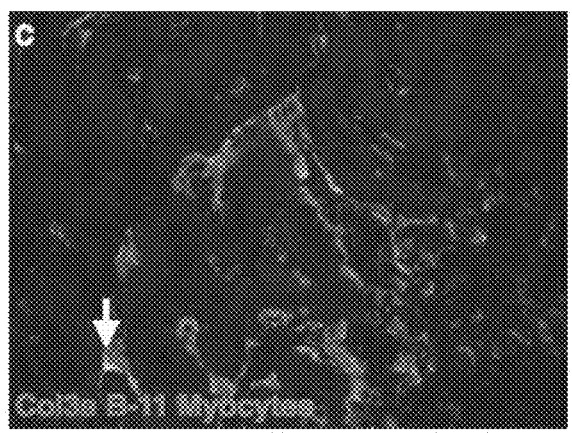
FIG. 2C
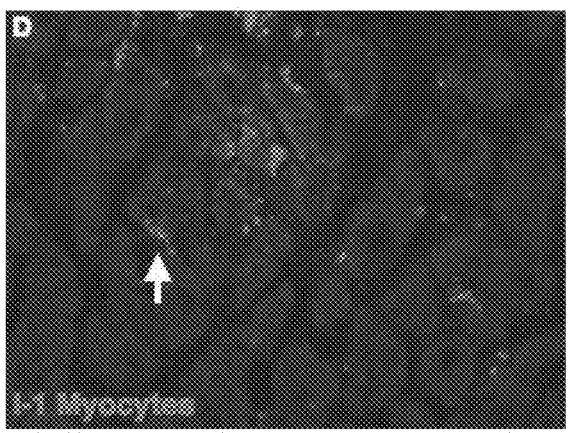
FIG. 2D
FIG. 2E
| CELL TYPE | IDENTIFYING MARKER | PHAGE CLONES |
|---|---|---|
| ENDOTHELIAL CELLS | CD 31 | B-40, B-47 |
| MYOCYTES | MYOGLOBIN | I-1, B-42 |
| MYOFIBROBLASTS | aSMA | B-29, B-7 |
| c-KIT + CPCs | c-KIT | B-50, B-27 |
| EXTRACELLULAR MATRIX | COLLAGEN 3a | B-11, B-43 |
FIG. 2F

| LIPOSOME COMPONENTS | RATIO | WEIGHT (mg) |
| --- | --- | --- |
| DOPC | 46 | 9.5 |
| CHOLESTEROL | 46 | 4.5 |
| DSPE-PEG-2k | 6 | 4.5 |
| PEPTIDE-PEG(3.4k)- | 1 | 1 |
| DiR | 1 | 0.5 |

| | $t_{1/2\lambda,1+2}$ | AUC |
| --- | --- | --- |
| NCP | 8.5+19.8 | 1549 |
| I-1 | 20.3+26.6 | 3098 |
| B-40 | 18.2+20.4 | 2310 |
| B-50 | 8.6+21.6 | 1555 |
| B-29 | 7.3+16.9 | 1890 |

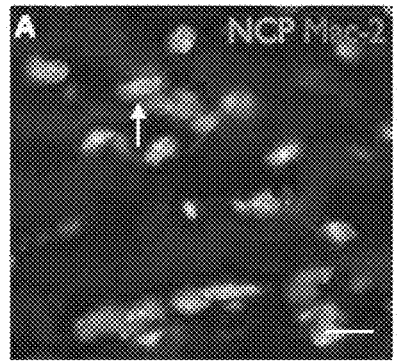
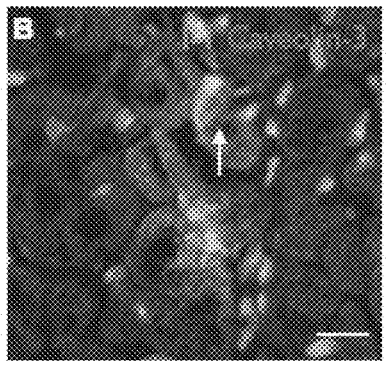
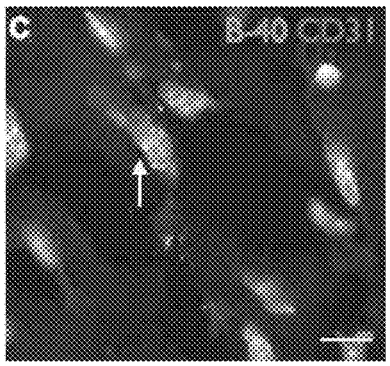
FIG. 4A  FIG. 4B  FIG. 4C
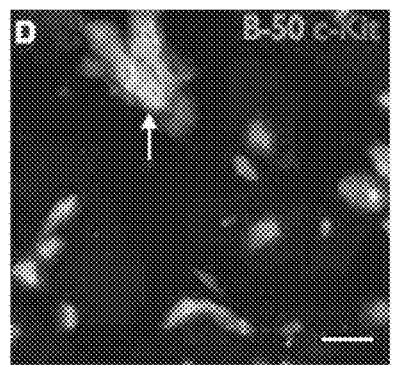
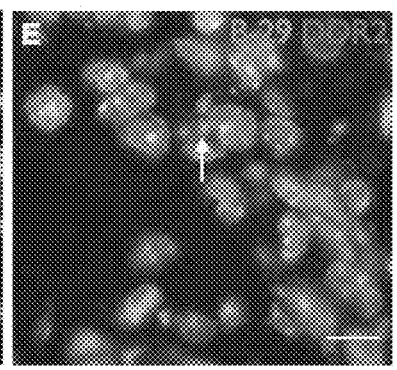
FIG. 4D  FIG. 4E
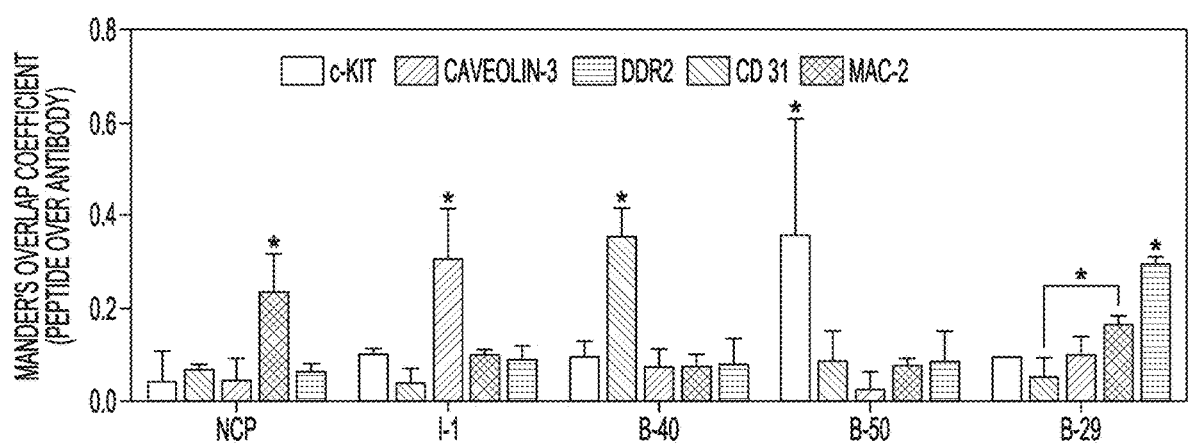
FIG. 4F

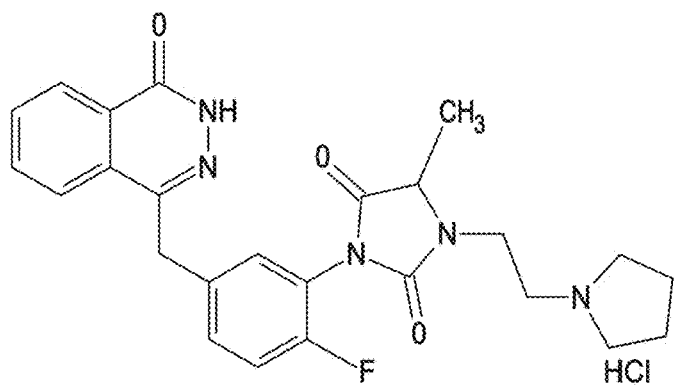
FIG. 5A
| PROPERTIES | AZ7379 |
|---|---|
| pKA | 11.5a, 8.7a, 8.94c |
| POLAR SURFACE AREA $A^2$ | 85.32b |
| TOTAL AREA $A^2$ | 667.06b |
| NON-POLAR AREA $A^2$ | 587.74b |
| NON-POLAR/POLAR | 6.818b |
| SOLUBILITY (mM) [pH] | 2.5[7.4]c |
| CHARGE [pH] | 1.02 [5,6,7,7.4]b |
| pI | 9.72b |
| LOG P | 1.89a, 2.75a |
| LOG D AT pH 7 | 1.05a |
FIG. 5B
| | NCP LIPOSOMES WITH AZ7379 | I-1 LIPOSOMES WITH AZ7379 |
|---|---|---|
| SIZE | 129 | 143 |
| CONCENTRATION (PER mL) | $1 \times 10^{12}$ | $8.54 \times 10^{11}$ |
| PEPTIDES/LIPOSOMES | 1130 | 1200 |
| DRUG/LIPOSOME | 279120 | 280000 |
FIG. 5C
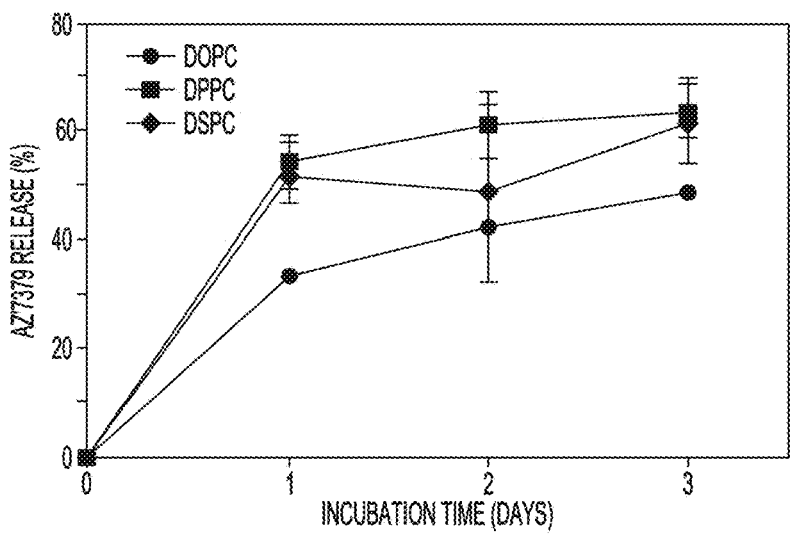
FIG. 5D

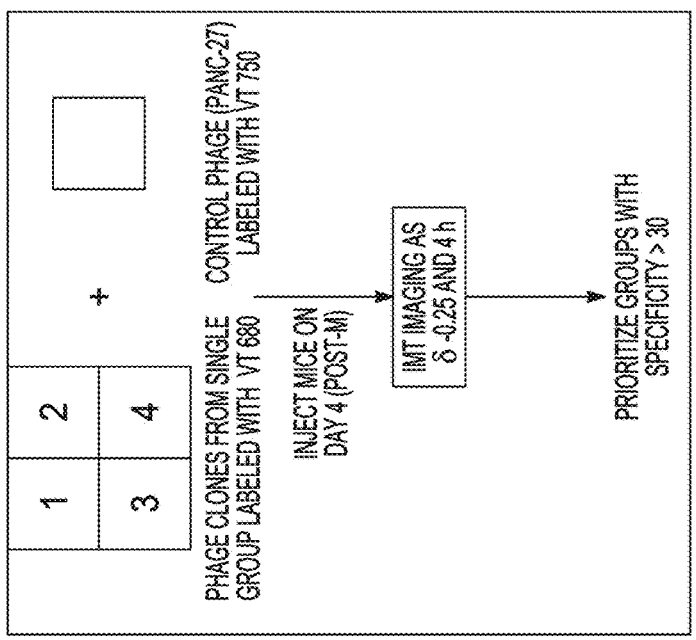

FIG. 7E

| GROUP 1<br>B-40/B-22<br>B-47<br>B-45<br>B-9 | GROUP 2<br>I-42<br>I-29<br>I-36<br>I-18 | GROUP 3<br>I-10<br>I-19<br>I-47<br>I-37 | GROUP 4<br>I-1<br>I-8<br>I-12<br>I-24 |
|---|---|---|---|
| GROUP 5<br>B-14<br>B-24<br>B-35<br>B-25 | GROUP 6<br>B-10<br>B-38<br>B-21<br>B-31 | GROUP 7<br>B-17<br>B-6<br>B-49<br>B-12 | GROUP 8<br>I-16<br>I-20<br>I-49<br>I-39 |
| GROUP 9<br>B-37<br>B-28<br>B-20<br>B-41 | GROUP 10<br>I-34<br>I-48<br>I-26<br>I-38 | GROUP 11<br>B-2<br>B-44<br>B-48<br>B-39 | GROUP 12<br>I-22<br>I-30<br>I-3<br>I-28 |
| GROUP 13<br>B-7<br>B-26<br>B-27<br>B-33 | GROUP 14<br>B-4<br>B-13<br>B-16<br>B-30 | GROUP 15<br>I-4<br>B-16/I-5<br>I-17<br>I-44 | GROUP 16<br>B-1<br>B-5<br>B-32<br>B-46 |
| GROUP 17<br>B-8<br>B-11<br>B-18<br>B-50 | GROUP 18<br>B-23<br>B-29<br>B-42<br>B-43 | GROUP 19<br>B-3<br>B-15<br>B-19<br>B-36 | GROUP 20<br>I-11<br>I-14<br>I-32<br>I-46 |
| GROUP 21<br>I-9<br>I-15<br>I-21<br>I-31/I-35 | GROUP 22<br>I-2<br>I-7<br>I-33<br>I-45 | GROUP 23<br>I-13<br>I-23<br>I-25<br>I-50 | |

FIG. 7D

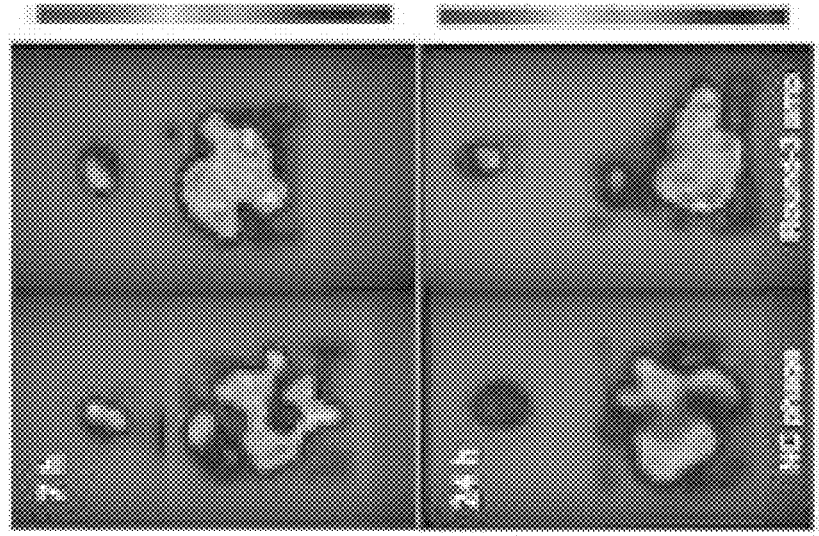

FIG. 7C

| | BATCH-1 | | | | | BATCH-2 | | | | | BATCH-3 | | | | |
|---|---|---|---|---|---|---|---|---|---|---|---|---|---|---|---|
| | NCP | I-1 | B-40 | B-50 | B-29 | NCP | I-1 | B-40 | B-50 | B-29 | NCP | I-1 | B-40 | B-50 | B-29 |
| SIZE (nm) | 106 | 123 | 103 | 112 | 116 | 120 | 105 | 117 | 109 | 110 | 113 | 121 | 104 | 116 | 103 |
| CONCENTRATION ($10^{12}$ PER mL) | 15 | 1.4 | 10 | 13 | 7.4 | 7.4 | 6.45 | 12.6 | 8.37 | 15.4 | 11.3 | 7.24 | 7.18 | 11.5 | 9.45 |
| PEPTIDES/ LIPOSOME | 530 | 800 | 790 | 645 | 678 | 750 | 564 | 678 | 586 | 739 | 655 | 639 | 556 | 735 | 605 |

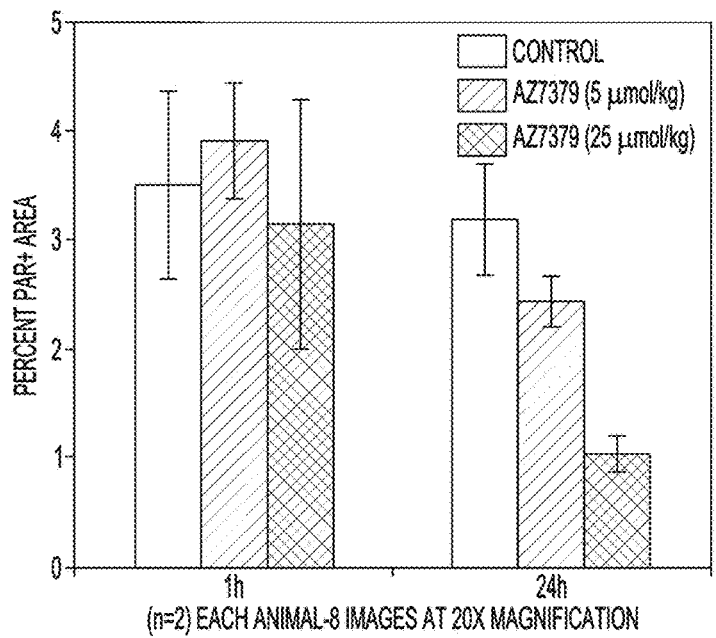

FIG. 23

| SAMPLES | DIAGNOSIS | TISSUE TYPE |
|---|---|---|
| KK-35-16 | ST-ELEVATION MYOCARDIAL INFARCTION INVOLVING THE LEFT-POSTERO-LATERAL WALL (100% OCCLUSION OF LEFT CIRCUMFLEX CORONARY ARTERY) | 2 WEEKS POST-INITIAL MI |
| KK-120-8 | ACUTE RESPIRATORY FAILURE AND ACUTE ON CHRONIC CHF (PRIOR SINGLE CHAMBER ICD IMPLANTATION) | 25 DAYS POST-INITIAL MI |
| KK-165-9 | ANTEROLATERAL MYOCARDIAL INFARCTION | 8 DAYS POST-INITIAL MI |
| KK-192-10 | ST-ELEVATION MYOCARDIAL INFARCTION WITH TROPONIN OF 18 | 5 DAYS POST-INITIAL MI |

FIG. 24A

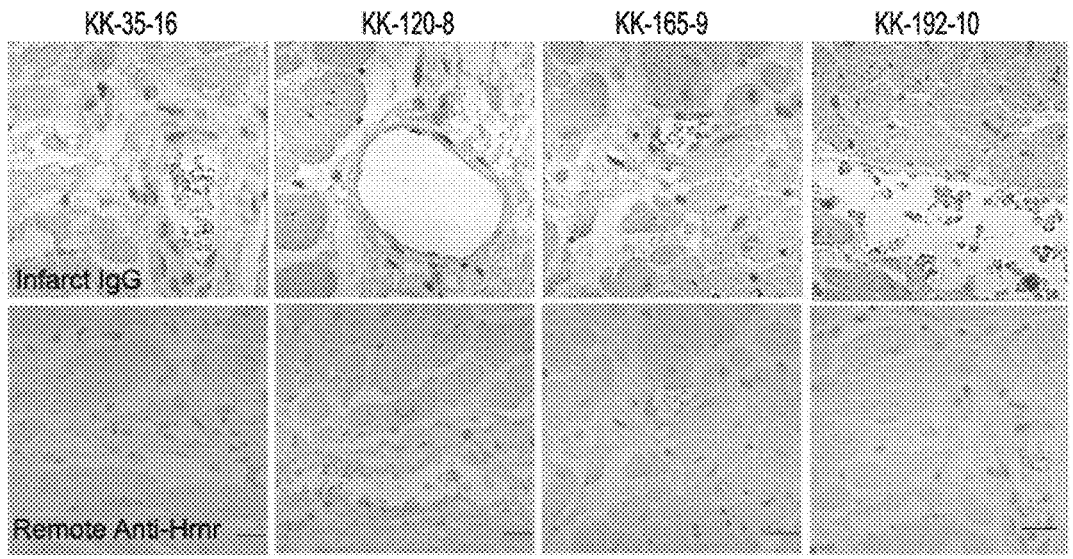

FIG. 24B

| PROPERTIES | PTK787 |
|---|---|
| IC50 (VEGFR2/KDR) | 37 nM (c) |
| pKa | 15.17, 4.95 |
| POLAR SURFACE AREA $A^2$ | 50.7 (b) |
| TOTAL AREA $A^2$ | 454.75 (b) |
| NON-POLAR AREA $A^2$ | 404.05 (b) |
| NON-POLAR/POLAR | 7.969 (b) |
| SOLUBILITY (mM) WATER | 23.82 (c) |
| CHARGE [pH] | 0 [6, 7, 8] |
| pI | 10.5 (b) |
| LOG P | 3.8 (a) |
| LOG D | 4.54 (a) |
FIG. 25A
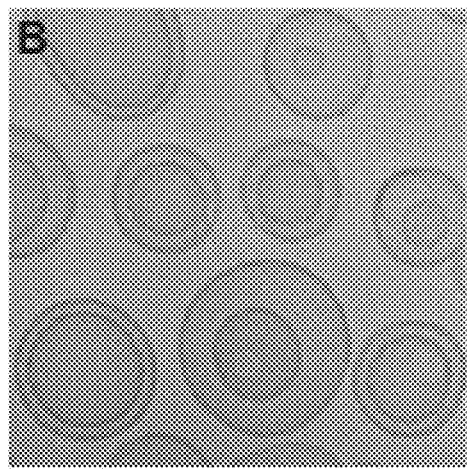
FIG. 25B
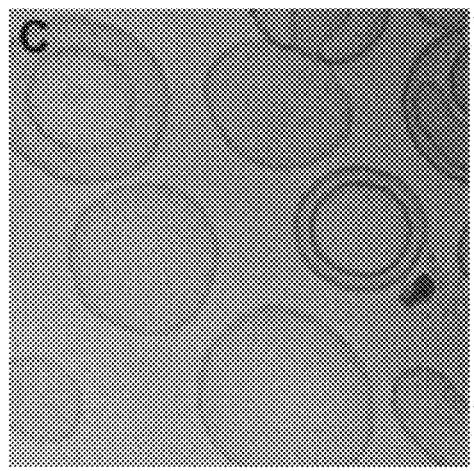
FIG. 25C
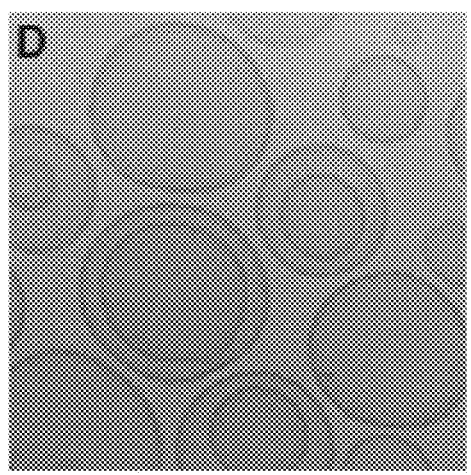
FIG. 25D
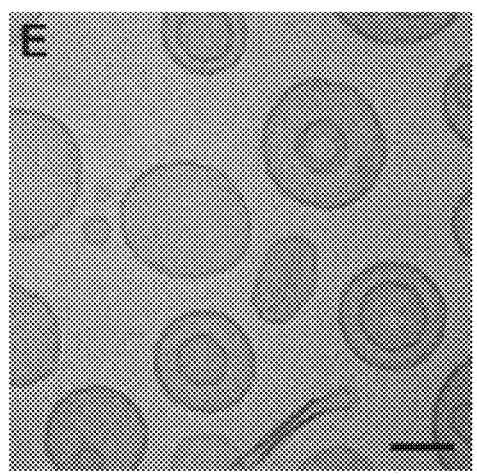
FIG. 25E

SEQUENCE LISTING

```
<160> NUMBER OF SEQ ID NOS: 255

<210> SEQ ID NO 1
<211> LENGTH: 21
<212> TYPE: DNA
<213> ORGANISM: Artificial Sequence
<220> FEATURE:
<223> OTHER INFORMATION: A synthetic primer

<400> SEQUENCE: 1
cctttagtgg tacctttcta t                                                 21

<210> SEQ ID NO 2
<211> LENGTH: 21
<212> TYPE: DNA
<213> ORGANISM: Artificial Sequence
<220> FEATURE:
<223> OTHER INFORMATION: A synthetic primer

<400> SEQUENCE: 2
gccctcatag ttagcgtaac g                                                 21

<210> SEQ ID NO 3
<211> LENGTH: 7
<212> TYPE: PRT
<213> ORGANISM: Homo sapiens

<400> SEQUENCE: 3

Asn Gln Leu Pro Leu His Ala
1               5

<210> SEQ ID NO 4
<211> LENGTH: 7
<212> TYPE: PRT
<213> ORGANISM: Homo sapiens

<400> SEQUENCE: 4

Phe Pro Ser Thr Ile Thr Pro
1               5

<210> SEQ ID NO 5
<211> LENGTH: 7
<212> TYPE: PRT
<213> ORGANISM: Homo sapiens

<400> SEQUENCE: 5

Gln Pro Trp Pro Thr Ser Ile
```

```
<210> SEQ ID NO 6
<211> LENGTH: 7
<212> TYPE: PRT
<213> ORGANISM: Homo sapiens

<400> SEQUENCE: 6

Arg Pro Pro Ala Leu Ala Pro
1               5

<210> SEQ ID NO 7
<211> LENGTH: 7
<212> TYPE: PRT
<213> ORGANISM: Homo sapiens

<400> SEQUENCE: 7

Ser His Pro Ala Ser His Asp
1               5

<210> SEQ ID NO 8
<211> LENGTH: 7
<212> TYPE: PRT
<213> ORGANISM: Homo sapiens

<400> SEQUENCE: 8

Glu Ser Arg Gln Val Thr Pro
1               5

<210> SEQ ID NO 9
<211> LENGTH: 7
<212> TYPE: PRT
<213> ORGANISM: Homo sapiens

<400> SEQUENCE: 9

Asp Pro Arg Ala Thr Met Tyr
1               5

<210> SEQ ID NO 10
<211> LENGTH: 7
<212> TYPE: PRT
<213> ORGANISM: Homo sapiens

<400> SEQUENCE: 10

Ser Leu Leu Asn Arg Met Pro
1               5

<210> SEQ ID NO 11
<211> LENGTH: 7
<212> TYPE: PRT
<213> ORGANISM: Homo sapiens

<400> SEQUENCE: 11

Leu Thr Pro Val Pro Gly Gln
1               5

<210> SEQ ID NO 12
<211> LENGTH: 7
<212> TYPE: PRT
<213> ORGANISM: Homo sapiens

<400> SEQUENCE: 12

His Phe Tyr Pro Ser Leu Leu
1               5
```

<210> SEQ ID NO 13
<211> LENGTH: 7
<212> TYPE: PRT
<213> ORGANISM: Homo sapiens

<400> SEQUENCE: 13

His Ser Val Pro Thr Pro Thr
1               5

<210> SEQ ID NO 14
<211> LENGTH: 6
<212> TYPE: PRT
<213> ORGANISM: Homo sapiens

<400> SEQUENCE: 14

Thr Met Gln His Asp Gly
1               5

<210> SEQ ID NO 15
<211> LENGTH: 7
<212> TYPE: PRT
<213> ORGANISM: Homo sapiens

<400> SEQUENCE: 15

Ser Ala Pro Gly Ser Ser Pro
1               5

<210> SEQ ID NO 16
<211> LENGTH: 7
<212> TYPE: PRT
<213> ORGANISM: Homo sapiens

<400> SEQUENCE: 16

Arg Met Ser Pro Tyr Asp Ala
1               5

<210> SEQ ID NO 17
<211> LENGTH: 7
<212> TYPE: PRT
<213> ORGANISM: Homo sapiens

<400> SEQUENCE: 17

Tyr Ala Thr Gln Ser Ser Pro
1               5

<210> SEQ ID NO 18
<211> LENGTH: 7
<212> TYPE: PRT
<213> ORGANISM: Homo sapiens

<400> SEQUENCE: 18

Ala Thr Asn Gly Phe Ala Gln
1               5

<210> SEQ ID NO 19
<211> LENGTH: 7
<212> TYPE: PRT
<213> ORGANISM: Homo sapiens

<400> SEQUENCE: 19

Leu Gln Pro Pro His Ala Lys
1               5

<210> SEQ ID NO 20

```
<211> LENGTH: 7
<212> TYPE: PRT
<213> ORGANISM: Homo sapiens

<400> SEQUENCE: 20

Thr Leu Leu Pro Thr Ser His
1               5

<210> SEQ ID NO 21
<211> LENGTH: 7
<212> TYPE: PRT
<213> ORGANISM: Homo sapiens

<400> SEQUENCE: 21

Thr Val Val Pro Lys Ala Thr
1               5

<210> SEQ ID NO 22
<211> LENGTH: 7
<212> TYPE: PRT
<213> ORGANISM: Homo sapiens

<400> SEQUENCE: 22

Ser His Ser Asn Ala Arg Ser
1               5

<210> SEQ ID NO 23
<211> LENGTH: 7
<212> TYPE: PRT
<213> ORGANISM: Homo sapiens

<400> SEQUENCE: 23

Ser Pro Gln Ile Thr Arg Leu
1               5

<210> SEQ ID NO 24
<211> LENGTH: 7
<212> TYPE: PRT
<213> ORGANISM: Homo sapiens

<400> SEQUENCE: 24

Leu Pro Leu Asn Ser His Ser
1               5

<210> SEQ ID NO 25
<211> LENGTH: 7
<212> TYPE: PRT
<213> ORGANISM: Homo sapiens

<400> SEQUENCE: 25

Phe Ser Pro Phe Arg His Val
1               5

<210> SEQ ID NO 26
<211> LENGTH: 7
<212> TYPE: PRT
<213> ORGANISM: Homo sapiens

<400> SEQUENCE: 26

Asp Ile Ser Ser His Ala Arg
1               5

<210> SEQ ID NO 27
<211> LENGTH: 7
<212> TYPE: PRT
```

-continued

<213> ORGANISM: Homo sapiens

<400> SEQUENCE: 27

Ser Pro Gln Trp Arg Ser Ser
1               5

<210> SEQ ID NO 28
<211> LENGTH: 7
<212> TYPE: PRT
<213> ORGANISM: Homo sapiens

<400> SEQUENCE: 28

Leu Gln Gly Pro Thr Gln Val
1               5

<210> SEQ ID NO 29
<211> LENGTH: 7
<212> TYPE: PRT
<213> ORGANISM: Homo sapiens

<400> SEQUENCE: 29

Thr Pro Ser Ser Ser Leu Glu
1               5

<210> SEQ ID NO 30
<211> LENGTH: 7
<212> TYPE: PRT
<213> ORGANISM: Homo sapiens

<400> SEQUENCE: 30

His Gln Glu Asn Thr Lys Leu
1               5

<210> SEQ ID NO 31
<211> LENGTH: 7
<212> TYPE: PRT
<213> ORGANISM: Homo sapiens

<400> SEQUENCE: 31

Ala Met Arg Pro Pro Leu Asn
1               5

<210> SEQ ID NO 32
<211> LENGTH: 7
<212> TYPE: PRT
<213> ORGANISM: Homo sapiens

<400> SEQUENCE: 32

Ser Thr Leu Lys Ala Pro Gly
1               5

<210> SEQ ID NO 33
<211> LENGTH: 7
<212> TYPE: PRT
<213> ORGANISM: Homo sapiens

<400> SEQUENCE: 33

Thr Ala Gln Pro Arg Leu Ile
1               5

<210> SEQ ID NO 34
<211> LENGTH: 7
<212> TYPE: PRT
<213> ORGANISM: Homo sapiens

```
<400> SEQUENCE: 34

Glu Val Tyr Ala Pro Pro Arg
1               5

<210> SEQ ID NO 35
<211> LENGTH: 7
<212> TYPE: PRT
<213> ORGANISM: Homo sapiens

<400> SEQUENCE: 35

Ala Thr Met Ser Arg Ala Pro
1               5

<210> SEQ ID NO 36
<211> LENGTH: 7
<212> TYPE: PRT
<213> ORGANISM: Homo sapiens

<400> SEQUENCE: 36

Thr Pro Gly Gly Lys Ser Pro
1               5

<210> SEQ ID NO 37
<211> LENGTH: 7
<212> TYPE: PRT
<213> ORGANISM: Homo sapiens

<400> SEQUENCE: 37

Tyr Asn Tyr Gly Thr Leu Val
1               5

<210> SEQ ID NO 38
<211> LENGTH: 7
<212> TYPE: PRT
<213> ORGANISM: Homo sapiens

<400> SEQUENCE: 38

Gly Leu Ser Gln Leu Gln Arg
1               5

<210> SEQ ID NO 39
<211> LENGTH: 7
<212> TYPE: PRT
<213> ORGANISM: Homo sapiens

<400> SEQUENCE: 39

Tyr Pro Asn His Ala Ser Pro
1               5

<210> SEQ ID NO 40
<211> LENGTH: 7
<212> TYPE: PRT
<213> ORGANISM: Homo sapiens

<400> SEQUENCE: 40

Ser Asp Thr Trp Ser Ser Arg
1               5

<210> SEQ ID NO 41
<211> LENGTH: 7
<212> TYPE: PRT
<213> ORGANISM: Homo sapiens

<400> SEQUENCE: 41
```

Thr Leu Ala Gln Ile His His
1               5

<210> SEQ ID NO 42
<211> LENGTH: 7
<212> TYPE: PRT
<213> ORGANISM: Homo sapiens

<400> SEQUENCE: 42

Thr Ala Leu Pro Arg Leu Asn
1               5

<210> SEQ ID NO 43
<211> LENGTH: 7
<212> TYPE: PRT
<213> ORGANISM: Homo sapiens

<400> SEQUENCE: 43

Arg Asp Leu Gln Arg Pro Tyr
1               5

<210> SEQ ID NO 44
<211> LENGTH: 7
<212> TYPE: PRT
<213> ORGANISM: Homo sapiens

<400> SEQUENCE: 44

Gln Thr Ala His His Val Gln
1               5

<210> SEQ ID NO 45
<211> LENGTH: 7
<212> TYPE: PRT
<213> ORGANISM: Homo sapiens

<400> SEQUENCE: 45

Ser Ala Leu Pro Asn Leu Tyr
1               5

<210> SEQ ID NO 46
<211> LENGTH: 7
<212> TYPE: PRT
<213> ORGANISM: Homo sapiens

<400> SEQUENCE: 46

Ser Val Arg Thr Leu Gln Ala
1               5

<210> SEQ ID NO 47
<211> LENGTH: 7
<212> TYPE: PRT
<213> ORGANISM: Homo sapiens

<400> SEQUENCE: 47

Glu Leu His Lys Pro Gln His
1               5

<210> SEQ ID NO 48
<211> LENGTH: 7
<212> TYPE: PRT
<213> ORGANISM: Homo sapiens

<400> SEQUENCE: 48

Thr Ala Gln Thr Ile Ser Asp
1               5

<210> SEQ ID NO 49
<211> LENGTH: 7
<212> TYPE: PRT
<213> ORGANISM: Homo sapiens

<400> SEQUENCE: 49

Ala Ala Asp Met Val Val Phe
1               5

<210> SEQ ID NO 50
<211> LENGTH: 7
<212> TYPE: PRT
<213> ORGANISM: Homo sapiens

<400> SEQUENCE: 50

Ser Ser Val Ser Leu Glu Ser
1               5

<210> SEQ ID NO 51
<211> LENGTH: 7
<212> TYPE: PRT
<213> ORGANISM: Homo sapiens

<400> SEQUENCE: 51

Ala Ile Thr Thr Arg His Gln
1               5

<210> SEQ ID NO 52
<211> LENGTH: 7
<212> TYPE: PRT
<213> ORGANISM: Homo sapiens

<400> SEQUENCE: 52

Tyr Asp Tyr Ser Ala Ser Ser
1               5

<210> SEQ ID NO 53
<211> LENGTH: 7
<212> TYPE: PRT
<213> ORGANISM: Homo sapiens

<400> SEQUENCE: 53

Asn Leu Pro His Arg Thr Ser
1               5

<210> SEQ ID NO 54
<211> LENGTH: 7
<212> TYPE: PRT
<213> ORGANISM: Homo sapiens

<400> SEQUENCE: 54

Ala Asn Arg Leu Leu Thr Pro
1               5

<210> SEQ ID NO 55
<211> LENGTH: 7
<212> TYPE: PRT
<213> ORGANISM: Homo sapiens

<400> SEQUENCE: 55

Trp Gln Tyr Pro Ser Arg Ala
1               5

```
<210> SEQ ID NO 56
<211> LENGTH: 7
<212> TYPE: PRT
<213> ORGANISM: Homo sapiens

<400> SEQUENCE: 56

Tyr Val Gln Gly Thr Ala Ser
1               5

<210> SEQ ID NO 57
<211> LENGTH: 7
<212> TYPE: PRT
<213> ORGANISM: Homo sapiens

<400> SEQUENCE: 57

His Gln Val Pro His Ser Met
1               5

<210> SEQ ID NO 58
<211> LENGTH: 7
<212> TYPE: PRT
<213> ORGANISM: Homo sapiens

<400> SEQUENCE: 58

Ser Thr Tyr Thr Val Ser Ser
1               5

<210> SEQ ID NO 59
<211> LENGTH: 7
<212> TYPE: PRT
<213> ORGANISM: Homo sapiens

<400> SEQUENCE: 59

Leu Thr Thr Asp Trp Thr Ser
1               5

<210> SEQ ID NO 60
<211> LENGTH: 7
<212> TYPE: PRT
<213> ORGANISM: Homo sapiens

<400> SEQUENCE: 60

Gln Ala Cys Glu Leu Ser Leu
1               5

<210> SEQ ID NO 61
<211> LENGTH: 7
<212> TYPE: PRT
<213> ORGANISM: Homo sapiens

<400> SEQUENCE: 61

Ser Leu Gly Ala Arg Thr Pro
1               5

<210> SEQ ID NO 62
<211> LENGTH: 7
<212> TYPE: PRT
<213> ORGANISM: Homo sapiens

<400> SEQUENCE: 62

Phe Gln Asp Gln His Pro Gln
1               5

<210> SEQ ID NO 63
<211> LENGTH: 7
```

```
<212> TYPE: PRT
<213> ORGANISM: Homo sapiens

<400> SEQUENCE: 63

Phe Asp Ala Ile Asn Gln Pro
1               5

<210> SEQ ID NO 64
<211> LENGTH: 7
<212> TYPE: PRT
<213> ORGANISM: Homo sapiens

<400> SEQUENCE: 64

Ala Ala His Ala Leu Met Lys
1               5

<210> SEQ ID NO 65
<211> LENGTH: 7
<212> TYPE: PRT
<213> ORGANISM: Homo sapiens

<400> SEQUENCE: 65

Thr Ser Leu Ser Asp Ser Gln
1               5

<210> SEQ ID NO 66
<211> LENGTH: 7
<212> TYPE: PRT
<213> ORGANISM: Homo sapiens

<400> SEQUENCE: 66

His Ala Ile Tyr Pro Arg His
1               5

<210> SEQ ID NO 67
<211> LENGTH: 7
<212> TYPE: PRT
<213> ORGANISM: Homo sapiens

<400> SEQUENCE: 67

Tyr Leu Thr Met Pro Thr Pro
1               5

<210> SEQ ID NO 68
<211> LENGTH: 7
<212> TYPE: PRT
<213> ORGANISM: Homo sapiens

<400> SEQUENCE: 68

Ser Thr Ala Ser Tyr Thr Arg
1               5

<210> SEQ ID NO 69
<211> LENGTH: 6
<212> TYPE: PRT
<213> ORGANISM: Homo sapiens

<400> SEQUENCE: 69

Ile Leu Gly Val Leu Pro
1               5

<210> SEQ ID NO 70
<211> LENGTH: 7
<212> TYPE: PRT
<213> ORGANISM: Homo sapiens
```

<400> SEQUENCE: 70

Ala Thr Thr Val Pro Ala Ser
1               5

<210> SEQ ID NO 71
<211> LENGTH: 7
<212> TYPE: PRT
<213> ORGANISM: Homo sapiens

<400> SEQUENCE: 71

Ser Met Tyr Gly Ser Tyr Asn
1               5

<210> SEQ ID NO 72
<211> LENGTH: 7
<212> TYPE: PRT
<213> ORGANISM: Homo sapiens

<400> SEQUENCE: 72

Met Asn Ser Gly Ala Val Ser
1               5

<210> SEQ ID NO 73
<211> LENGTH: 7
<212> TYPE: PRT
<213> ORGANISM: Homo sapiens

<400> SEQUENCE: 73

Trp Ala Leu Asp Arg Gly Ala
1               5

<210> SEQ ID NO 74
<211> LENGTH: 7
<212> TYPE: PRT
<213> ORGANISM: Homo sapiens

<400> SEQUENCE: 74

Arg Pro Pro Ala Leu Ala Pro
1               5

<210> SEQ ID NO 75
<211> LENGTH: 7
<212> TYPE: PRT
<213> ORGANISM: Homo sapiens

<400> SEQUENCE: 75

Ser His Pro Ala Ser His Asp
1               5

<210> SEQ ID NO 76
<211> LENGTH: 7
<212> TYPE: PRT
<213> ORGANISM: Homo sapiens

<400> SEQUENCE: 76

Thr Val Ala Pro Ser Ala Asn
1               5

<210> SEQ ID NO 77
<211> LENGTH: 7
<212> TYPE: PRT
<213> ORGANISM: Homo sapiens

<400> SEQUENCE: 77

Glu Ser Arg Gln Val Thr Pro
1               5

<210> SEQ ID NO 78
<211> LENGTH: 7
<212> TYPE: PRT
<213> ORGANISM: Homo sapiens

<400> SEQUENCE: 78

Thr Arg Ala Gly Leu Asp Phe
1               5

<210> SEQ ID NO 79
<211> LENGTH: 7
<212> TYPE: PRT
<213> ORGANISM: Homo sapiens

<400> SEQUENCE: 79

Ser His Ser Leu Leu His His
1               5

<210> SEQ ID NO 80
<211> LENGTH: 7
<212> TYPE: PRT
<213> ORGANISM: Homo sapiens

<400> SEQUENCE: 80

Leu Ala Arg Glu Pro Thr Ser
1               5

<210> SEQ ID NO 81
<211> LENGTH: 7
<212> TYPE: PRT
<213> ORGANISM: Homo sapiens

<400> SEQUENCE: 81

Tyr His Gln Thr Thr Ile Thr
1               5

<210> SEQ ID NO 82
<211> LENGTH: 7
<212> TYPE: PRT
<213> ORGANISM: Homo sapiens

<400> SEQUENCE: 82

Gln His Trp Phe Ser Pro Met
1               5

<210> SEQ ID NO 83
<211> LENGTH: 7
<212> TYPE: PRT
<213> ORGANISM: Homo sapiens

<400> SEQUENCE: 83

Gln Ser Asn Ala Gln Leu Glu
1               5

<210> SEQ ID NO 84
<211> LENGTH: 7
<212> TYPE: PRT
<213> ORGANISM: Homo sapiens

<400> SEQUENCE: 84

Ser His Thr Thr Val Asn Pro

```
1               5

<210> SEQ ID NO 85
<211> LENGTH: 7
<212> TYPE: PRT
<213> ORGANISM: Homo sapiens

<400> SEQUENCE: 85

Ser Thr Ala Arg Ala Pro Thr
1               5

<210> SEQ ID NO 86
<211> LENGTH: 7
<212> TYPE: PRT
<213> ORGANISM: Homo sapiens

<400> SEQUENCE: 86

Gly Val Gln Ile Met Gly Arg
1               5

<210> SEQ ID NO 87
<211> LENGTH: 7
<212> TYPE: PRT
<213> ORGANISM: Homo sapiens

<400> SEQUENCE: 87

Val Ser Ala Ser Ala Leu Thr
1               5

<210> SEQ ID NO 88
<211> LENGTH: 7
<212> TYPE: PRT
<213> ORGANISM: Homo sapiens

<400> SEQUENCE: 88

Asn Asp Leu Pro Arg Arg Thr
1               5

<210> SEQ ID NO 89
<211> LENGTH: 7
<212> TYPE: PRT
<213> ORGANISM: Homo sapiens

<400> SEQUENCE: 89

Ala Leu Met His Gly Thr Ser
1               5

<210> SEQ ID NO 90
<211> LENGTH: 7
<212> TYPE: PRT
<213> ORGANISM: Homo sapiens

<400> SEQUENCE: 90

Asp Pro Arg Ala Thr Met Tyr
1               5

<210> SEQ ID NO 91
<211> LENGTH: 7
<212> TYPE: PRT
<213> ORGANISM: Homo sapiens

<400> SEQUENCE: 91

Thr His Ser Pro Ser Thr His
1               5
```

<210> SEQ ID NO 92
<211> LENGTH: 7
<212> TYPE: PRT
<213> ORGANISM: Homo sapiens

<400> SEQUENCE: 92

Asp Ser Gly Phe Pro Leu Pro
1               5

<210> SEQ ID NO 93
<211> LENGTH: 7
<212> TYPE: PRT
<213> ORGANISM: Homo sapiens

<400> SEQUENCE: 93

His Leu His Tyr Ala Leu Pro
1               5

<210> SEQ ID NO 94
<211> LENGTH: 7
<212> TYPE: PRT
<213> ORGANISM: Homo sapiens

<400> SEQUENCE: 94

Glu His Gln Leu Asn Arg Ala
1               5

<210> SEQ ID NO 95
<211> LENGTH: 7
<212> TYPE: PRT
<213> ORGANISM: Homo sapiens

<400> SEQUENCE: 95

Gln Leu Thr Ile Ile Pro Gln
1               5

<210> SEQ ID NO 96
<211> LENGTH: 7
<212> TYPE: PRT
<213> ORGANISM: Homo sapiens

<400> SEQUENCE: 96

Leu Pro Arg Asn Tyr Pro Ser
1               5

<210> SEQ ID NO 97
<211> LENGTH: 7
<212> TYPE: PRT
<213> ORGANISM: Homo sapiens

<400> SEQUENCE: 97

Ala Ser Val His Leu Pro Pro
1               5

<210> SEQ ID NO 98
<211> LENGTH: 7
<212> TYPE: PRT
<213> ORGANISM: Homo sapiens

<400> SEQUENCE: 98

Ala Asn Thr Thr Pro Arg His
1               5

<210> SEQ ID NO 99

```
<211> LENGTH: 7
<212> TYPE: PRT
<213> ORGANISM: Homo sapiens

<400> SEQUENCE: 99

Gln Asn Ser Gln Leu Ser Arg
1               5

<210> SEQ ID NO 100
<211> LENGTH: 7
<212> TYPE: PRT
<213> ORGANISM: Homo sapiens

<400> SEQUENCE: 100

Leu Pro Ser Tyr His Val Pro
1               5

<210> SEQ ID NO 101
<211> LENGTH: 7
<212> TYPE: PRT
<213> ORGANISM: Homo sapiens

<400> SEQUENCE: 101

Trp Pro Thr Pro Pro Tyr Ala
1               5

<210> SEQ ID NO 102
<211> LENGTH: 7
<212> TYPE: PRT
<213> ORGANISM: Homo sapiens

<400> SEQUENCE: 102

Val Gln Thr Tyr Ala Arg Val
1               5

<210> SEQ ID NO 103
<211> LENGTH: 7
<212> TYPE: PRT
<213> ORGANISM: Homo sapiens

<400> SEQUENCE: 103

Ile Thr Ala Pro His Pro His
1               5

<210> SEQ ID NO 104
<211> LENGTH: 7
<212> TYPE: PRT
<213> ORGANISM: Homo sapiens

<400> SEQUENCE: 104

Tyr Arg Ala Pro Trp Pro Pro
1               5

<210> SEQ ID NO 105
<211> LENGTH: 7
<212> TYPE: PRT
<213> ORGANISM: Homo sapiens

<400> SEQUENCE: 105

Ala Thr Leu Thr His Pro Pro
1               5

<210> SEQ ID NO 106
<211> LENGTH: 7
<212> TYPE: PRT
```

<213> ORGANISM: Homo sapiens

<400> SEQUENCE: 106

Thr Ala Pro Ser Ala Arg His
1               5

<210> SEQ ID NO 107
<211> LENGTH: 7
<212> TYPE: PRT
<213> ORGANISM: Homo sapiens

<400> SEQUENCE: 107

His Lys Tyr Ile Ser Ala Thr
1               5

<210> SEQ ID NO 108
<211> LENGTH: 7
<212> TYPE: PRT
<213> ORGANISM: Homo sapiens

<400> SEQUENCE: 108

Gln Ser Pro Asp Glu Val Trp
1               5

<210> SEQ ID NO 109
<211> LENGTH: 7
<212> TYPE: PRT
<213> ORGANISM: Homo sapiens

<400> SEQUENCE: 109

Thr Asp Ser Leu Arg Leu Leu
1               5

<210> SEQ ID NO 110
<211> LENGTH: 7
<212> TYPE: PRT
<213> ORGANISM: Homo sapiens

<400> SEQUENCE: 110

Ala Phe Pro Val Ser His Asn
1               5

<210> SEQ ID NO 111
<211> LENGTH: 7
<212> TYPE: PRT
<213> ORGANISM: Homo sapiens

<400> SEQUENCE: 111

Ala Ala Gly Gln Gln Phe Pro
1               5

<210> SEQ ID NO 112
<211> LENGTH: 7
<212> TYPE: PRT
<213> ORGANISM: Homo sapiens

<400> SEQUENCE: 112

Gly Pro Met Leu Ala Arg Gly
1               5

<210> SEQ ID NO 113
<211> LENGTH: 7
<212> TYPE: PRT
<213> ORGANISM: Homo sapiens

<400> SEQUENCE: 113

His Thr Ile Gln Phe Thr Pro
1               5

<210> SEQ ID NO 114
<211> LENGTH: 7
<212> TYPE: PRT
<213> ORGANISM: Homo sapiens

<400> SEQUENCE: 114

Ser Pro Gln Met Thr Leu Ser
1               5

<210> SEQ ID NO 115
<211> LENGTH: 7
<212> TYPE: PRT
<213> ORGANISM: Homo sapiens

<400> SEQUENCE: 115

Thr Ile Pro Ser Arg Val Leu
1               5

<210> SEQ ID NO 116
<211> LENGTH: 7
<212> TYPE: PRT
<213> ORGANISM: Homo sapiens

<400> SEQUENCE: 116

Glu Leu Ser Ser Gln Leu Ala
1               5

<210> SEQ ID NO 117
<211> LENGTH: 7
<212> TYPE: PRT
<213> ORGANISM: Homo sapiens

<400> SEQUENCE: 117

Ser Glu Pro Gly Arg Ser Leu
1               5

<210> SEQ ID NO 118
<211> LENGTH: 7
<212> TYPE: PRT
<213> ORGANISM: Homo sapiens

<400> SEQUENCE: 118

Ser Ser Leu Pro Leu Arg Lys
1               5

<210> SEQ ID NO 119
<211> LENGTH: 7
<212> TYPE: PRT
<213> ORGANISM: Homo sapiens

<400> SEQUENCE: 119

Ala Cys Ala Ser Asn Lys Ser
1               5

<210> SEQ ID NO 120
<211> LENGTH: 7
<212> TYPE: PRT
<213> ORGANISM: Homo sapiens

<400> SEQUENCE: 120

Ala Met Ser Ser Arg Ser Leu
1               5

<210> SEQ ID NO 121
<211> LENGTH: 7
<212> TYPE: PRT
<213> ORGANISM: Homo sapiens

<400> SEQUENCE: 121

Ala Ala Lys Thr Pro Thr Glu
1               5

<210> SEQ ID NO 122
<211> LENGTH: 7
<212> TYPE: PRT
<213> ORGANISM: Homo sapiens

<400> SEQUENCE: 122

Thr Met Pro Gly Lys Thr Ser
1               5

<210> SEQ ID NO 123
<211> LENGTH: 7
<212> TYPE: PRT
<213> ORGANISM: Homo sapiens

<400> SEQUENCE: 123

Ala Pro Pro Thr Arg Tyr His
1               5

<210> SEQ ID NO 124
<211> LENGTH: 7
<212> TYPE: PRT
<213> ORGANISM: Homo sapiens

<400> SEQUENCE: 124

Ala Leu Asn Ser Leu Thr Asn
1               5

<210> SEQ ID NO 125
<211> LENGTH: 7
<212> TYPE: PRT
<213> ORGANISM: Homo sapiens

<400> SEQUENCE: 125

Gln Val Gln Thr His His Asn
1               5

<210> SEQ ID NO 126
<211> LENGTH: 7
<212> TYPE: PRT
<213> ORGANISM: Homo sapiens

<400> SEQUENCE: 126

Ala Leu His Ser Ala Arg Val
1               5

<210> SEQ ID NO 127
<211> LENGTH: 7
<212> TYPE: PRT
<213> ORGANISM: Homo sapiens

<400> SEQUENCE: 127

Gln Ala Pro Ser Arg Thr His
1               5

<210> SEQ ID NO 128
<211> LENGTH: 7
<212> TYPE: PRT
<213> ORGANISM: Homo sapiens

<400> SEQUENCE: 128

Asn Thr Ser Ala Val Ser Val
1               5

<210> SEQ ID NO 129
<211> LENGTH: 7
<212> TYPE: PRT
<213> ORGANISM: Homo sapiens

<400> SEQUENCE: 129

Ala Leu Ile Pro Lys Pro Arg
1               5

<210> SEQ ID NO 130
<211> LENGTH: 7
<212> TYPE: PRT
<213> ORGANISM: Homo sapiens

<400> SEQUENCE: 130

Thr Ser Pro Thr Ser Phe Asp
1               5

<210> SEQ ID NO 131
<211> LENGTH: 7
<212> TYPE: PRT
<213> ORGANISM: Homo sapiens

<400> SEQUENCE: 131

Lys Trp Pro Leu Ser His Pro
1               5

<210> SEQ ID NO 132
<211> LENGTH: 7
<212> TYPE: PRT
<213> ORGANISM: Homo sapiens

<400> SEQUENCE: 132

Ala Gly Asn Gly Thr Thr Pro
1               5

<210> SEQ ID NO 133
<211> LENGTH: 7
<212> TYPE: PRT
<213> ORGANISM: Homo sapiens

<400> SEQUENCE: 133

Phe Pro Gly Arg Pro Ser Pro
1               5

<210> SEQ ID NO 134
<211> LENGTH: 7
<212> TYPE: PRT
<213> ORGANISM: Homo sapiens

<400> SEQUENCE: 134

Thr His Leu Pro Trp Gln Thr
1               5

<210> SEQ ID NO 135
<211> LENGTH: 7
<212> TYPE: PRT
<213> ORGANISM: Homo sapiens

<400> SEQUENCE: 135

Ala Thr Pro Leu Trp Leu Lys
1               5

<210> SEQ ID NO 136
<211> LENGTH: 7
<212> TYPE: PRT
<213> ORGANISM: Homo sapiens

<400> SEQUENCE: 136

Val Tyr Pro His Pro Glu Arg
1               5

<210> SEQ ID NO 137
<211> LENGTH: 7
<212> TYPE: PRT
<213> ORGANISM: Homo sapiens

<400> SEQUENCE: 137

Asn Gln Leu Thr Thr Leu Asn
1               5

<210> SEQ ID NO 138
<211> LENGTH: 7
<212> TYPE: PRT
<213> ORGANISM: Homo sapiens

<400> SEQUENCE: 138

Ala Thr Ser Ile Arg Tyr Thr
1               5

<210> SEQ ID NO 139
<211> LENGTH: 7
<212> TYPE: PRT
<213> ORGANISM: Homo sapiens

<400> SEQUENCE: 139

Ser Thr Ile His Gly Ser Thr
1               5

<210> SEQ ID NO 140
<211> LENGTH: 7
<212> TYPE: PRT
<213> ORGANISM: Homo sapiens

<400> SEQUENCE: 140

Lys Ser Tyr Val Ser Pro Ser
1               5

<210> SEQ ID NO 141
<211> LENGTH: 7
<212> TYPE: PRT
<213> ORGANISM: Homo sapiens

<400> SEQUENCE: 141

Ser Pro Ser Met Leu Gln Lys
1               5

<210> SEQ ID NO 142
<211> LENGTH: 7

```
<212> TYPE: PRT
<213> ORGANISM: Homo sapiens

<400> SEQUENCE: 142

Gly Thr Trp Leu Ser Arg Gly
1               5

<210> SEQ ID NO 143
<211> LENGTH: 7
<212> TYPE: PRT
<213> ORGANISM: Homo sapiens

<400> SEQUENCE: 143

Ser Val Glu Ser Ala Trp Arg
1               5

<210> SEQ ID NO 144
<211> LENGTH: 7
<212> TYPE: PRT
<213> ORGANISM: Homo sapiens

<400> SEQUENCE: 144

Gln Asn Gly Gly Pro Ser Val
1               5

<210> SEQ ID NO 145
<211> LENGTH: 7
<212> TYPE: PRT
<213> ORGANISM: Homo sapiens

<400> SEQUENCE: 145

Ser Thr Asp Lys Val Pro Leu
1               5

<210> SEQ ID NO 146
<211> LENGTH: 7
<212> TYPE: PRT
<213> ORGANISM: Homo sapiens

<400> SEQUENCE: 146

Ser Pro Thr Gly Trp Ala Pro
1               5

<210> SEQ ID NO 147
<211> LENGTH: 7
<212> TYPE: PRT
<213> ORGANISM: Homo sapiens

<400> SEQUENCE: 147

Gln Arg Leu Pro Gln Thr Ala
1               5

<210> SEQ ID NO 148
<211> LENGTH: 7
<212> TYPE: PRT
<213> ORGANISM: Homo sapiens

<400> SEQUENCE: 148

His Val Val Ser Pro Pro Pro
1               5

<210> SEQ ID NO 149
<211> LENGTH: 7
<212> TYPE: PRT
<213> ORGANISM: Homo sapiens
```

<400> SEQUENCE: 149

Thr Ile Thr Asn Pro Arg Pro
1               5

<210> SEQ ID NO 150
<211> LENGTH: 7
<212> TYPE: PRT
<213> ORGANISM: Homo sapiens

<400> SEQUENCE: 150

Thr Gln Tyr Phe Tyr Leu Pro
1               5

<210> SEQ ID NO 151
<211> LENGTH: 7
<212> TYPE: PRT
<213> ORGANISM: Homo sapiens

<400> SEQUENCE: 151

Gly Asn Thr Pro Ser Arg Ala
1               5

<210> SEQ ID NO 152
<211> LENGTH: 7
<212> TYPE: PRT
<213> ORGANISM: Homo sapiens

<400> SEQUENCE: 152

Thr Asp Thr Glu Ser Lys Arg
1               5

<210> SEQ ID NO 153
<211> LENGTH: 7
<212> TYPE: PRT
<213> ORGANISM: Homo sapiens

<400> SEQUENCE: 153

Trp Val Pro Ser Thr Trp Gly
1               5

<210> SEQ ID NO 154
<211> LENGTH: 7
<212> TYPE: PRT
<213> ORGANISM: Homo sapiens

<400> SEQUENCE: 154

His Arg Ala Asp Met His Phe
1               5

<210> SEQ ID NO 155
<211> LENGTH: 7
<212> TYPE: PRT
<213> ORGANISM: Homo sapiens

<400> SEQUENCE: 155

Tyr Gln Leu Thr Ser Ser Leu
1               5

<210> SEQ ID NO 156
<211> LENGTH: 7
<212> TYPE: PRT
<213> ORGANISM: Homo sapiens

<400> SEQUENCE: 156

Trp Thr Pro Ser Val Arg Pro
1               5

<210> SEQ ID NO 157
<211> LENGTH: 7
<212> TYPE: PRT
<213> ORGANISM: Homo sapiens

<400> SEQUENCE: 157

Asn Lys Asn Tyr Ile Gln His
1               5

<210> SEQ ID NO 158
<211> LENGTH: 7
<212> TYPE: PRT
<213> ORGANISM: Homo sapiens

<400> SEQUENCE: 158

Thr Thr Val Leu Thr Pro Lys
1               5

<210> SEQ ID NO 159
<211> LENGTH: 7
<212> TYPE: PRT
<213> ORGANISM: Homo sapiens

<400> SEQUENCE: 159

Ile Pro Thr Pro Gln Pro Phe
1               5

<210> SEQ ID NO 160
<211> LENGTH: 7
<212> TYPE: PRT
<213> ORGANISM: Homo sapiens

<400> SEQUENCE: 160

Gly Gln Ser Leu Ser Asn Thr
1               5

<210> SEQ ID NO 161
<211> LENGTH: 7
<212> TYPE: PRT
<213> ORGANISM: Homo sapiens

<400> SEQUENCE: 161

Asp Arg Met Ser Val Arg Thr
1               5

<210> SEQ ID NO 162
<211> LENGTH: 7
<212> TYPE: PRT
<213> ORGANISM: Homo sapiens

<400> SEQUENCE: 162

Tyr Ala Gly Pro Tyr Gln His
1               5

<210> SEQ ID NO 163
<211> LENGTH: 7
<212> TYPE: PRT
<213> ORGANISM: Homo sapiens

<400> SEQUENCE: 163

Ala Gln Ser Glu Thr Ala Pro

<210> SEQ ID NO 164
<211> LENGTH: 7
<212> TYPE: PRT
<213> ORGANISM: Homo sapiens

<400> SEQUENCE: 164

Leu Pro Leu Gln Lys Ile Ser
1               5

<210> SEQ ID NO 165
<211> LENGTH: 7
<212> TYPE: PRT
<213> ORGANISM: Homo sapiens

<400> SEQUENCE: 165

Thr Glu Met Pro Thr Phe Pro
1               5

<210> SEQ ID NO 166
<211> LENGTH: 7
<212> TYPE: PRT
<213> ORGANISM: Homo sapiens

<400> SEQUENCE: 166

Ser Lys Ser Ile Thr Ala Thr
1               5

<210> SEQ ID NO 167
<211> LENGTH: 7
<212> TYPE: PRT
<213> ORGANISM: Homo sapiens

<400> SEQUENCE: 167

Ser Gly Leu Thr Ser Gly Leu
1               5

<210> SEQ ID NO 168
<211> LENGTH: 7
<212> TYPE: PRT
<213> ORGANISM: Homo sapiens

<400> SEQUENCE: 168

Ser Trp Asn Thr Phe Leu Leu
1               5

<210> SEQ ID NO 169
<211> LENGTH: 7
<212> TYPE: PRT
<213> ORGANISM: Homo sapiens

<400> SEQUENCE: 169

Gln His His Ala Pro Leu Thr
1               5

<210> SEQ ID NO 170
<211> LENGTH: 7
<212> TYPE: PRT
<213> ORGANISM: Homo sapiens

<400> SEQUENCE: 170

Ile Gln Pro Asp Ala Arg Asp
1               5

```
<210> SEQ ID NO 171
<211> LENGTH: 7
<212> TYPE: PRT
<213> ORGANISM: Homo sapiens

<400> SEQUENCE: 171

Ala Ala Gln Thr Ser Thr Pro
1               5

<210> SEQ ID NO 172
<211> LENGTH: 7
<212> TYPE: PRT
<213> ORGANISM: Homo sapiens

<400> SEQUENCE: 172

Ser Thr Ser Gly Arg Leu Pro
1               5

<210> SEQ ID NO 173
<211> LENGTH: 7
<212> TYPE: PRT
<213> ORGANISM: Homo sapiens

<400> SEQUENCE: 173

Ser Asn Tyr Asn Leu Pro Val
1               5

<210> SEQ ID NO 174
<211> LENGTH: 7
<212> TYPE: PRT
<213> ORGANISM: Homo sapiens

<400> SEQUENCE: 174

Asn Leu Pro Thr Val Asp Thr
1               5

<210> SEQ ID NO 175
<211> LENGTH: 7
<212> TYPE: PRT
<213> ORGANISM: Homo sapiens

<400> SEQUENCE: 175

Ser Tyr Met Ala Pro Met Asp
1               5

<210> SEQ ID NO 176
<211> LENGTH: 7
<212> TYPE: PRT
<213> ORGANISM: Homo sapiens

<400> SEQUENCE: 176

Gly Asp His Leu Pro His Gln
1               5

<210> SEQ ID NO 177
<211> LENGTH: 7
<212> TYPE: PRT
<213> ORGANISM: Homo sapiens

<400> SEQUENCE: 177

Leu Arg His Pro Ser Ile Pro
1               5

<210> SEQ ID NO 178
```

```
<211> LENGTH: 7
<212> TYPE: PRT
<213> ORGANISM: Homo sapiens

<400> SEQUENCE: 178

Leu Pro Pro Gly Pro Leu Gln
1               5

<210> SEQ ID NO 179
<211> LENGTH: 7
<212> TYPE: PRT
<213> ORGANISM: Homo sapiens

<400> SEQUENCE: 179

Ser Pro Tyr Ser Leu Tyr Ala
1               5

<210> SEQ ID NO 180
<211> LENGTH: 7
<212> TYPE: PRT
<213> ORGANISM: Homo sapiens

<400> SEQUENCE: 180

Ala Thr Pro Ser Trp Trp Ala
1               5

<210> SEQ ID NO 181
<211> LENGTH: 7
<212> TYPE: PRT
<213> ORGANISM: Homo sapiens

<400> SEQUENCE: 181

Tyr Leu Pro Asn Gly Pro Arg
1               5

<210> SEQ ID NO 182
<211> LENGTH: 7
<212> TYPE: PRT
<213> ORGANISM: Homo sapiens

<400> SEQUENCE: 182

Tyr Gly Asp Ala Leu Phe Ala
1               5

<210> SEQ ID NO 183
<211> LENGTH: 7
<212> TYPE: PRT
<213> ORGANISM: Homo sapiens

<400> SEQUENCE: 183

Ser Pro Gln Pro Phe Glu Glu
1               5

<210> SEQ ID NO 184
<211> LENGTH: 7
<212> TYPE: PRT
<213> ORGANISM: Homo sapiens

<400> SEQUENCE: 184

Gly Pro Gln Ser Gly Leu Gln
1               5

<210> SEQ ID NO 185
<211> LENGTH: 7
<212> TYPE: PRT
```

<213> ORGANISM: Homo sapiens

<400> SEQUENCE: 185

Leu Pro Leu Leu Asp Leu Asn
1               5

<210> SEQ ID NO 186
<211> LENGTH: 7
<212> TYPE: PRT
<213> ORGANISM: Homo sapiens

<400> SEQUENCE: 186

Gly Leu Pro Pro Tyr His Ser
1               5

<210> SEQ ID NO 187
<211> LENGTH: 7
<212> TYPE: PRT
<213> ORGANISM: Homo sapiens

<400> SEQUENCE: 187

Arg Pro Pro Ala Leu Ala Pro
1               5

<210> SEQ ID NO 188
<211> LENGTH: 7
<212> TYPE: PRT
<213> ORGANISM: Homo sapiens

<400> SEQUENCE: 188

Thr Asn Tyr Ala Val Asn Val
1               5

<210> SEQ ID NO 189
<211> LENGTH: 7
<212> TYPE: PRT
<213> ORGANISM: Homo sapiens

<400> SEQUENCE: 189

Ser Cys Thr Lys His Leu Cys
1               5

<210> SEQ ID NO 190
<211> LENGTH: 7
<212> TYPE: PRT
<213> ORGANISM: Homo sapiens

<400> SEQUENCE: 190

Ala Asn Thr Leu Arg Ser Pro
1               5

<210> SEQ ID NO 191
<211> LENGTH: 7
<212> TYPE: PRT
<213> ORGANISM: Homo sapiens

<400> SEQUENCE: 191

Ser Ser Phe Pro Pro Leu Leu
1               5

<210> SEQ ID NO 192
<211> LENGTH: 7
<212> TYPE: PRT
<213> ORGANISM: Homo sapiens

```
<400> SEQUENCE: 192

Val Ile Pro His Val Leu Ser
1               5

<210> SEQ ID NO 193
<211> LENGTH: 7
<212> TYPE: PRT
<213> ORGANISM: Homo sapiens

<400> SEQUENCE: 193

Thr Thr Gln Val Pro Ser Phe
1               5

<210> SEQ ID NO 194
<211> LENGTH: 7
<212> TYPE: PRT
<213> ORGANISM: Homo sapiens

<400> SEQUENCE: 194

His Ser Leu Ala Pro Thr Gln
1               5

<210> SEQ ID NO 195
<211> LENGTH: 7
<212> TYPE: PRT
<213> ORGANISM: Homo sapiens

<400> SEQUENCE: 195

Ser His Pro Ala Ser His Asp
1               5

<210> SEQ ID NO 196
<211> LENGTH: 7
<212> TYPE: PRT
<213> ORGANISM: Homo sapiens

<400> SEQUENCE: 196

Val Ser Pro Pro Ser Ser Tyr
1               5

<210> SEQ ID NO 197
<211> LENGTH: 7
<212> TYPE: PRT
<213> ORGANISM: Homo sapiens

<400> SEQUENCE: 197

His Phe Arg Ser Gly Ser Leu
1               5

<210> SEQ ID NO 198
<211> LENGTH: 7
<212> TYPE: PRT
<213> ORGANISM: Homo sapiens

<400> SEQUENCE: 198

Trp Thr Gly Ser Tyr Arg Trp
1               5

<210> SEQ ID NO 199
<211> LENGTH: 7
<212> TYPE: PRT
<213> ORGANISM: Homo sapiens

<400> SEQUENCE: 199
```

Gln Thr Ser Pro His Gly Lys
1               5

<210> SEQ ID NO 200
<211> LENGTH: 7
<212> TYPE: PRT
<213> ORGANISM: Homo sapiens

<400> SEQUENCE: 200

Ala Thr Pro Gln Pro Leu Pro
1               5

<210> SEQ ID NO 201
<211> LENGTH: 7
<212> TYPE: PRT
<213> ORGANISM: Homo sapiens

<400> SEQUENCE: 201

Ser Leu Thr Thr Leu Gly Ser
1               5

<210> SEQ ID NO 202
<211> LENGTH: 7
<212> TYPE: PRT
<213> ORGANISM: Homo sapiens

<400> SEQUENCE: 202

Tyr Ser Tyr Pro Arg Asp Ser
1               5

<210> SEQ ID NO 203
<211> LENGTH: 7
<212> TYPE: PRT
<213> ORGANISM: Homo sapiens

<400> SEQUENCE: 203

Ala Ser Phe Met Pro Leu Gln
1               5

<210> SEQ ID NO 204
<211> LENGTH: 7
<212> TYPE: PRT
<213> ORGANISM: Homo sapiens

<400> SEQUENCE: 204

Gly Pro Ser Val Arg Leu Gln
1               5

<210> SEQ ID NO 205
<211> LENGTH: 7
<212> TYPE: PRT
<213> ORGANISM: Homo sapiens

<400> SEQUENCE: 205

Leu Ala His Thr Leu Pro Leu
1               5

<210> SEQ ID NO 206
<211> LENGTH: 7
<212> TYPE: PRT
<213> ORGANISM: Homo sapiens

<400> SEQUENCE: 206

Val Gln Thr Pro Ala Arg Met
1               5

```
<210> SEQ ID NO 207
<211> LENGTH: 7
<212> TYPE: PRT
<213> ORGANISM: Homo sapiens

<400> SEQUENCE: 207

Gly Leu Ala Pro Arg Ser Ala
1               5

<210> SEQ ID NO 208
<211> LENGTH: 7
<212> TYPE: PRT
<213> ORGANISM: Homo sapiens

<400> SEQUENCE: 208

Phe Pro Trp Ser Leu Asp Gly
1               5

<210> SEQ ID NO 209
<211> LENGTH: 7
<212> TYPE: PRT
<213> ORGANISM: Homo sapiens

<400> SEQUENCE: 209

Ala His Thr Ser Ala Ile Pro
1               5

<210> SEQ ID NO 210
<211> LENGTH: 7
<212> TYPE: PRT
<213> ORGANISM: Homo sapiens

<400> SEQUENCE: 210

Ser His Val Pro Met Asn Pro
1               5

<210> SEQ ID NO 211
<211> LENGTH: 7
<212> TYPE: PRT
<213> ORGANISM: Homo sapiens

<400> SEQUENCE: 211

Tyr Met Asp Ser Thr Arg Arg
1               5

<210> SEQ ID NO 212
<211> LENGTH: 7
<212> TYPE: PRT
<213> ORGANISM: Homo sapiens

<400> SEQUENCE: 212

Ser Ser Leu Val Arg Thr Ala
1               5

<210> SEQ ID NO 213
<211> LENGTH: 7
<212> TYPE: PRT
<213> ORGANISM: Homo sapiens

<400> SEQUENCE: 213

Cys Trp Ala Met Leu Arg Asn
1               5
```

<210> SEQ ID NO 214
<211> LENGTH: 7
<212> TYPE: PRT
<213> ORGANISM: Homo sapiens

<400> SEQUENCE: 214

Ser Lys His His Ala Pro His
1               5

<210> SEQ ID NO 215
<211> LENGTH: 7
<212> TYPE: PRT
<213> ORGANISM: Homo sapiens

<400> SEQUENCE: 215

Thr Ser Gly Thr Pro Gln Leu
1               5

<210> SEQ ID NO 216
<211> LENGTH: 7
<212> TYPE: PRT
<213> ORGANISM: Homo sapiens

<400> SEQUENCE: 216

Lys Gln Thr Leu Pro Ser Ala
1               5

<210> SEQ ID NO 217
<211> LENGTH: 7
<212> TYPE: PRT
<213> ORGANISM: Homo sapiens

<400> SEQUENCE: 217

Thr Gln Asn Glu Val Arg Ser
1               5

<210> SEQ ID NO 218
<211> LENGTH: 7
<212> TYPE: PRT
<213> ORGANISM: Homo sapiens

<400> SEQUENCE: 218

Thr Phe Gln Tyr Val Ser Thr
1               5

<210> SEQ ID NO 219
<211> LENGTH: 7
<212> TYPE: PRT
<213> ORGANISM: Homo sapiens

<400> SEQUENCE: 219

His Val Val Lys Met Arg Gly
1               5

<210> SEQ ID NO 220
<211> LENGTH: 7
<212> TYPE: PRT
<213> ORGANISM: Homo sapiens

<400> SEQUENCE: 220

Thr Leu His Ser Leu Pro Pro
1               5

<210> SEQ ID NO 221
<211> LENGTH: 7

```
<212> TYPE: PRT
<213> ORGANISM: Homo sapiens

<400> SEQUENCE: 221

Ala Thr Leu Glu Met Pro Pro
1               5

<210> SEQ ID NO 222
<211> LENGTH: 7
<212> TYPE: PRT
<213> ORGANISM: Homo sapiens

<400> SEQUENCE: 222

Gln Ala His Thr Ile Ser Thr
1               5

<210> SEQ ID NO 223
<211> LENGTH: 7
<212> TYPE: PRT
<213> ORGANISM: Homo sapiens

<400> SEQUENCE: 223

Ala Leu Thr Pro Thr Pro Pro
1               5

<210> SEQ ID NO 224
<211> LENGTH: 7
<212> TYPE: PRT
<213> ORGANISM: Homo sapiens

<400> SEQUENCE: 224

Ala Ser Pro Ile Thr Lys Phe
1               5

<210> SEQ ID NO 225
<211> LENGTH: 7
<212> TYPE: PRT
<213> ORGANISM: Homo sapiens

<400> SEQUENCE: 225

Phe Val Asn Pro Leu Ser Pro
1               5

<210> SEQ ID NO 226
<211> LENGTH: 7
<212> TYPE: PRT
<213> ORGANISM: Homo sapiens

<400> SEQUENCE: 226

Lys Pro Ala Tyr Pro Pro His
1               5

<210> SEQ ID NO 227
<211> LENGTH: 7
<212> TYPE: PRT
<213> ORGANISM: Homo sapiens

<400> SEQUENCE: 227

Tyr Pro Pro His Gly Val Val
1               5

<210> SEQ ID NO 228
<211> LENGTH: 7
<212> TYPE: PRT
<213> ORGANISM: Homo sapiens
```

<400> SEQUENCE: 228

Ser Gln Pro Ile Glu Asn Lys
1               5

<210> SEQ ID NO 229
<211> LENGTH: 7
<212> TYPE: PRT
<213> ORGANISM: Homo sapiens

<400> SEQUENCE: 229

Thr Ile Glu Gln His Pro Pro
1               5

<210> SEQ ID NO 230
<211> LENGTH: 7
<212> TYPE: PRT
<213> ORGANISM: Homo sapiens

<400> SEQUENCE: 230

Ala Gly Ala Leu His Gln Phe
1               5

<210> SEQ ID NO 231
<211> LENGTH: 7
<212> TYPE: PRT
<213> ORGANISM: Homo sapiens

<400> SEQUENCE: 231

Gln His Pro Ala Lys Thr Ala
1               5

<210> SEQ ID NO 232
<211> LENGTH: 7
<212> TYPE: PRT
<213> ORGANISM: Homo sapiens

<400> SEQUENCE: 232

Ala Ser Thr Leu Lys Trp Ala
1               5

<210> SEQ ID NO 233
<211> LENGTH: 7
<212> TYPE: PRT
<213> ORGANISM: Homo sapiens

<400> SEQUENCE: 233

Ser Ser Val Trp His Ser Thr
1               5

<210> SEQ ID NO 234
<211> LENGTH: 7
<212> TYPE: PRT
<213> ORGANISM: Homo sapiens

<400> SEQUENCE: 234

Ala Pro Ala Leu Phe Pro Ile
1               5

<210> SEQ ID NO 235
<211> LENGTH: 7
<212> TYPE: PRT
<213> ORGANISM: Homo sapiens

<400> SEQUENCE: 235

Gly Pro His Met Trp Leu Val
1               5

<210> SEQ ID NO 236
<211> LENGTH: 7
<212> TYPE: PRT
<213> ORGANISM: Homo sapiens

<400> SEQUENCE: 236

Asn His Asp Tyr Val Thr Trp
1               5

<210> SEQ ID NO 237
<211> LENGTH: 7
<212> TYPE: PRT
<213> ORGANISM: Homo sapiens

<400> SEQUENCE: 237

Ser Asn Arg Phe Glu Gln Gln
1               5

<210> SEQ ID NO 238
<211> LENGTH: 7
<212> TYPE: PRT
<213> ORGANISM: Homo sapiens

<400> SEQUENCE: 238

Thr Asn Ser Glu Arg Ile His
1               5

<210> SEQ ID NO 239
<211> LENGTH: 7
<212> TYPE: PRT
<213> ORGANISM: Homo sapiens

<400> SEQUENCE: 239

Ala Ala Thr Leu Phe Pro Leu
1               5

<210> SEQ ID NO 240
<211> LENGTH: 7
<212> TYPE: PRT
<213> ORGANISM: Homo sapiens

<400> SEQUENCE: 240

Ser Leu Leu Gly Gln Thr Pro
1               5

<210> SEQ ID NO 241
<211> LENGTH: 7
<212> TYPE: PRT
<213> ORGANISM: Homo sapiens

<400> SEQUENCE: 241

Val Pro Ala Trp Ala Gly His
1               5

<210> SEQ ID NO 242
<211> LENGTH: 7
<212> TYPE: PRT
<213> ORGANISM: Homo sapiens

<400> SEQUENCE: 242

Thr Val Ala Pro Ser Ala Asn

```
1               5

<210> SEQ ID NO 243
<211> LENGTH: 7
<212> TYPE: PRT
<213> ORGANISM: Homo sapiens

<400> SEQUENCE: 243

Thr Thr Met Pro Tyr Ile Ala
1               5

<210> SEQ ID NO 244
<211> LENGTH: 7
<212> TYPE: PRT
<213> ORGANISM: Homo sapiens

<400> SEQUENCE: 244

Asn Pro Pro Ser Arg His Pro
1               5

<210> SEQ ID NO 245
<211> LENGTH: 7
<212> TYPE: PRT
<213> ORGANISM: Homo sapiens

<400> SEQUENCE: 245

Trp Ala Pro Trp Ser Pro Ala
1               5

<210> SEQ ID NO 246
<211> LENGTH: 7
<212> TYPE: PRT
<213> ORGANISM: Homo sapiens

<400> SEQUENCE: 246

Thr Pro Gln Arg Asp Leu Arg
1               5

<210> SEQ ID NO 247
<211> LENGTH: 7
<212> TYPE: PRT
<213> ORGANISM: Homo sapiens

<400> SEQUENCE: 247

Lys Phe Pro Met Pro Gln Tyr
1               5

<210> SEQ ID NO 248
<211> LENGTH: 7
<212> TYPE: PRT
<213> ORGANISM: Homo sapiens

<400> SEQUENCE: 248

Ser Glu Ser Thr Gly Thr Phe
1               5

<210> SEQ ID NO 249
<211> LENGTH: 7
<212> TYPE: PRT
<213> ORGANISM: Homo sapiens

<400> SEQUENCE: 249

Leu Ser Met Thr Gly Arg Asp
1               5
```

```
<210> SEQ ID NO 250
<211> LENGTH: 7
<212> TYPE: PRT
<213> ORGANISM: Homo sapiens

<400> SEQUENCE: 250

Met Thr Ala Ala Pro Val His
1               5

<210> SEQ ID NO 251
<211> LENGTH: 7
<212> TYPE: PRT
<213> ORGANISM: Homo sapiens

<400> SEQUENCE: 251

Glu Arg Ala Pro Met Gln Ser
1               5

<210> SEQ ID NO 252
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = beta-alanine

<400> SEQUENCE: 252

Xaa Lys Thr Leu Leu Pro Thr Pro Gly Gly Ser Lys Lys Lys
1               5                   10

<210> SEQ ID NO 253
<211> LENGTH: 9
<212> TYPE: PRT
<213> ORGANISM: Homo sapiens

<400> SEQUENCE: 253

Thr Glu Val His His His His His His
1               5

<210> SEQ ID NO 254
<211> LENGTH: 22
<212> TYPE: PRT
<213> ORGANISM: Homo sapiens

<400> SEQUENCE: 254

His His His His His His Lys Lys Lys Gly Gly Ser Gly Ser Thr Glu
1               5                   10                  15

Val Gly Gly Ser Gly Ser
            20

<210> SEQ ID NO 255
<211> LENGTH: 7
<212> TYPE: PRT
<213> ORGANISM: Homo sapiens

<400> SEQUENCE: 255

Ala Ser Pro Ile Thr Lys Phe
1               5
```

TARGET-SPECIFIC DELIVERY OF THERAPEUTIC AGENTS

CLAIM OF PRIORITY

This application is a U.S. National Stage Filing under 35 U.S.C. 371 from International Application No. PCT/US2016/037668, filed on 15 Jun. 2016, and published as WO 2016/205397, which claims the benefit of priority of U.S. Provisional Patent Application No. 62/175,922, filed on 15 Jun. 2015, the benefit of priority of which are claimed hereby, and which are incorporated by reference herein in their entirety.

GOVERNMENT GRANT SUPPORT

This invention was made with government support under HL115225 awarded by the National Institutes of Health. The government has certain rights in the invention.

BACKGROUND OF THE INVENTION

Coronary artery disease (CAD) is the leading cause of morbidity and mortality in developed countries and is responsible for 1 in 6 deaths in the United States. Roughly 34% of people who have a myocardial infarction (MI) will die acutely from it (1), however, within 5 years, 25% of patients will succumb due to downstream pathologies resulting from the MI (2). After reperfusion of ischemic myocardium, the left ventricle (LV) undergoes a progressive physiological and anatomical transformation (LV remodeling) (3). While necessary to reverse ischemia, reperfusion nevertheless provokes an acute pro-inflammatory phase characterized by chemokine signaling and infiltration of the neutrophils that are necessary to clear necrotic cardiomyocytes and cellular debris from the infarct zone. In mice, this is followed 2-3 days later by the start of the proliferative phase (lasting some 3-4 days) during which monocytes invade the infarct zone and differentiate into macrophages (4). The final phase involves apoptosis of myofibroblasts, regression of neovessels from the infarct zone and maturation of the collagen-based matrix into mature scar (5). In the end, LV remodeling alters left ventricular geometry from an ellipse to a more spherical structure—with negative effects on cardiac function (5). During these phases, multiple cellular and molecular events occur within the various cell types present in the post-ischemic myocardium (6, 7) each of which influence the overall outcome of LV remodeling.

SUMMARY OF THE INVENTION

Although reperfusion aids in restoring circulation to ischemic myocardium, it also leads to irreversible events including reperfusion injury, decreased cardiac function and ultimately scar formation. Various cell types are involved in the multi-phase repair process including inflammatory cells, vascular cells and cardiac fibroblasts. Therapies targeting these cell types in the infarct border zone can improve cardiac function, but are limited by systemic side effects. The instant invention provides liposomes with surface modifications to include peptides with affinity for cell types present in the post-infarct myocardium. To identify peptides specific for the infarct/border zone, in vivo phage display methods and an optical imaging approach, fluorescence molecular tomography (FMT), were utilized. Peptides were identified specific for cardiomyocytes, endothelial cells, myofibroblasts, and c-Kit[+] cells present in the border zone of the remodeling infarct. These peptides were then conjugated to liposomes and in vivo specificity and pharmacokinetics were determined. As a proof of concept, cardiomyocyte specific (I-1) liposomes were used to deliver a PARP-1 (Poly [ADP-ribose] polymerase 1) inhibitor: AZ7379. A targeted liposomal approach was able to increase AZ7379 availability in the infarct/border zone at 24 h post-injection as compared to free AZ7379. A ~3-fold higher efficiency of PARP-1 inhibition was observed when all cell types were assessed using I-1 liposomes as compared to negative control peptide liposomes (NCP). When analyzed further, I-1 liposomes had a 9-fold and 1.5-fold higher efficiency in cardiomyocytes and macrophages, respectively, as compared to NCP liposomes. In conclusion, a modular drug delivery system has been developed that can be targeted to cell types of therapeutic interest in the infarct border zone.

The invention provides pharmaceutical compositions and method of using the compositions, wherein the compositions comprise one or more targeting peptides and/or a payload, such as a gene, protein or drug, and optionally a delivery vehicle, such as liposomes or micelles.

On embodiment provides an isolated peptide comprising the amino acid sequence selected from peptides in Table 1 or wherein the peptide has one 1 or more conservative amino acid substitutions, deletions or additions as compared to a peptide of Table 1. In on embodiment, one or more of the amino acids of the peptide are D-amino acids. In another embodiment, the peptide is conjugated to a payload. In one embodiment, the payload is conjugated to the peptide directly or indirectly, such as with the use of one or more linkers and/or spacers. One embodiment provides a delivery vehicle, such as a liposome. In one embodiment, the payload is encapsulated by the delivery vehicle. In another embodiment, the peptide is associated covalently or non-covalently with the delivery vehicle.

One embodiment provides a composition comprising one or more of the peptides described herein and a pharmaceutically acceptable carrier.

One embodiment provides a method of delivering a payload to cardiovascular tissue or cell of a subject in need thereof comprising administering to the subject a peptide or the composition described herein, wherein the peptide targets the payload to the cardiovascular tissue or cell thereby delivering the payload to the cardiovascular tissue or cell. In one embodiment, the administration is systemic. In another embodiment, the peptide is selective for ischemic and/or peri-infarct region of mammalian cardiovascular tissue.

One embodiment provides a method of treating a cardiomyopathy in a subject comprising: administering systemically to a subject in need thereof an effective amount of a peptide or the composition described herein, wherein the effective amount is effective to cause functional improvement in at least one of the following parameters: left ventricular volume, left ventricular area, left ventricular dimension, cardiac function, 6-minute walk test, or New York Heart Association (NYHA) functional classification.

One embodiment provides a method of delivering a payload to a cardiovascular cell comprising contacting said cell with a peptide or composition as described herein.

Another embodiment provides a method of treating a cardiovascular disease or disorder comprising administering to a subject in need thereof an effective amount of a peptide or the composition described herein, wherein the effective amount treats the disease or disorder.

One embodiment provides for a composition comprising two or more peptides having different amino acid sequences.

One embodiment provides a composition comprising two or more payloads (optionally two or more peptides having different amino acid sequences). In one embodiment, the two or more payloads are therapeutic agents and imaging agents. In one embodiment each payload is delivered to a different cell type. In another embodiment, the different cell types are located within the same tissue.

One embodiment provides an isolated and purified peptide comprising the amino acid sequence selected from the peptides in Table 1 or wherein the peptide has one 1 or more conservative amino acid substitutions, deletions or additions as compared to a peptide provided in Table 1. Another embodiment provides a composition comprising a delivery vehicle, a cardiac targeting peptide and a payload. In one embodiment, the delivery vehicle is a liposome. In another embodiment, the payload is a drug, radioisotope or contrast agent.

One embodiment provides a method of delivering a therapeutic agent to cardiac tissue of a subject in need thereof comprising administering to the subject a delivery vehicle, the delivery vehicle comprises a polymeric carrier and a therapeutic agent, wherein the delivery vehicle is conjugated to a cardiac tissue targeting peptide, wherein the peptide targets the delivery vehicle to cardiac tissue thereby delivery a therapeutic agent to cardiac tissue. In one embodiment, the delivery vehicle is administered systemically. In another embodiment, cardiac tissue targeting peptide is selective for a weakened, ischemic, and/or peri-infarct region of mammalian cardiac tissue. In one embodiment, the delivery vehicle is a liposome. In another embodiment, the therapeutic agent is encapsulated by the liposome.

One embodiment provides a method of treating a cardiomyopathy in a subject comprising administering systemically to a subject in need thereof a therapeutically effective amount of liposomes, wherein the liposome is conjugated to a cardiac tissue targeting peptide of described herein and comprises a payload, wherein the therapeutically effective amount of liposomes is effective to cause functional improvement in at least one of the following parameters: left ventricular strain, left ventricular volume, left ventricular area, left ventricular dimension, cardiac function, 6-minute walk test, or New York Heart Association (NYHA) functional classification. One embodiment provides a delivery vehicle and at least one cardiac targeting peptide described herein. In one embodiment, the delivery vehicle is a liposome. In another embodiment, the delivery vehicle further comprises at least one payload.

One embodiment provides a method of delivering a payload to a cardiac cell in a patient or of treating a cardiac disease or disorder comprising administering to a cell or a subject in need of cardiac therapy an effective amount of a payload by use of liposome comprising a payload-conjugated lipid or encapsulated payload, wherein the liposome further comprises at least one cardiac targeting peptide described herein, wherein the drug is effective for treating the disease or disorder, and wherein the composition is taken up by cardiac cells, the composition releases the payload to the cells, and the cells are thereby treated.

BRIEF DESCRIPTION OF THE DRAWINGS

FIGS. 2A-F depict phage clones specific for four cell types of interest in the border zone. Immunohistochemistry with antibodies against cell-type specific markers was used to identify phage clones specific for: A) endothelial cells (B-40 phage), B myofibroblasts (B-29 phage), C) extracellular matrix (B-11 phage), D) cardiomyocytes (I-1 phage), and E) c-Kit$^+$ cells (B-50 phage). White arrowheads point to phage clones co-localized with cell types of interest. (Scale bar; 20 μm).

FIGS. 4A-F depict immunofluorescence of peptide conjugated liposomes in post-MI hearts. A) NCP was nonspecifically taken up by macrophages of remodeling infarct. Peptides identified in the phage screen were specific for cellular targets present in the border zone: B) Peptide I-1 was specific or cardiomyocytes (caveolin-3, arrow), C) B-40 specific for endothelial cells (CD31, arrow), D) B-50 specific for c-Kit+ cells (c-Kit, arrow), and E) B-29 specific for myofibroblasts (DDR2, arrow). Peptides are pseudocolored green and cell markers (mac-2, caveolin-3, CD31, c-Kit, DDR2) blue (scale bar; 20 μm). F) Peptide specificity for the corresponding cell types was analyzed using the ImageJ plug-in JACoP. (* indicates p<0.01), (** indicates p<0.05).

FIGS. 5A-D depict remote loading and release of AZ7379 from I-1 conjugated liposomes. A) Structure of AZ7379

Figure 1A:
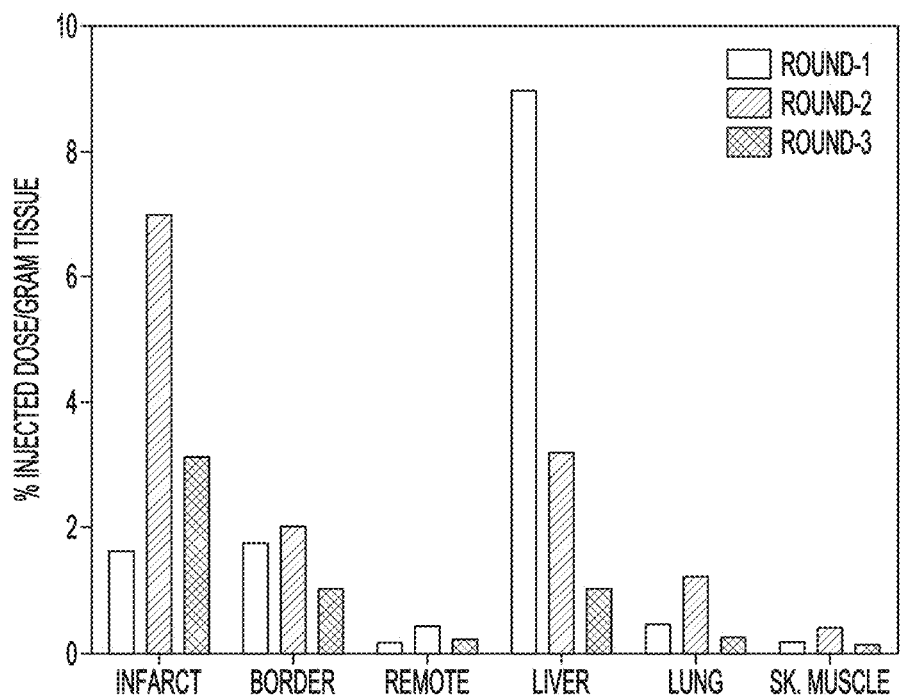
FIGS. 1A-F depict in vivo phage display screen in post-MI mice and determination of phage clone specificity for the post-infarct heart using FMT. A) Phage pools (reported as percent injected dose per gram tissue) that were recovered from 3 different regions of the heart, as well as liver, lungs and skeletal muscle. B) Heart:Liver VT680 ratios of negative control (NC) phage compared to the round-3 amplified phage pool shows clear evidence of specificity for the post-infarct heart by FMT. C) Heat map showing the specificity ratios (heart:liver VT 680/heart:liver VT750) at 0.25 and 4 h post-injection of phage groups from FMT imaging. D) Heat map showing the specificity (heart:liver VT 680/heart:liver VT750) at 0.25 and 4 h post-injection of phage clones from high specificity groups from FMT imaging. E) Graphic representation of phage group specificity ratios from FMT images obtained at 0.25 and 4 h post-injection. F) Graphic representation of individual phage clone specificity ratios from FMT images obtained at 0.25 and 4 h post-injection. Insets in F) show FMT images of mice injected with negative control (NC) phage and B-40 phage at 4 h post-injection followed by ex-vivo imaging of heart showing enhanced VT680 signal in the infarct zone.

(provided by AstraZeneca). B) Physiochemical properties of AZ7379 as provided by a: ACD/Labs, b: Marvin, c: AstraZeneca. C) Table showing characteristics of peptide and drug per liposome in NCP and I-1 targeted formulations. D) Release of AZ7379 in 50% fetal bovine serum over time from liposomes formulated using DOPC, DPPC or DSPC as phosphatidyl choline. DOPC showed slower release kinetics than DPPC or DSPC.

FIGS. 6A-E depict PAR production in cardiomyocytes after targeted delivery of AZ7379. Schematic of PAR PD study using empty I-1 liposomes (drug free), free AZ7379, NCP liposomes loaded with AZ7379 and I-1 liposomes loaded with AZ7379 (n=5). PAR was induced 24 h post-injection by incubating heart slices in saline for 90 min. PAR was immunostained along with cardiomyocytes stained for the marker caveolin-3 DAPI. (B) PAR was expressed in cardiomyocytes (white arrow) and phagocytes (white arrowhead) in tissues with empty I-1 liposomes. (C) PAR was expressed in cardiomyocytes (white arrow) and not in phagocytes (white arrowhead) in tissues with NCP AZ7379 liposomes. (D) PAR was occasionally seen in cardiomyocytes (white arrow, punctate signal) and phagocytes (white arrowhead) in tissues with I-1 AZ7379 liposomes. (Scale bar; 20 μm). (E) Graph showing the percent PAR+cardiomyocytes and phagocytes as assessed by quantitative image analysis. Percentage of PAR+cardiomyocytes in NCP and I-1 AZ7379 loaded liposomes was 4 and 0.46 respectively. (* indicates p<0.01).

FIGS. 7A-E depict phage screen validation. A) FMT quantification in the heart region of post-MI mice injected with negative control (NC) phage or round-3 amplified phage over time post-injection. B) Ex vivo quantification of NC and round-3 applied phage within multiple organs isolated at 7 and 24 h post-injection. C) Ex vivo FMT images of hearts and livers from two example mice at 7 and 24 h post-injection. D) Phage clones were segregated into 23 groups of four clones/group based on phylogeny and sequence similarity. Clones in red were then excluded as rapid amplifiers. Three duplicate clones were identified and represented by "X/Y". E) The group-level screen was carried out on day 4 post-MI mice and each group was normalized to the negative control phage (panc-27).

FIGS. 8A-G depict B-40 and B-50 phage binding to endothelial and c-Kit+cells, respectively, on day 4 post-MI. A) B-40 phage bound to endothelial cells of microvessels present in the infarct border zone. B) B-50 phage bound to c-Kit+cells that were CD45—indicating that these c-Kit+ cells are not blood-borne cells. C) B-50 phage bound to c-Kit+cells and about 10% of these c-Kit+cells were also Sca-1+ indicating that these cells are potentially stem cells. D) The c-Kit+cells were also CD105+, further implicating them as stem cells. E) B-29 phage bound to myofibroblasts (aSMA+) isolated from Day 4 post-MI hearts. F) The binding of B-50 to c-Kit+cells was verified by flow cytometry using cells isolated from the post-infarct heart and bone marrow from day 4 post-MI mice. B-50 phage bound to c-Kit+cells from MI heart and bone marrow. G) The specificity of I-1 phage for cardiomyocytes was compared with negative control phage (NCP) for their binding to cardiomyocytes (RL-14) and control cells (SKOV3) by flow cytometry. (Scale bar; 20 μm).

FIGS. 9A-D depict characterization of peptide-conjugated liposomes. Liposomes in three batches were prepared by saline hydration of lipid mixtures containing peptide-PEG-DSPE. The resulting solution was passed through a 0.2 μm filter 41 times and the size and concentration of liposomes was measured using a Nanosight NS300. The peptide was synthesized with a linker sequence containing a lysine residue chemically conjugated to the fluorophore FAM. The presence of this fluorophore enabled determination of the number of peptides that were incorporated into each of the liposome preparations. B-D) The Specificity of peptide-conjugated liposomes for the post-infarct heart was studied from liposomes prepared in three batches. Pharmacokinetics of peptide conjugated liposomes from three batches showed similar profile even though they had slight variable number of peptides per liposome and the concentration.

Figure 10A:
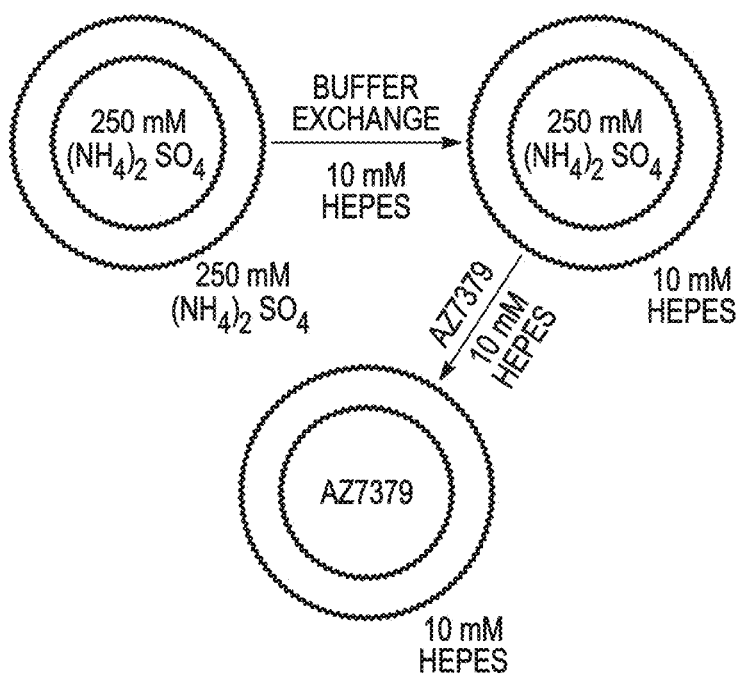
Figure 10B:
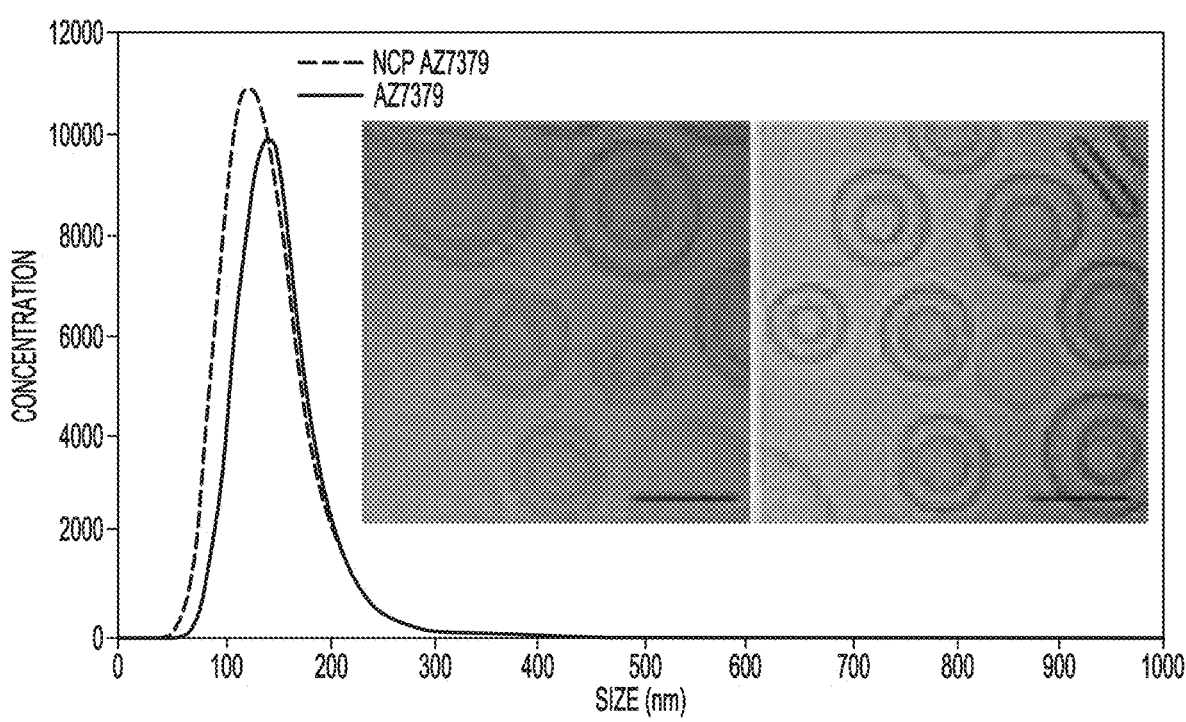

FIGS. 10A-B depict remote loading and characterization of I-1 liposomes loaded with AZ7379. A) A cartoon showing the remote loading procedure that was used to load AZ7379 into NCP and I-1 liposomes. B) Remote loaded NCP and I-1 were characterized using Nanosight to determine their size and concentration followed by cryoTEM to characterize their structure. The inset at left in panel (B) shows the structure of I-1 liposomes before remote loading while the inset at right shows liposomes after remote loading. (Scale bar; 100 nm).

FIGS. 11A-D depict pharmacodynamic measurement in cardiomyocytes and phagocytes. PAR+ cells analyzed by immunofluorescence in A) caveolin-3+ cardiomyocytes or B) mac-2+ phagocytes. (PAR-red, cardiomyocytes or phagocytes-green). Pharmacodynamic measurement using cardiomyocyte-specific liposomes in comparison with empty and non-targeted liposomes. C) PAR+ cells were analyzed by immunofluorescence and are reported here as the percent of PAR+ cells seen in caveolin-3 positive cardiomyocytes and galectin-3 (mac-2) positive phagocytes (primarily macrophages). D) Cardiomyocyte-specific (I-1) liposomes were conspicuously absent from the remote region (liposomes-red, cardiomyocytes-yellow and nuclei-white). (Scale bar; 20 μm).

Figure 12A:
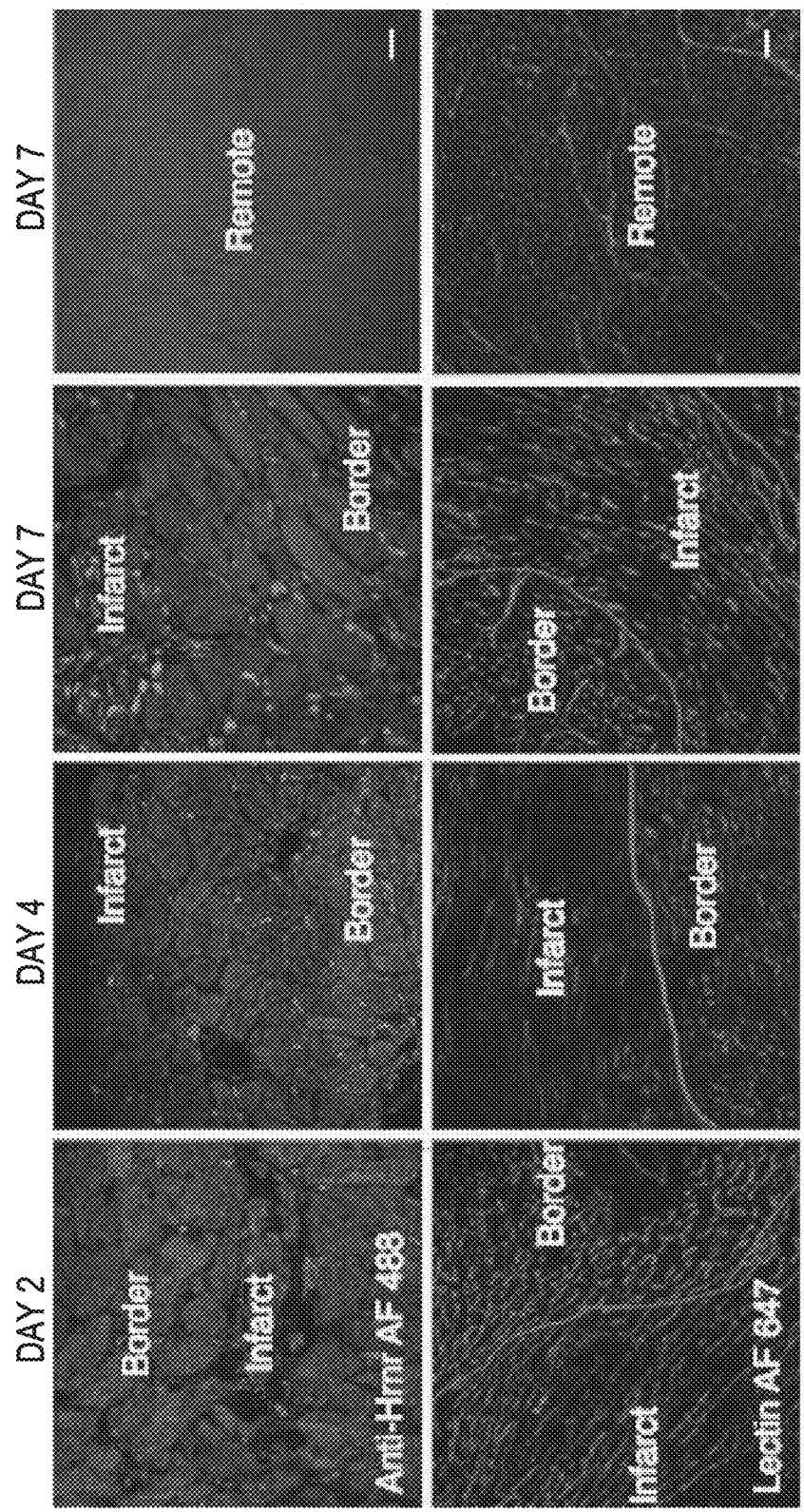
Figure 12B:
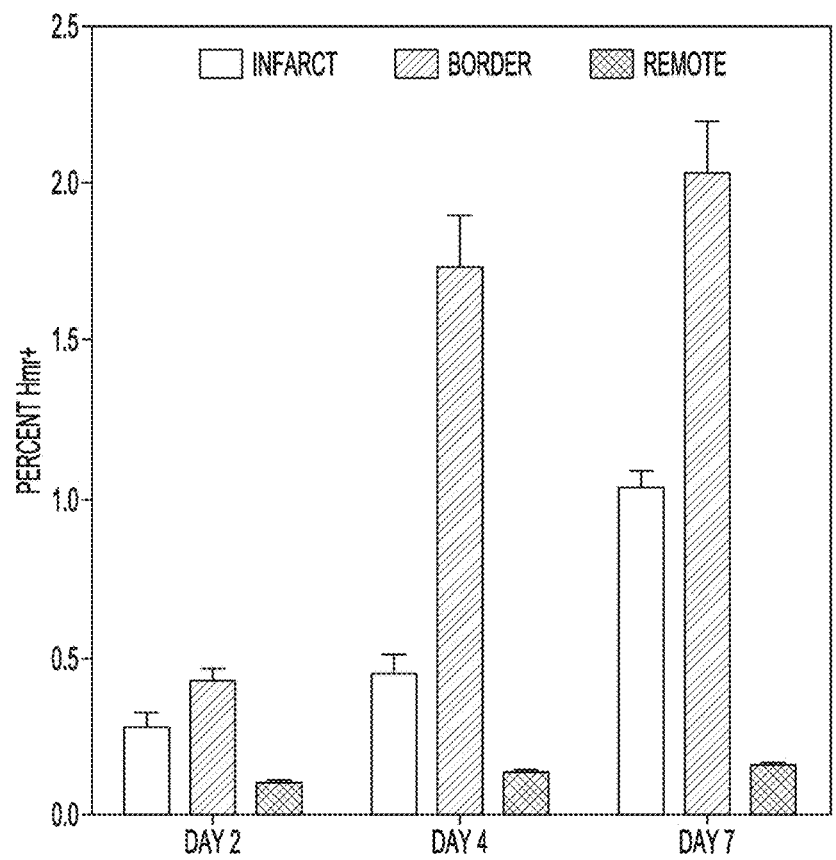
Figure 12C:
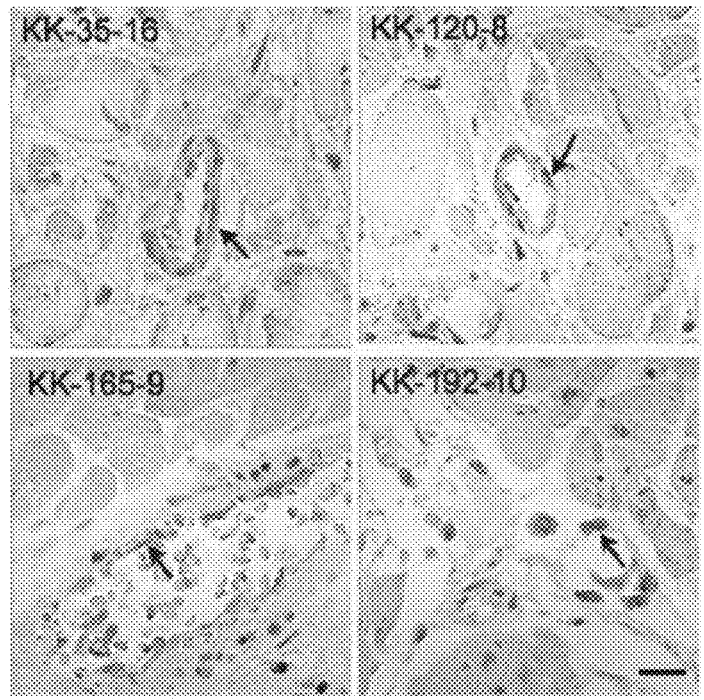

FIGS. 12A-C depict hornerin expression in post-infarct mice and human hearts. A) Hornerin immunostaining was carried out on days 2, 4 and 7 post-MI along with staining of vessels with lectin-AF 647 (pseudo-colored in blue). Hornerin expression increases after infarction and peaks at day 7 post-MI, corresponding to the end of neo-angiogenesis. B) Hornerin staining was quantified using ImageJ in the infarct, border and remote regions of LV at 3 different time points post-MI. C) Hornerin staining was also performed in human autopsy specimens (4 samples) from unidentified patients now deceased due to MI. Strong hornerin signals were detected almost exclusively in endothelial cells located in the infarct border zone (Scale bar; 20 μm).

FIGS. 13A-D depict B-40 phage and liposomes in the infarct border region. A) Immunofluorescence of B-40 phage and C) B-40 liposomes in the infarct border zone 24 h post injection. B-40 phage and peptide and liposomal DiR were specific for border zone endothelial cells but were rarely detected in the remote region. (B&D, scale bar; 20 μm).

Figure 14A:
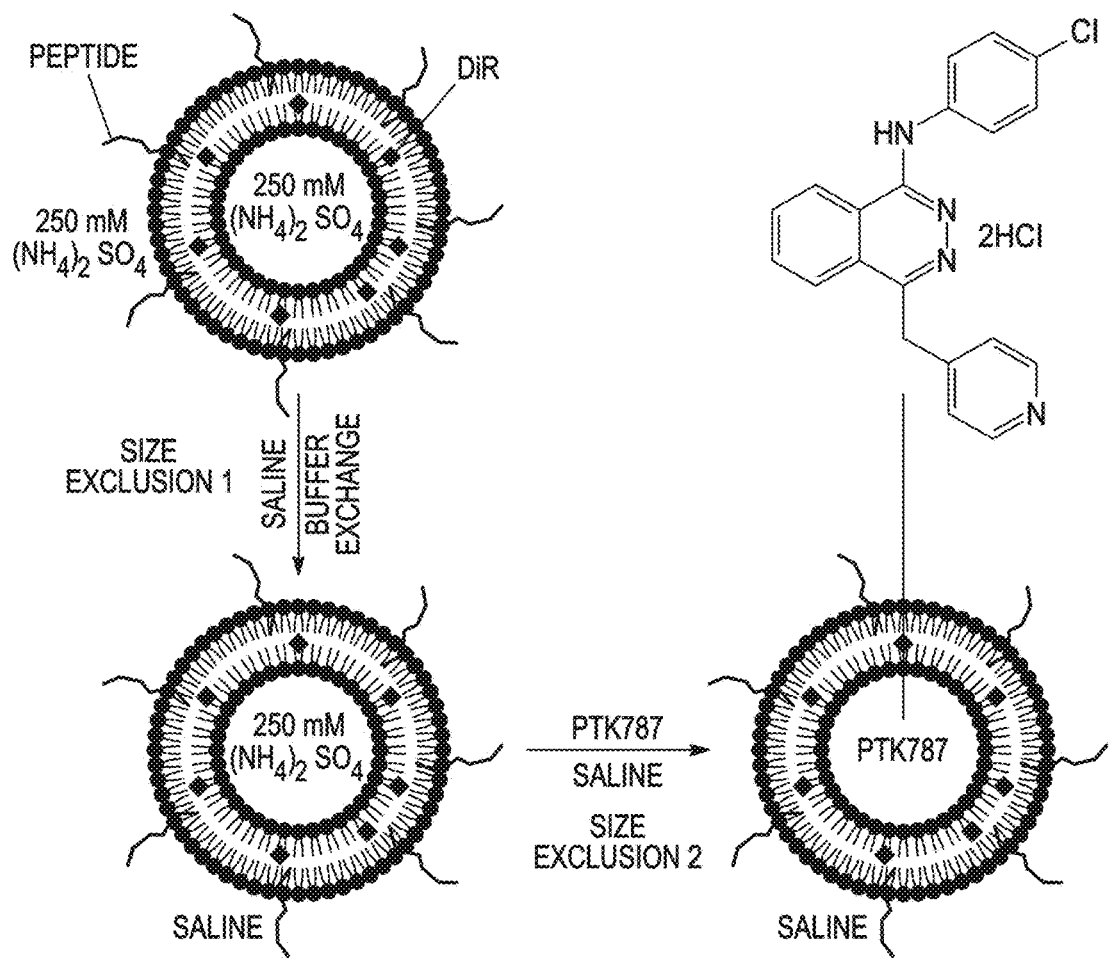
Figure 14B:
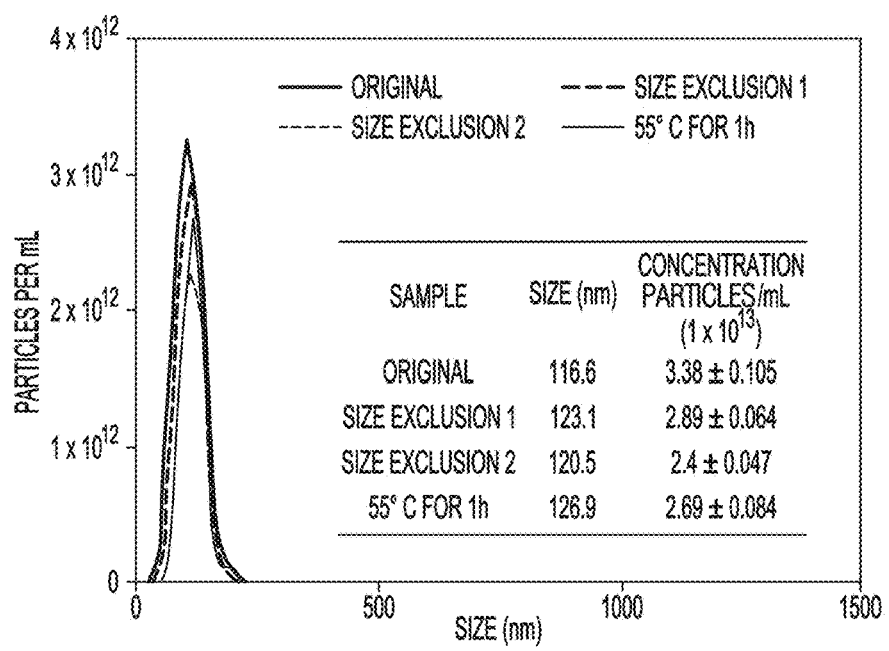

FIGS. 14A-B depict remote loading of PTK787 and Nanosight characterization of liposomes. A) Cartoon showing the procedure used to remote load B-40 liposomes with PTK787. B) Nanosight characterization of B-40 liposomes at various stages of remote loading procedure. The graph shows the concentration vs. size distribution of liposomes at various steps of the remote loading procedure. The tabular inset shows the size and concentration of the liposomes during remote loading.

FIGS. 15A-G show measure of vessel volume fraction following liposomal delivery of PTK787. A) Experimental design for measuring neovessel formation resulting from the delivery of empty B-40 liposomes (drug free), free PTK787

(20 and 100 mg/kg-day), I-1 liposomes loaded with PTK787 and B-40 liposomes loaded with PTK787 (6 and 10 mg/kg-day) (n=4 per group). Vessel volume fraction (VVF) was measured on day 7 post-MI after using in vivo lectin staining to label neovessels prior to tissue harvest. Using whole mount sections, confocal microscopy was performed to measure VVF in the infarct, border and remote regions. Confocal images showing vessels stained with lectin AF 647 (pseudo colored green) from B) control, C) free PTK787 (20 mg/kg-day), D) free PTK787 (100 mg/kg-day), E) I-1 liposomes loaded with PTK787 (10 mg/kg-day), F) B-40 liposomes loaded with PTK787 (10 mg/kg-d) and G) B-40 liposomes loaded with PTK787 (6 mg/kg-day) (Scale bar; 100 μm)

Figure 16A:
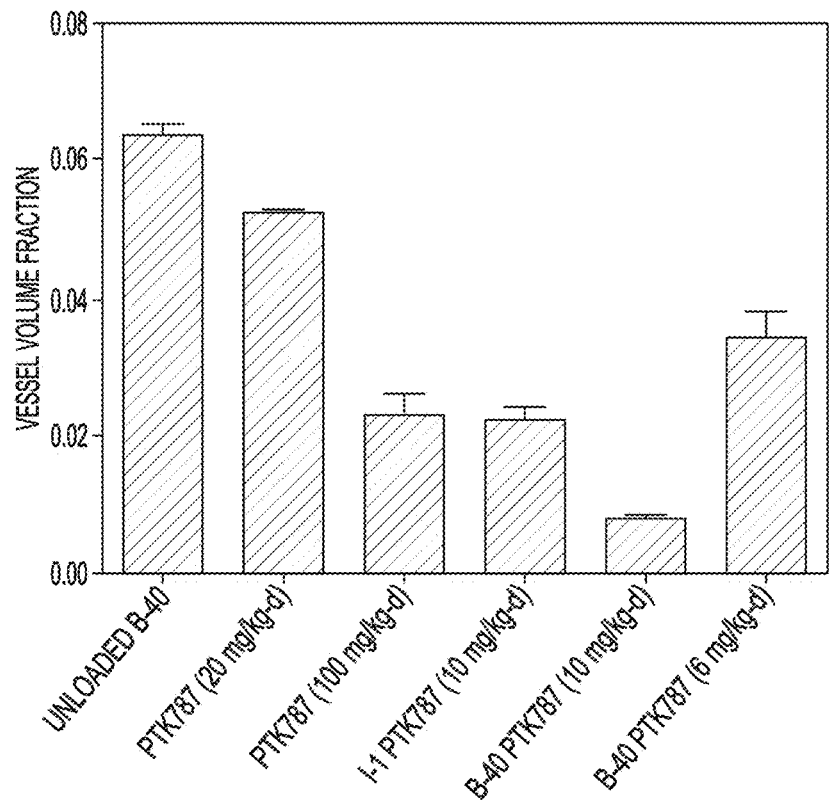
Figure 16B:
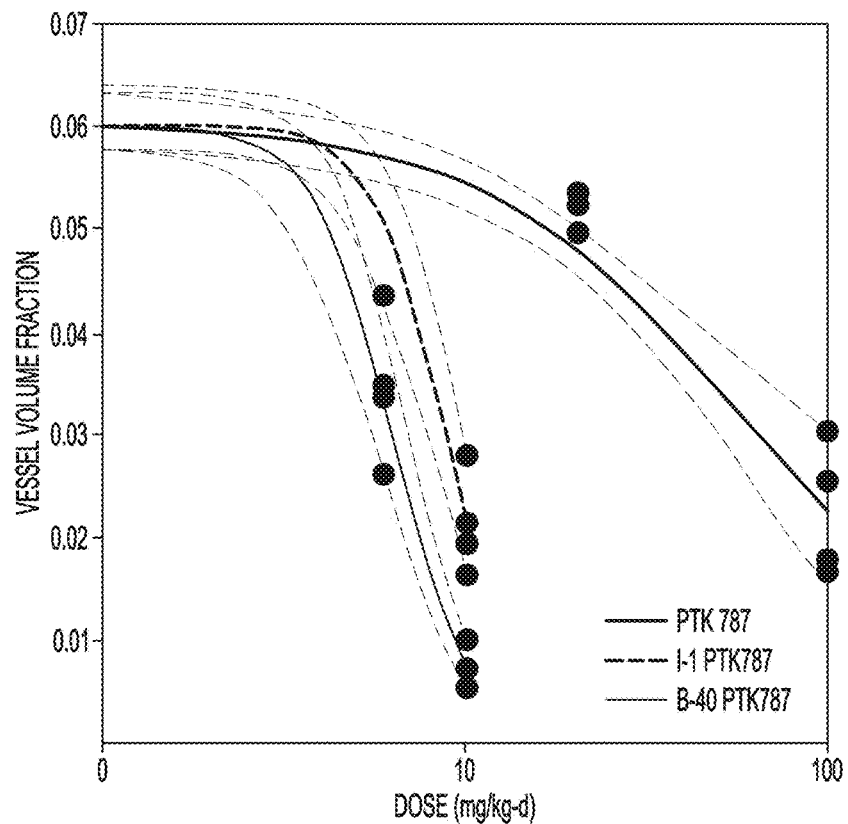

FIGS. 16A-B depict vessel volume fraction following endothelial specific delivery of PTK787. A) Using the RAVE program, vessel volume fraction was calculated and results indicate that B-40 liposomes (10 mg/kg-d) were significantly more effective at preventing neovessel formation (VVF-0.008) in the infarct region as compared to any other dose or formulation, including free PTK787 at a 10-fold higher dose 100 mg/kg-d and I-1 PTK ($p<0.05$). B) Using Imax modeling, ED50 values were determined for free PTK787 from doses of 20 & 100 mg/kg-d (in gray), I-1 (cardiomyocyte-targeted) liposomes with PTK787 from a dose of 10 mg/kg-d, and B-40 liposomes from doses of 6 & 10 mg/kg-d. The solid lines indicate median values and the dashed lines indicate the 95th and 5th percentile model fits obtained from 1,000 nonparametric bootstrap data sets.

Figure 17:
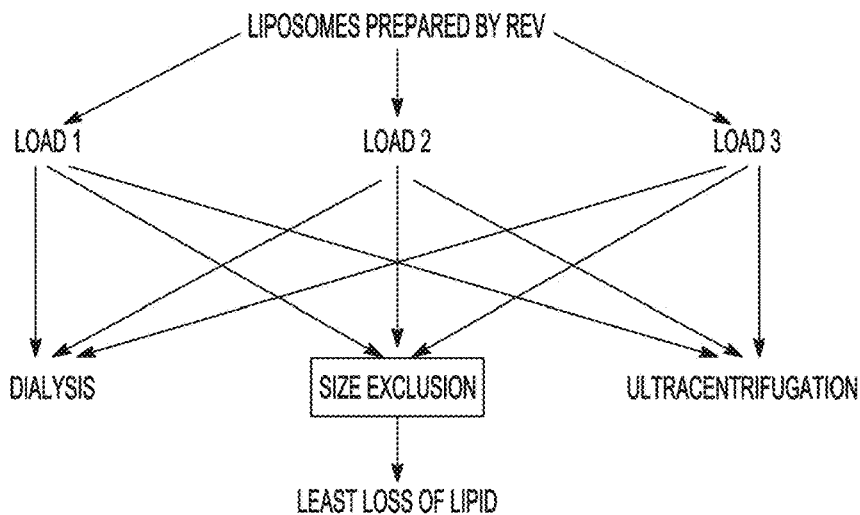

FIG. 17 depicts different methods to separate liposomes and free AZ7379 after remote loading. Liposomes were prepared by REV process containing 0.25M ammonium sulfate solution. To remove ammonium sulfate from the exterior of the liposomes, either dialysis, size exclusion and ultracentrifugation was carried out. Similarly the free AZ7379 was removed and the final drug to lipid ratio was calculated using HPLC. We observed that lipid was lost significantly during in dialysis and ultracentrifugation methods, but not with the size exclusion method.

Figure 18:
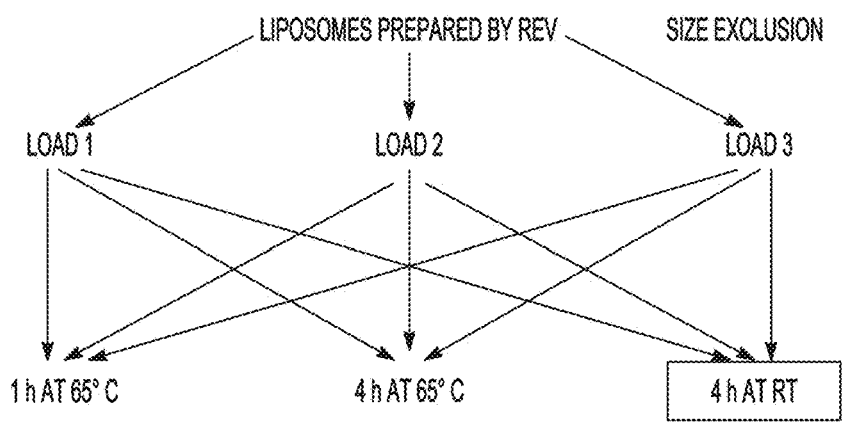

FIG. 18 depicts identifying the ideal conditions for remote loading AZ7379. Liposomes were prepared by REV process containing 0.25M ammonium sulfate solution. To remove ammonium sulfate from the exterior of the liposomes, size exclusion was carried out as this had the least loss of lipid. Remote loading was carried out by incubating the AZ7379 and liposomes either at 65° C. for 1 h or 65° C. for 4 h or at RT for 4 h. Based on the HPLC quantification, it was identified that incubating AZ7379 and liposomes at RT for 4 h was ideal with the best final drug to lipid ratio.

Figure 19:
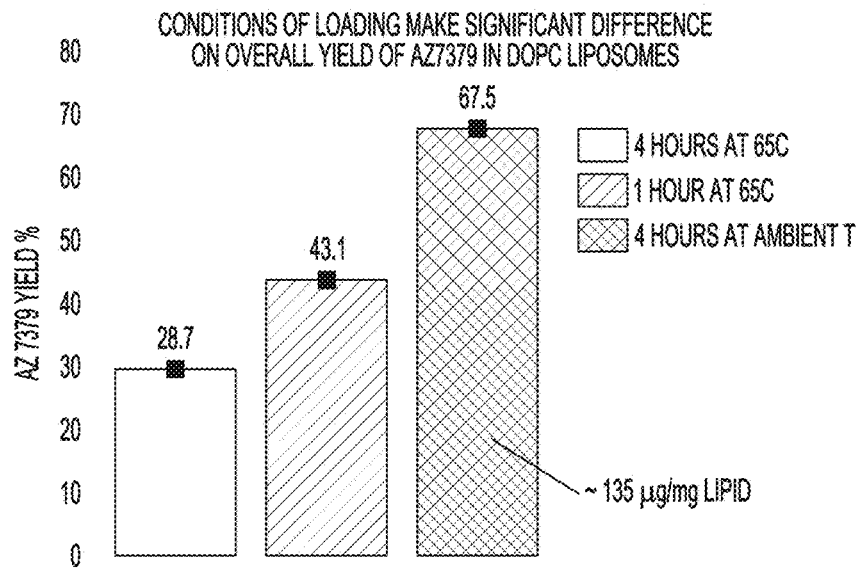

FIG. 19 depicts percent AZ7379 remote loaded. With the 4 h at RT condition, it was observed that 67.5% AZ7379 remote loaded with a final drug to lipid concentration of 135 μg/mg lipid. While the 65° C. for 1 h and 4 h had only about 28.7 and 43.1 percent AZ7379 loaded respectively.

Figure 20:
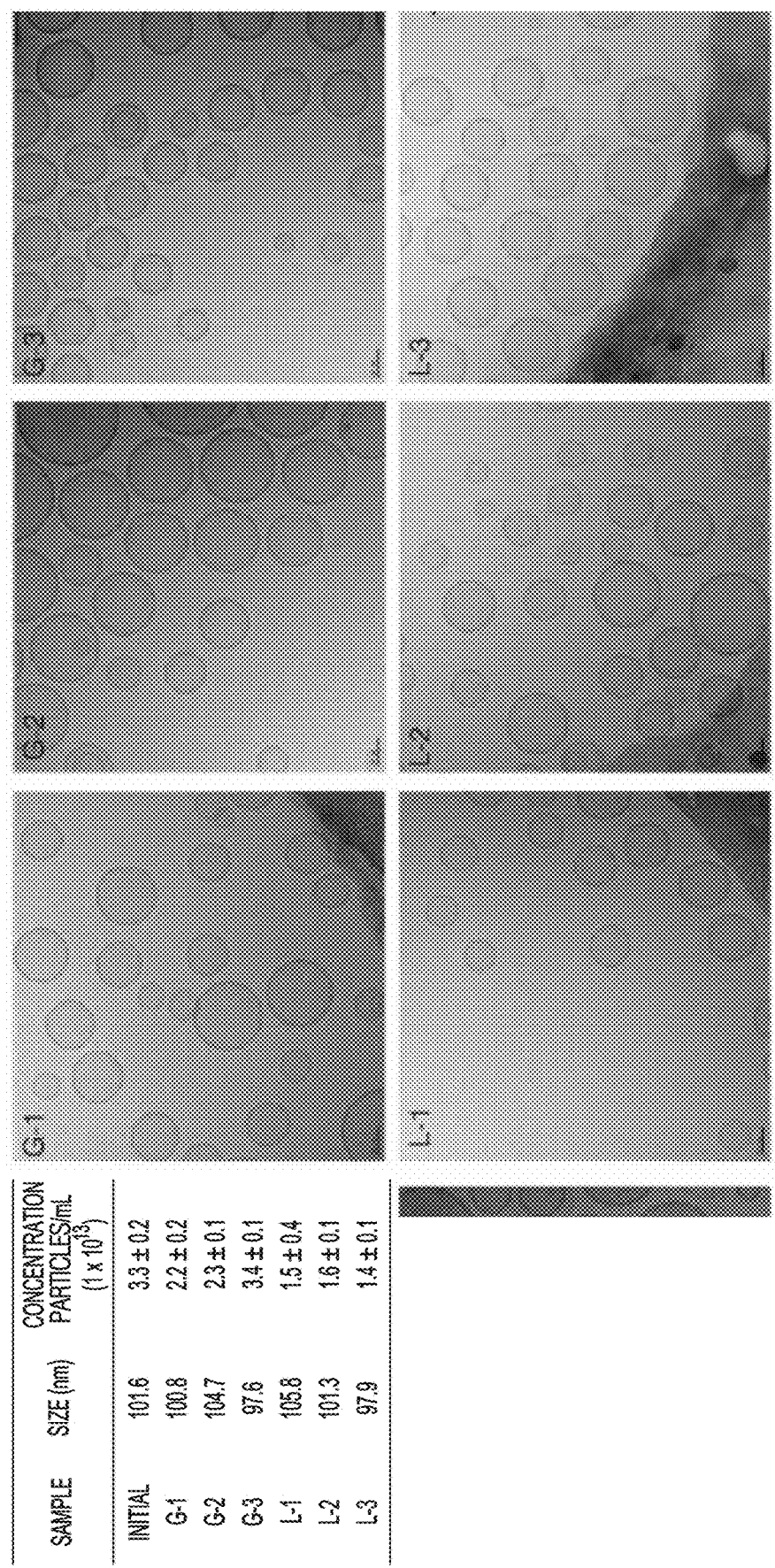

FIG. 20 depicts Cryo-TEM to study the structure of liposomes at various stages of remote loading. Initial liposomes prepared by REV process was divided into three parts and each part was remote loaded by incubating AZ7379 with liposomes for 4 h at RT. Cryo-TEM was carried out for each of the samples listed in the table to study the structure of liposomes that were initially prepared, passed through the size exclusion once to remove ammonium sulfate (G-1, G-2, G-3) and finally after removing unloaded AZ7379 (L-1, L-2, L-3). Most of the liposomes were unilamellar in nature with the size ranging from 50-120 nm in diameter.

Figure 21:
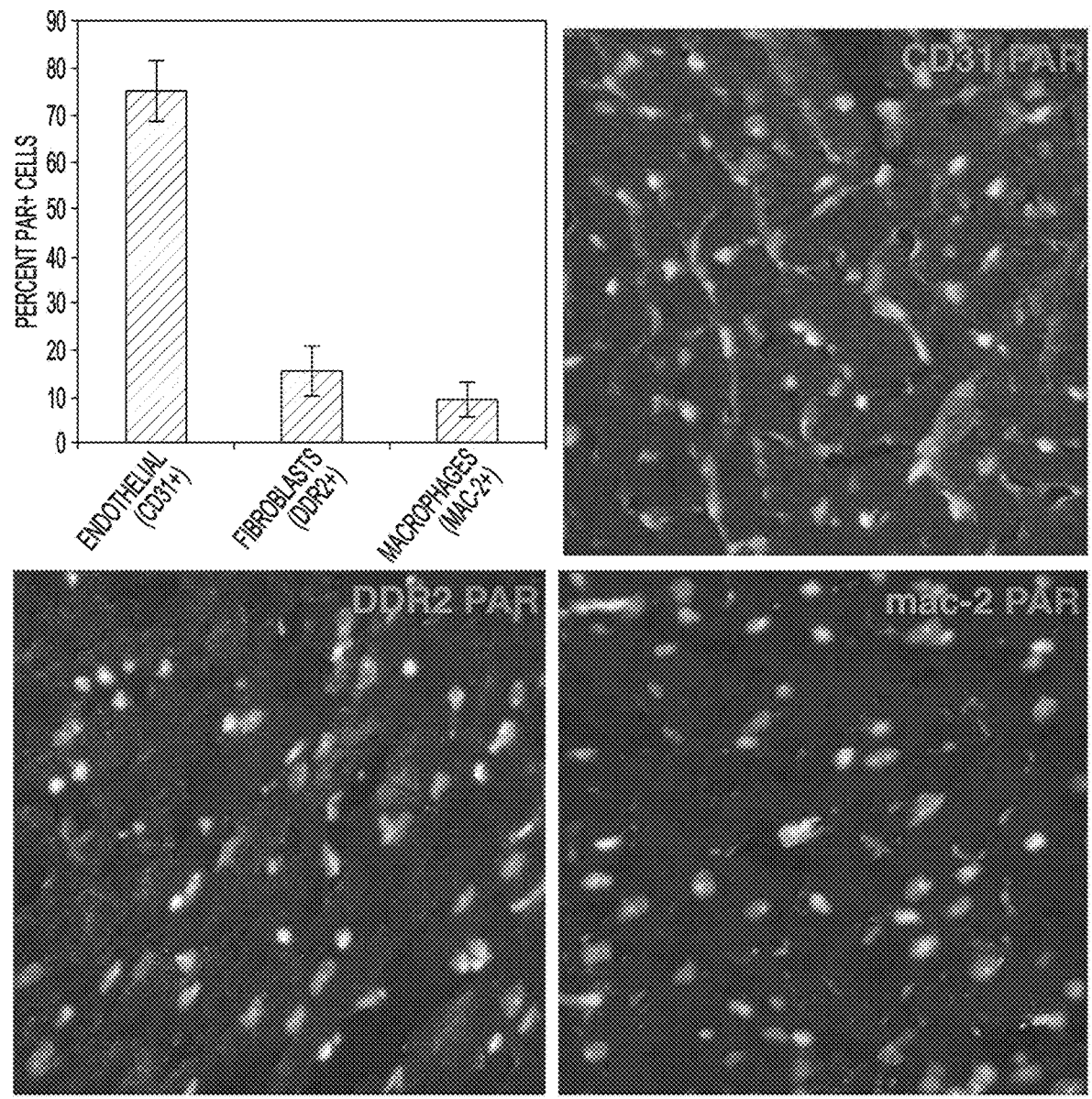

FIG. 21 depicts PAR expression in 24 week HFD fed mice. A) PAR expression in endothelial, fibroblasts and macrophages of DIO hearts. PAR immunofluorescence in relation to B) endothelial cells, fibroblasts and macrophages.

Figure 22A:
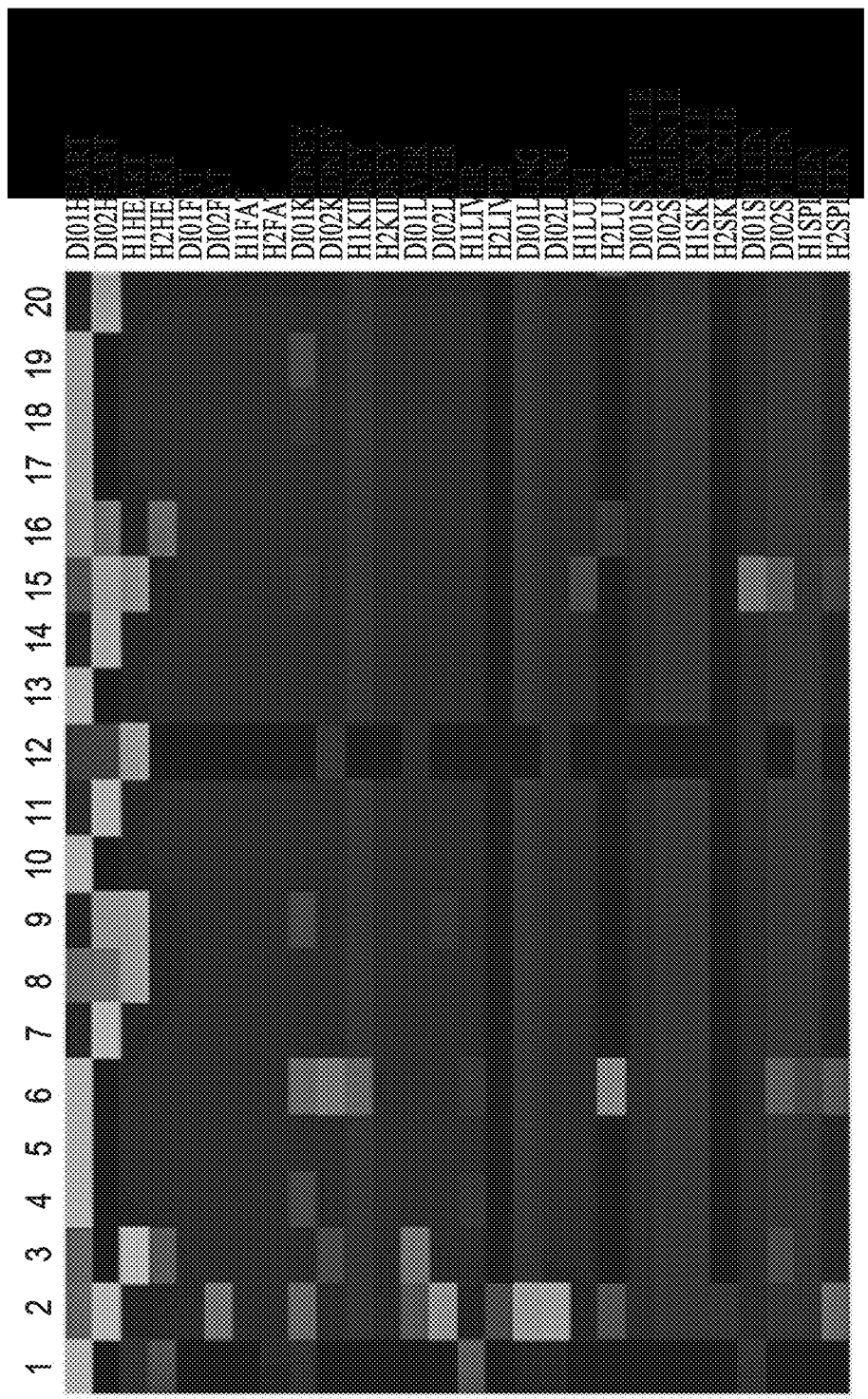
Figure 22B:
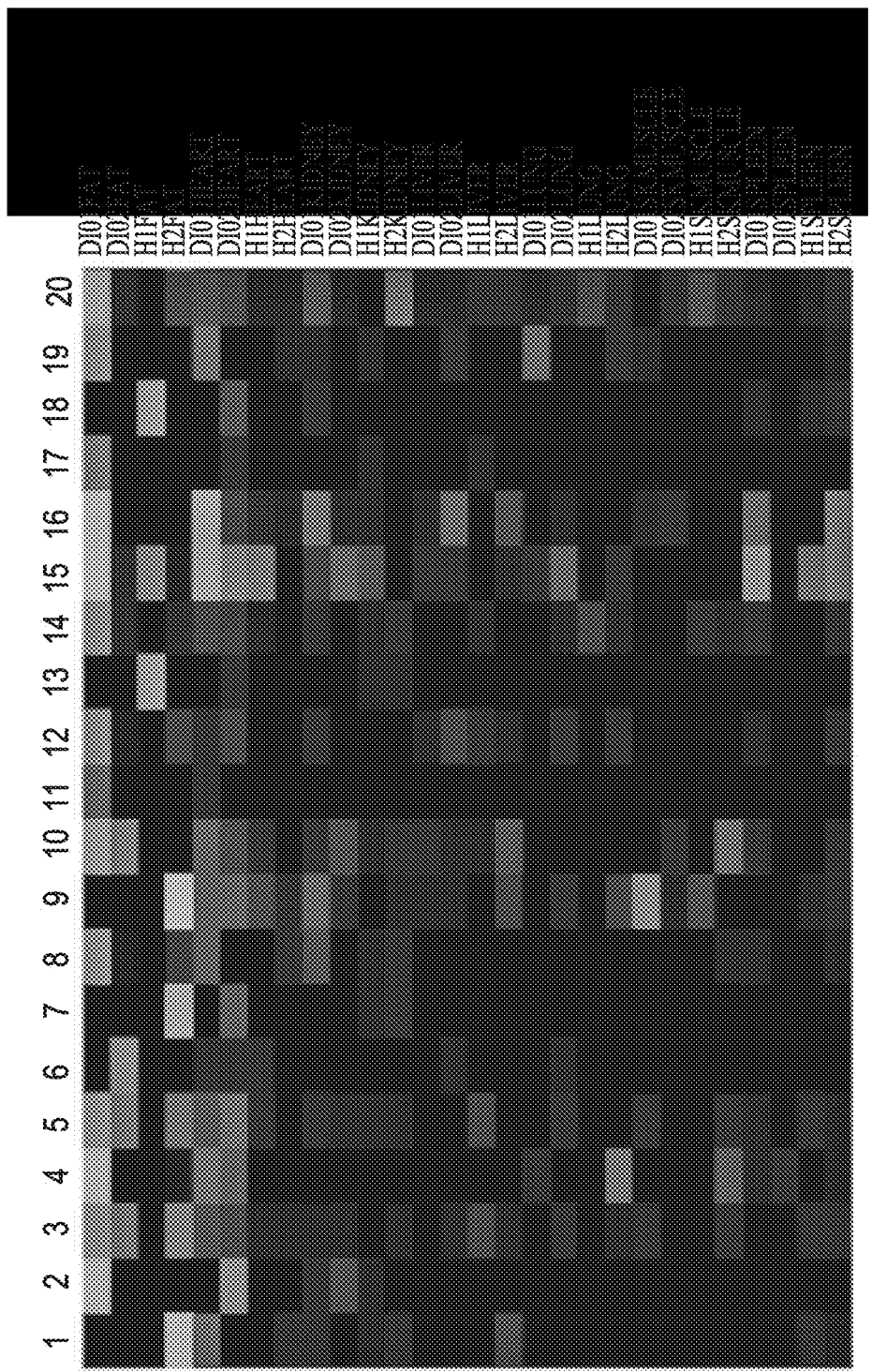
Figure 22C:
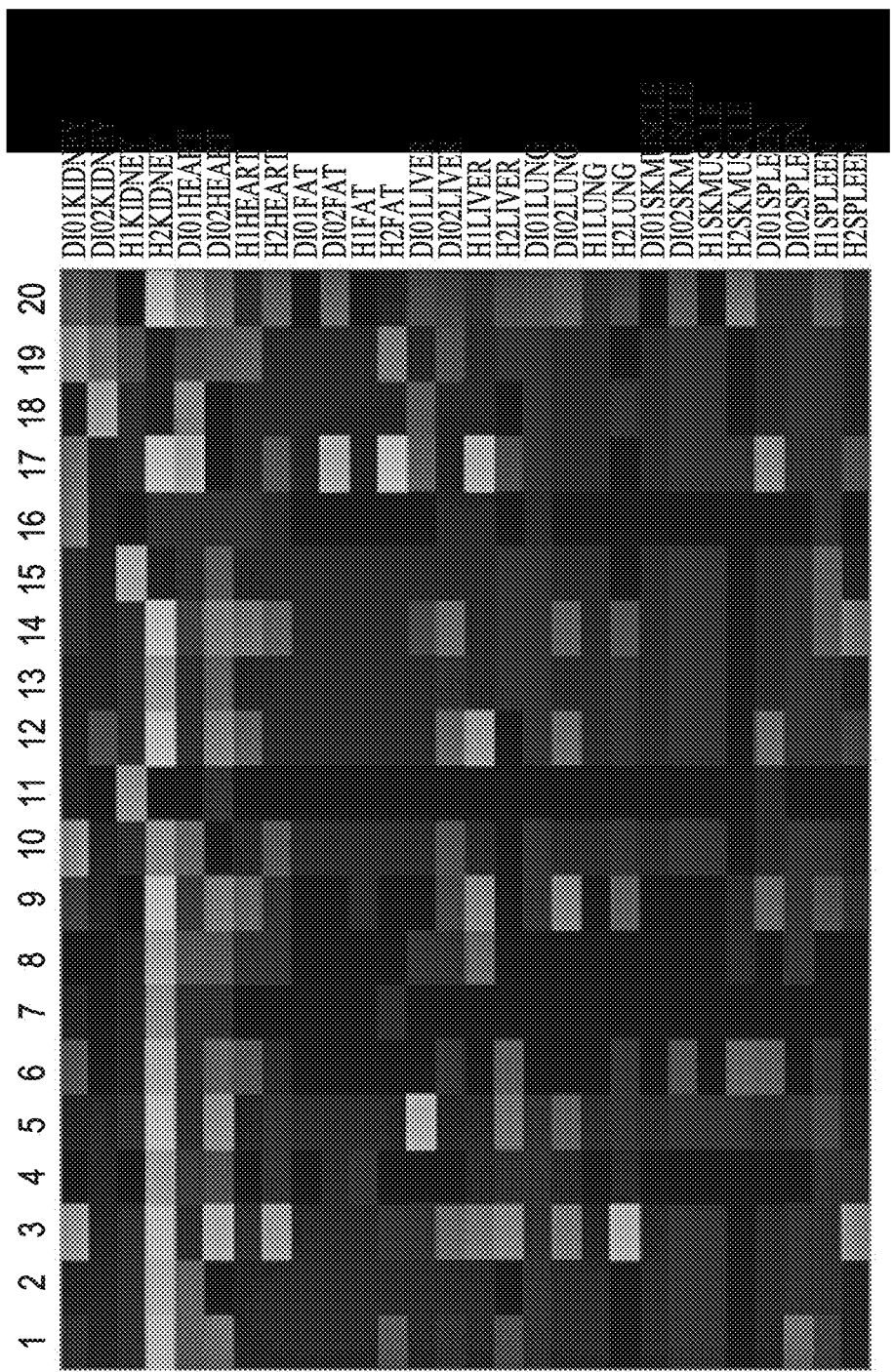

FIG. 22 depicts peptide heat maps derived from Next-Gen sequencing showing top 20 peptides specific for heart, fat and kidneys in healthy and DIO animals. A) Heat map showing top 20 peptides with higher specificity for healthy and DIO hearts than for other organs in healthy or DIO animals. B) Heat map showing top 20 peptides with higher specificity for healthy and DIO fat than for other organs in healthy or DIO animals. C) Heat map showing top 20 peptides with higher specificity for healthy and DIO kidneys than for other organs in healthy or DIO animals.

FIG. 23 depicts AZ7379 dosing at 5 mol/kg and 25 μfmol/kg vs control.

FIG. 24A-B depicts Hornerin expression in human MI specimens. A) Table showing information on the human specimens obtained from UVA Biorepository and Tissue Facility (BTRF). B) Hornerin expression was not seen in the healthy regions of the specimens but only seen in the infarct and infarct border zones of the same hearts. Also a control IgG was used to show the specificity of hornerin antibody (Scale bar; 20 μm).

FIG. 25A-E depicts physical properties of PTK787 and Cryo TEM of B-40 liposomes at various stages of remote loading. A) Physiochemical properties of PTK787 as provided by a: ACD/Labs, b: Marvin, c: Selleck chemicals. Remote loading of PTK787 (5 mg/ml) into B-40 liposomes (endothelial specific) using 250 mM ammonium sulfate. B) Liposomes freshly prepared and extruded using 0.2 μm filter and this stage of the procedure; ammonium sulfate is present inside and outside of the liposomes. Liposomes after the first C) and second size D) exclusion to remove exterior ammonium sulfate. E) Liposomes after remote loading PTK787 carried out by incubating the liposomes and the drug at 55° C. for 1 h. (Scale bar; 50 nm).

Figure 26A:
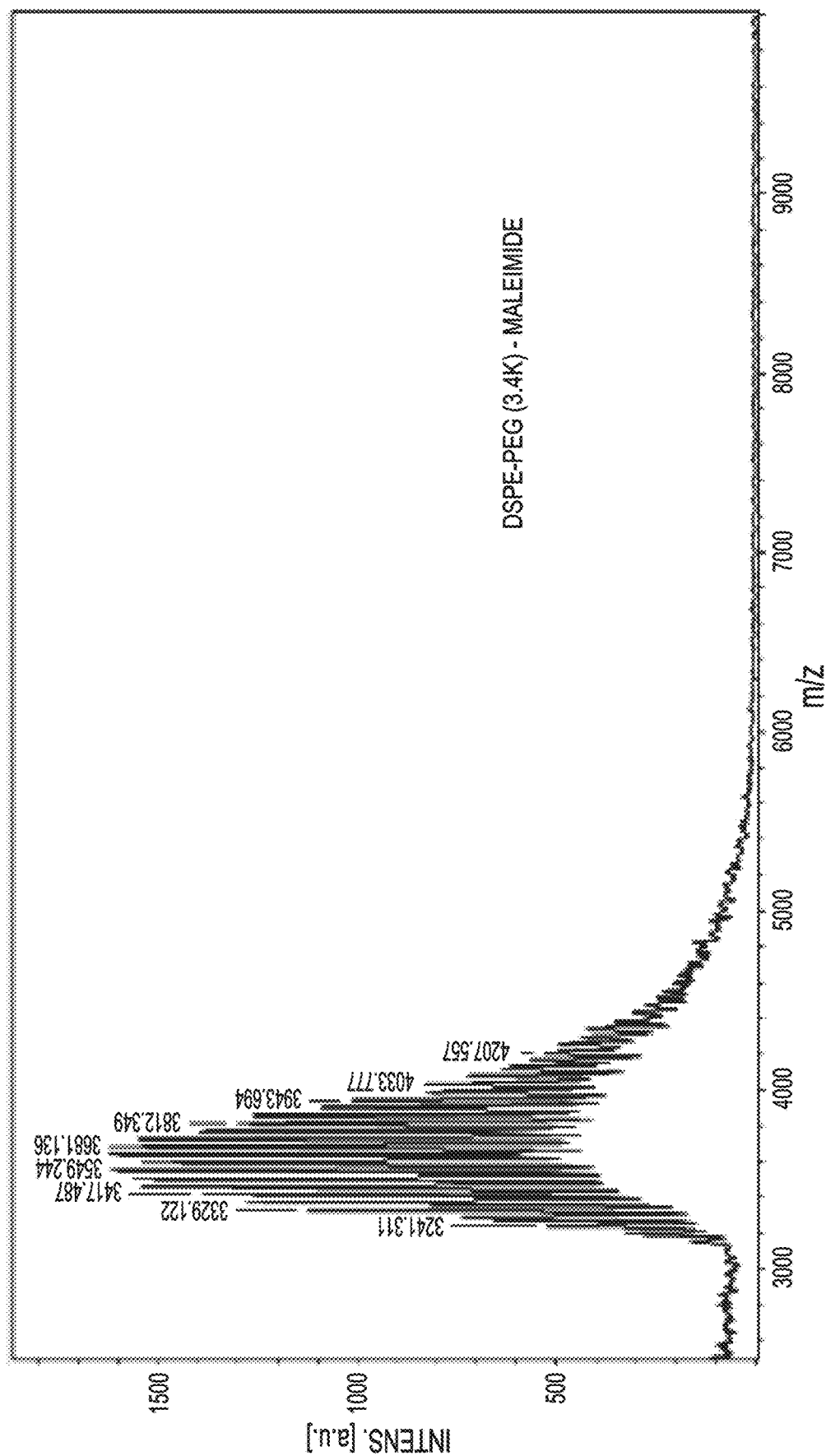
Figure 26B:
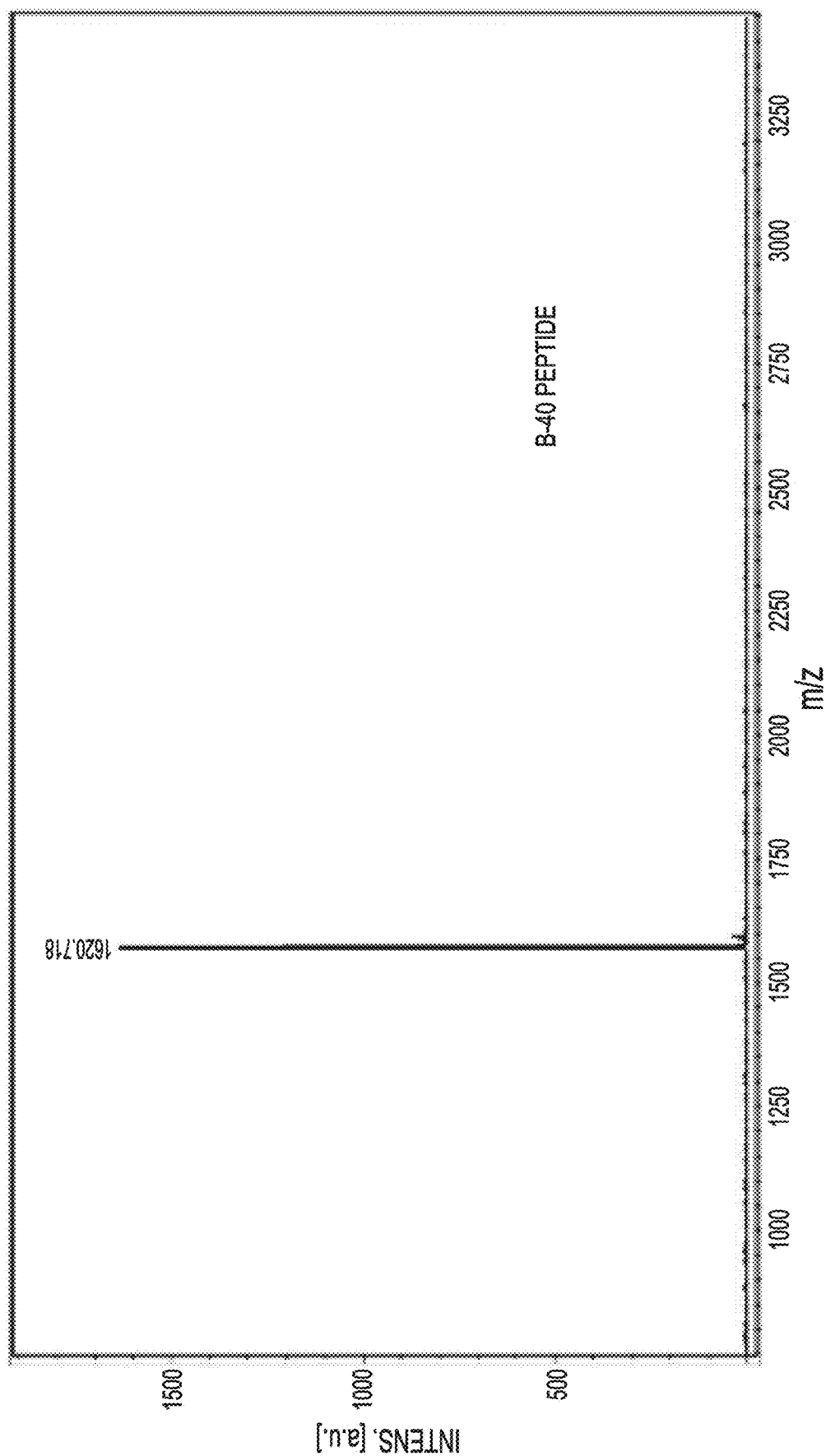
Figure 26C:
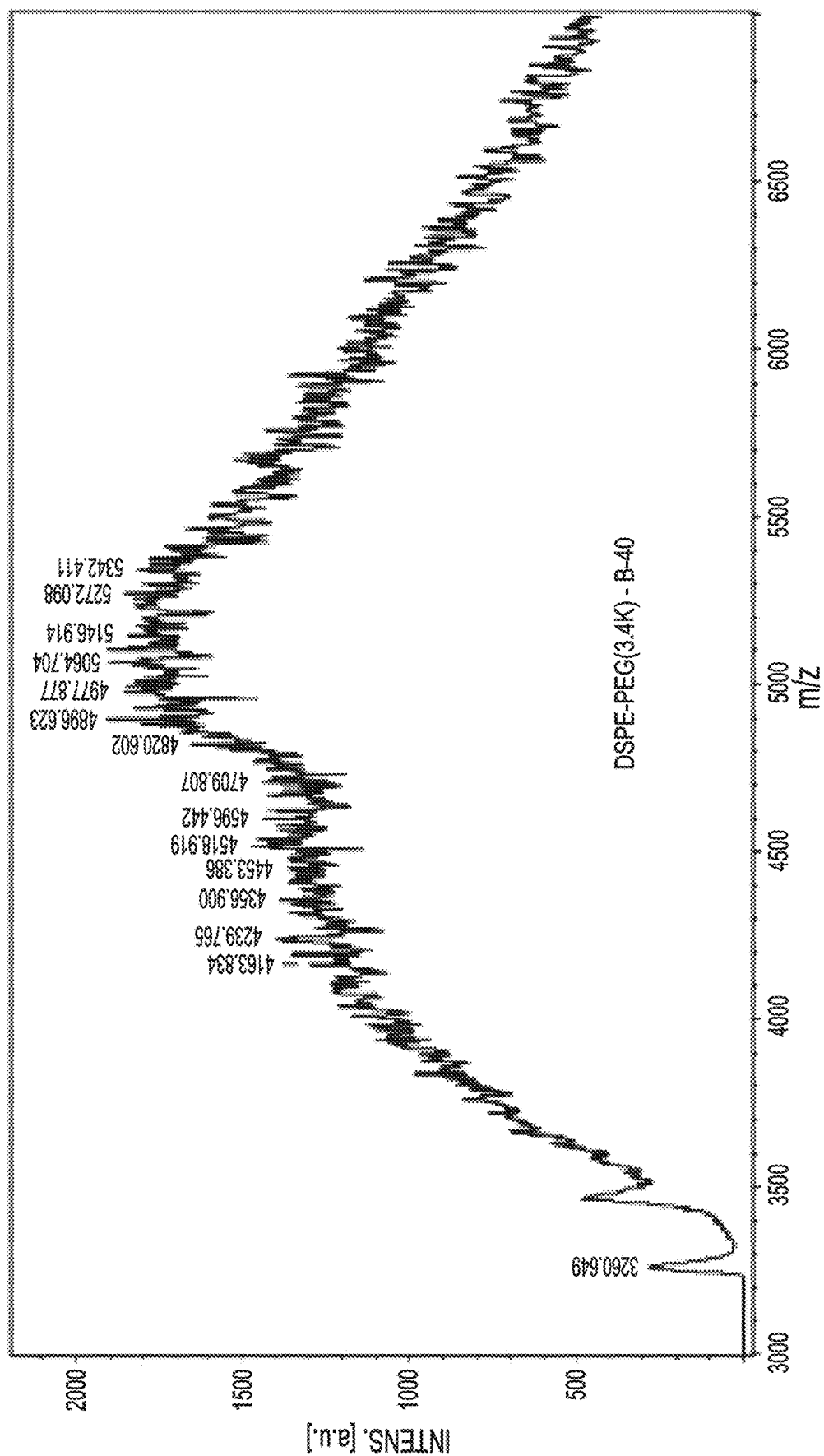

FIG. 26A-C depicts mass spectrometry of DSPE-PEG-Maleimide, B-40 peptide and DSPE-PEG-B-40 peptide. Mass spectrometry was carried out of the initial A) DSPE-PEG-Maleimide and B) B-40. The reaction was carried out at room temperature for 1 h followed by overnight incubation at 4° C. in degassed PBS containing 0.5 nM EDTA. The reaction mixture was dialyzed over 48 h first against PBS and later water. The reaction mixture was later freeze dried and used for liposomal preparation. C) Peptide-PEG-DSPE was also characterized by mass spectrometry.

Figure 27:
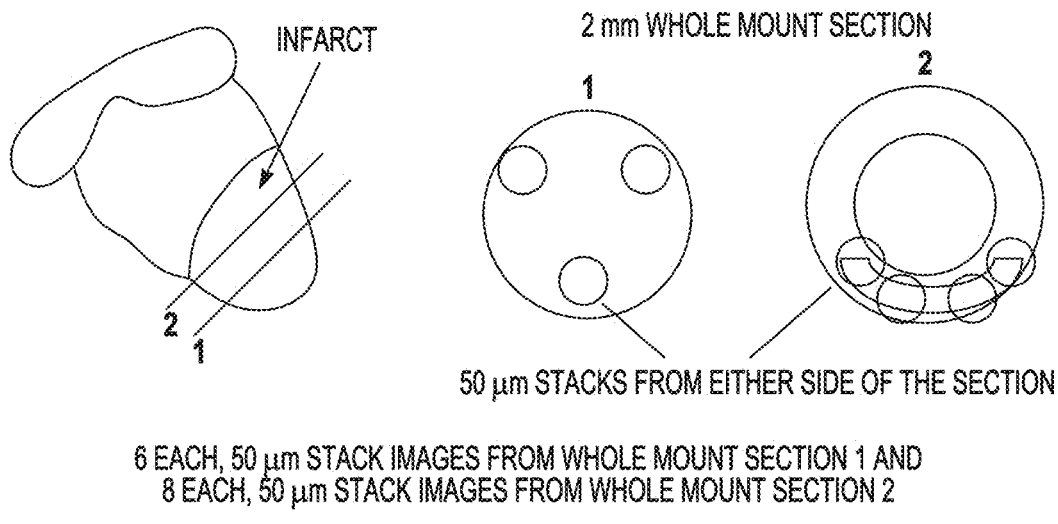

FIG. 27 depicts a cartoon showing the regions of infarcted hearts used for whole mount vessel imaging. Infarct hearts were cut along the short axis (4 pieces of 2 mm) and the 2 pieces close to the apex were used for whole mount vessel imaging. The circles show the approximate regions from where 50 μm stack images were taken. From either sides of the 2 mm sections, 50 μm stack images were taken with a total of 14 images per heart were taken for calculating vessel volume fraction using RAVE software.

Figure 28:
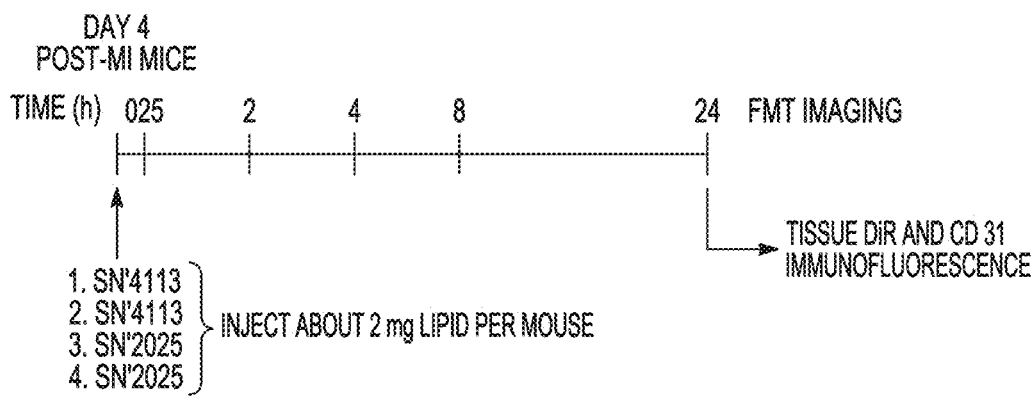

FIG. 28 depicts alternative B-40 peptides synthesized to be incorporated into liposomes. B-40 peptides (SN'4113—original, SN'2011—oxidized methionine, SN'2025—norleucine version) were conjugated to DSPE-PEG-NHS ester and purified before making liposomes. Liposomes were either prepared via the hydration method or the REV process. Liposomes with SN'2011-lipid conjugate were not successful via the REV process but were successful with the regular hydration method. Using hydration method SN'4113 and SN'20125 liposomes, PK was determined in Day 4 post-MI mice as outlined in the lower part of the figure.

Figure 29A:
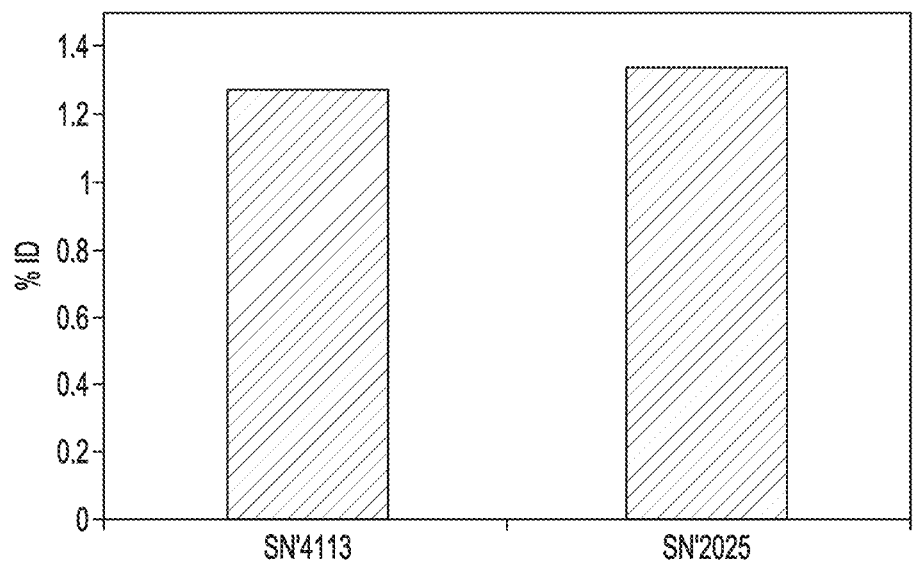
Figure 29B:
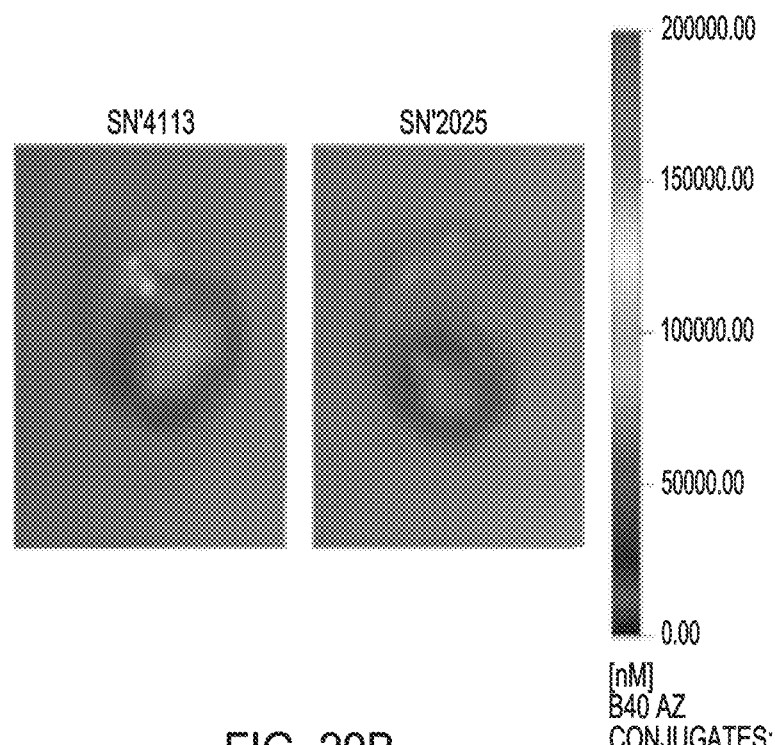

FIGS. 29A-B depict in vivo FMT images showing the heart region at different time points after liposome injection.

Animals (n=4) were injected with either the SN'4113 and SN'2015 liposomes tagged with DiR to facilitate FMT tracking of liposomes. FMT imaging was carried out at 0.25, 8 and 24 h post injection and using Truequant software, DiR was quantified in the heart ROI. Lower—PK curve derived from the DiR values from heart ROI at various time intervals. Note—the prolife of original B-40 peptide synthesized at UVA and SN'4113 synthesized have overlapping prolife. Similarly, the SN'2025 also has similar trend like that of the original B-40 liposomes.

Figure 30:
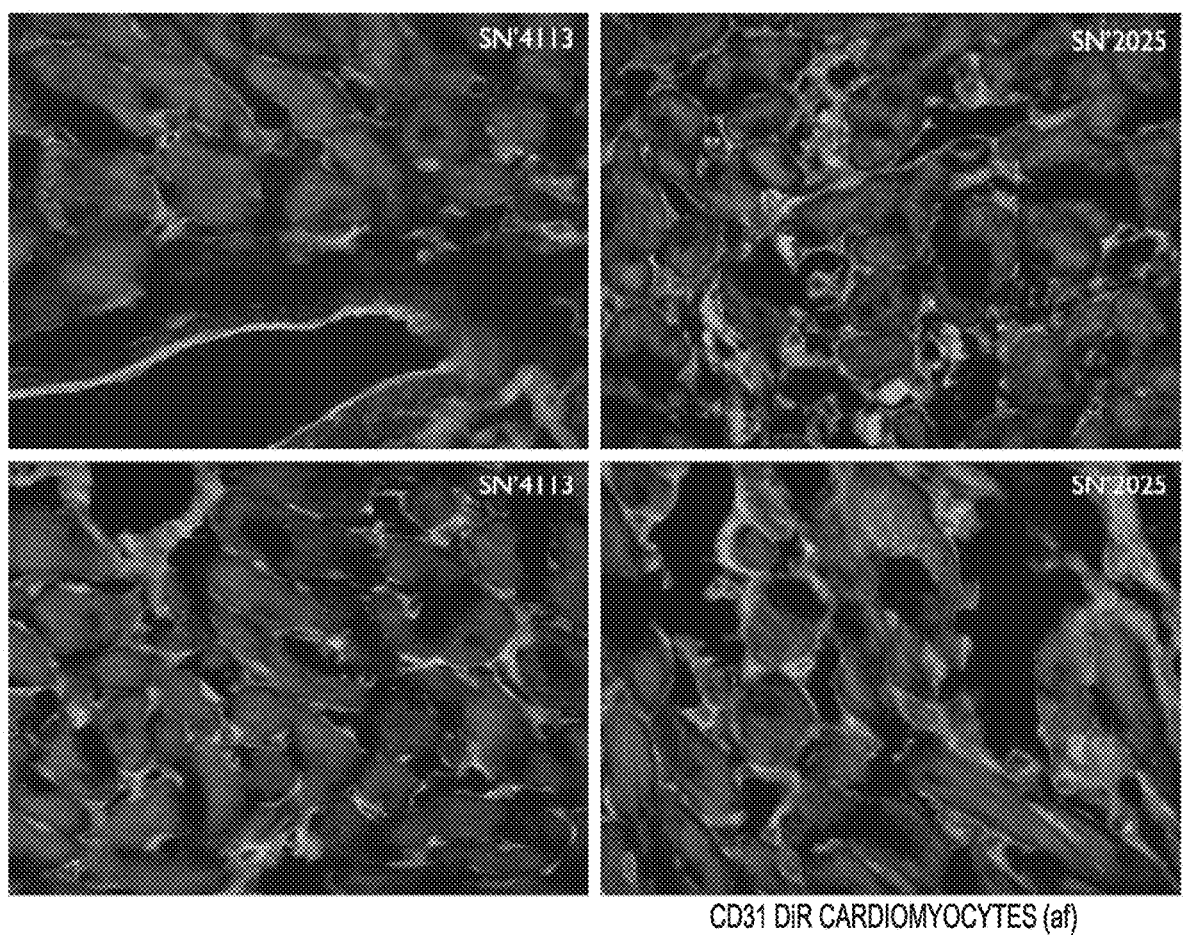

FIG. 30 depicts ex vivo FMT images showing the hearts injected with SN'4113 and SN'2025 liposomes. Ex vivo FMT quantification 24h post injection shows similar accumulation of both liposomes in day 4 post-MI hearts. Tissue immunofluorescence of these hearts suggests the localization of both liposomes in the border zone endothelium.

Figure 31:
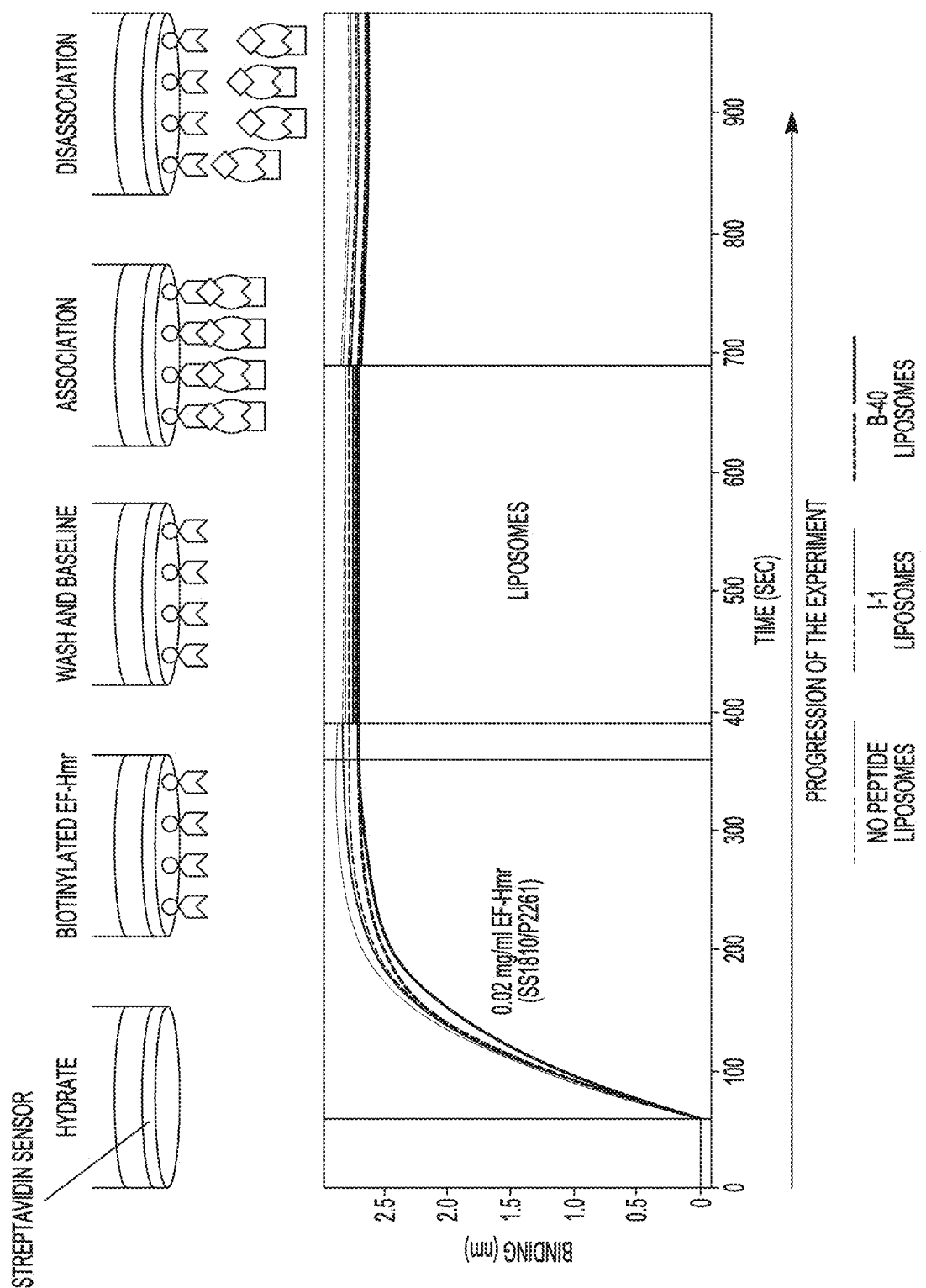

FIG. 31 depicts biolayer interferometry to determine B-40 liposome binding to EF fragment of Hornerin. Using Fortebio octect system, B-40 liposomes binding to EF fragment was carried out. Streptavidin sensors were coated with Biotinylated EF fragments and their interaction with no peptide, I-1 and B-40 liposomes was tested. Initial results suggest no binding of B-40 peptide to the EF fragment of hornerin.

Figures 32A, 32B:
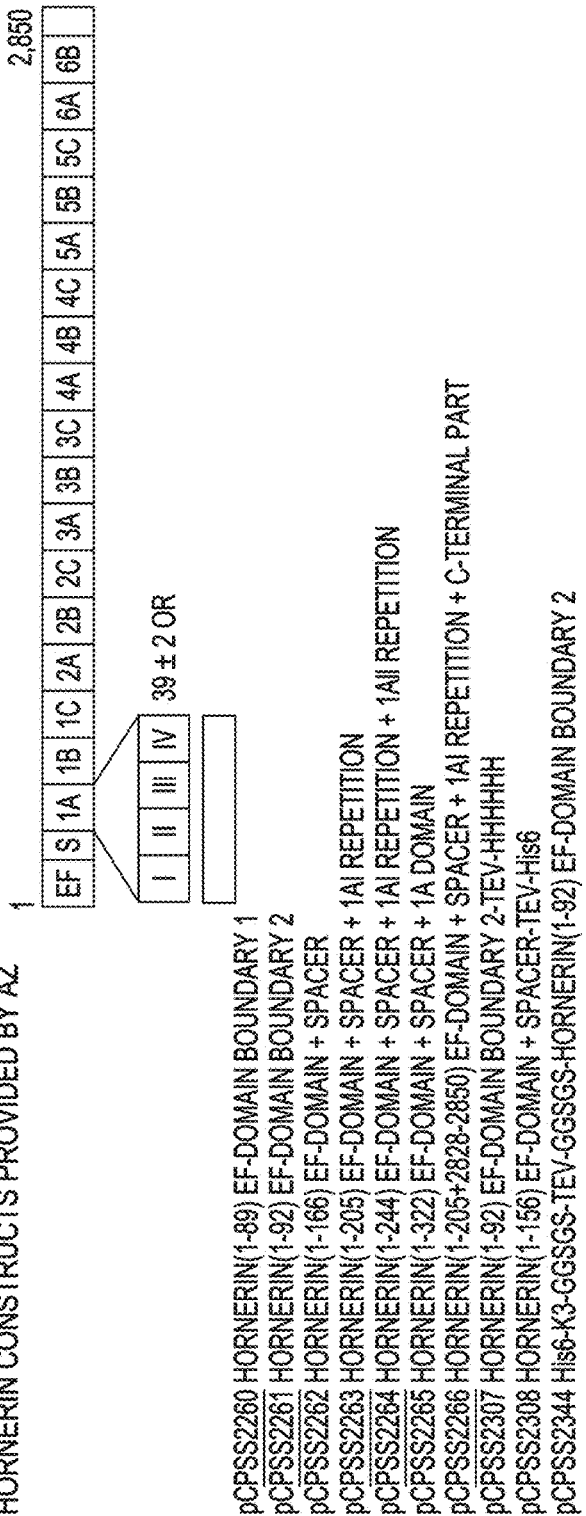

FIGS. 32A-B depict hornerin constructs. Different versions of the hornerin fragments containing EF domains were created to test the binding of B-40 peptide to hornerin (SEQ ID NOs: 253 and 254). The table shows the region of hornerin protein that was incorporated into the EF constructs and the over size of the EF domains.

Figure 33:
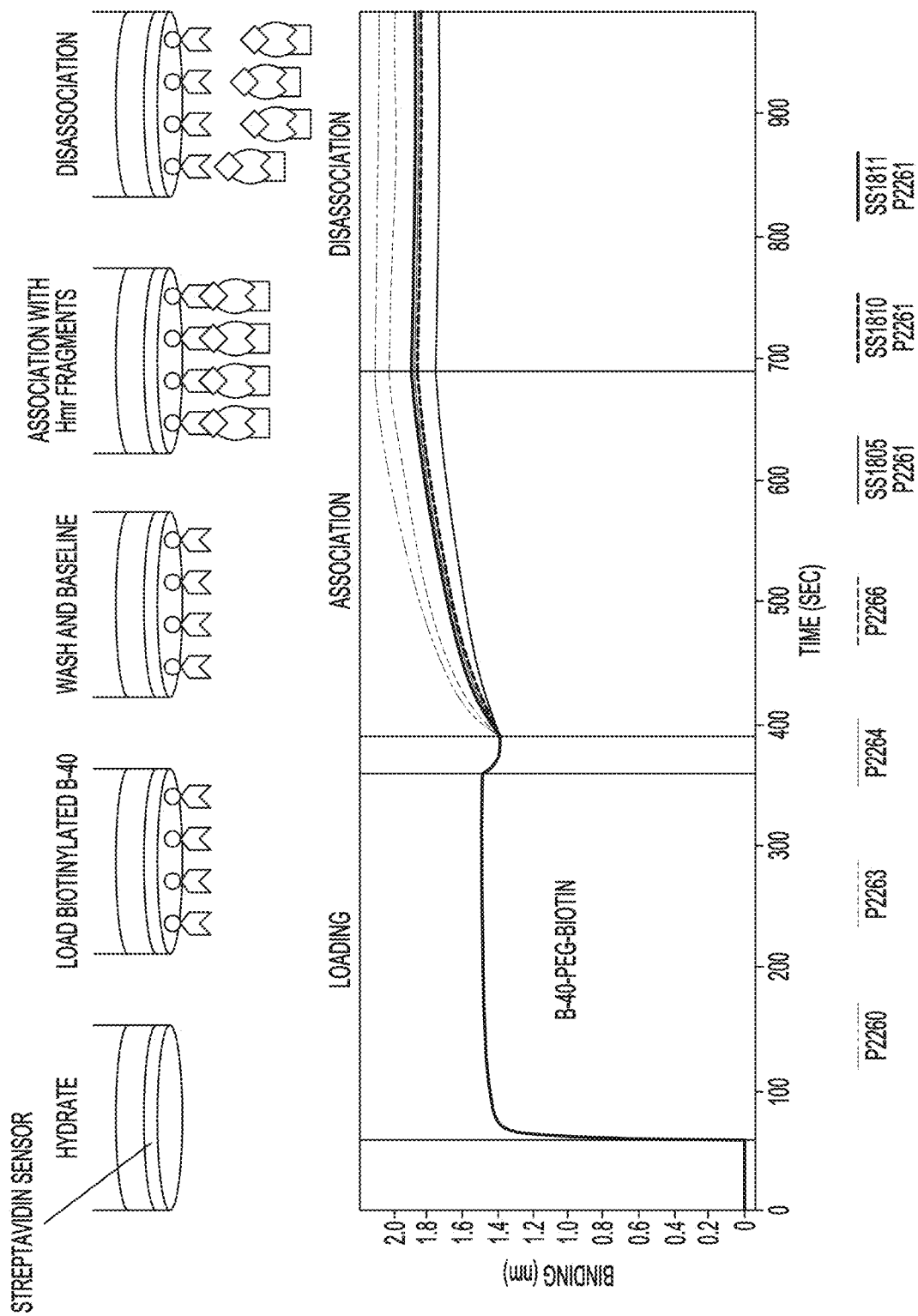

FIG. 33 depicts biolayer interferometry to determine B-40 liposome binding to EF domains. Using Fortebio octect system, B-40 peptide binding to different EF fragments was carried out. Streptavidin sensors were coated with biotinylated B-40 peptide and its interaction with different fragments containing EF domains was carried out. Initial binding results suggest that EF domain as a possible binding partner of B-40 peptide.

Figure 34A:
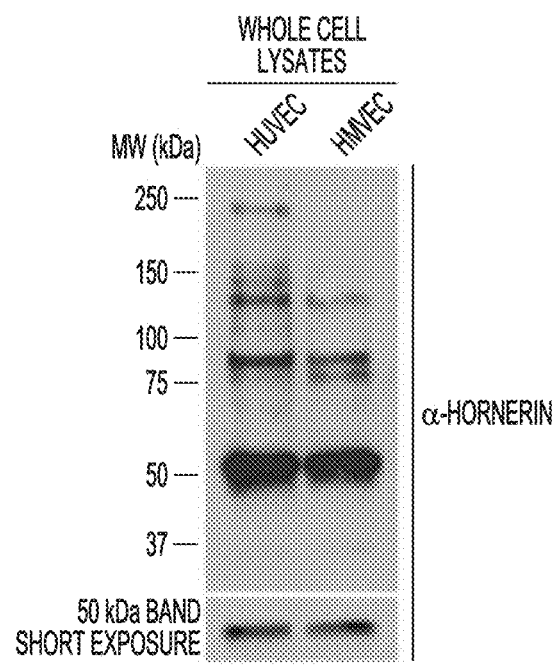
Figure 34B:
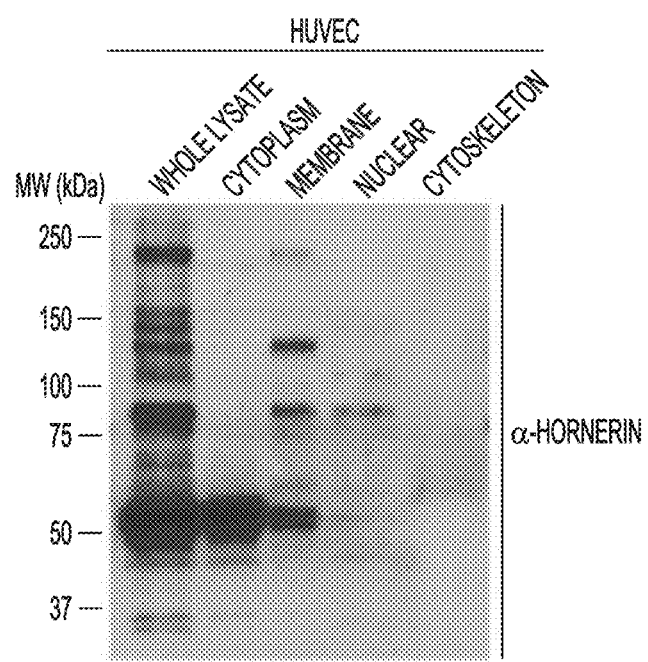

FIGS. 34A-B depict Western blot (WB) of hornerin from whole cell lysate prepared from HUVECs and HMVECs (left). WB of hornerin from fractions derived from different compartments of HUVECs (right).

Figure 35:
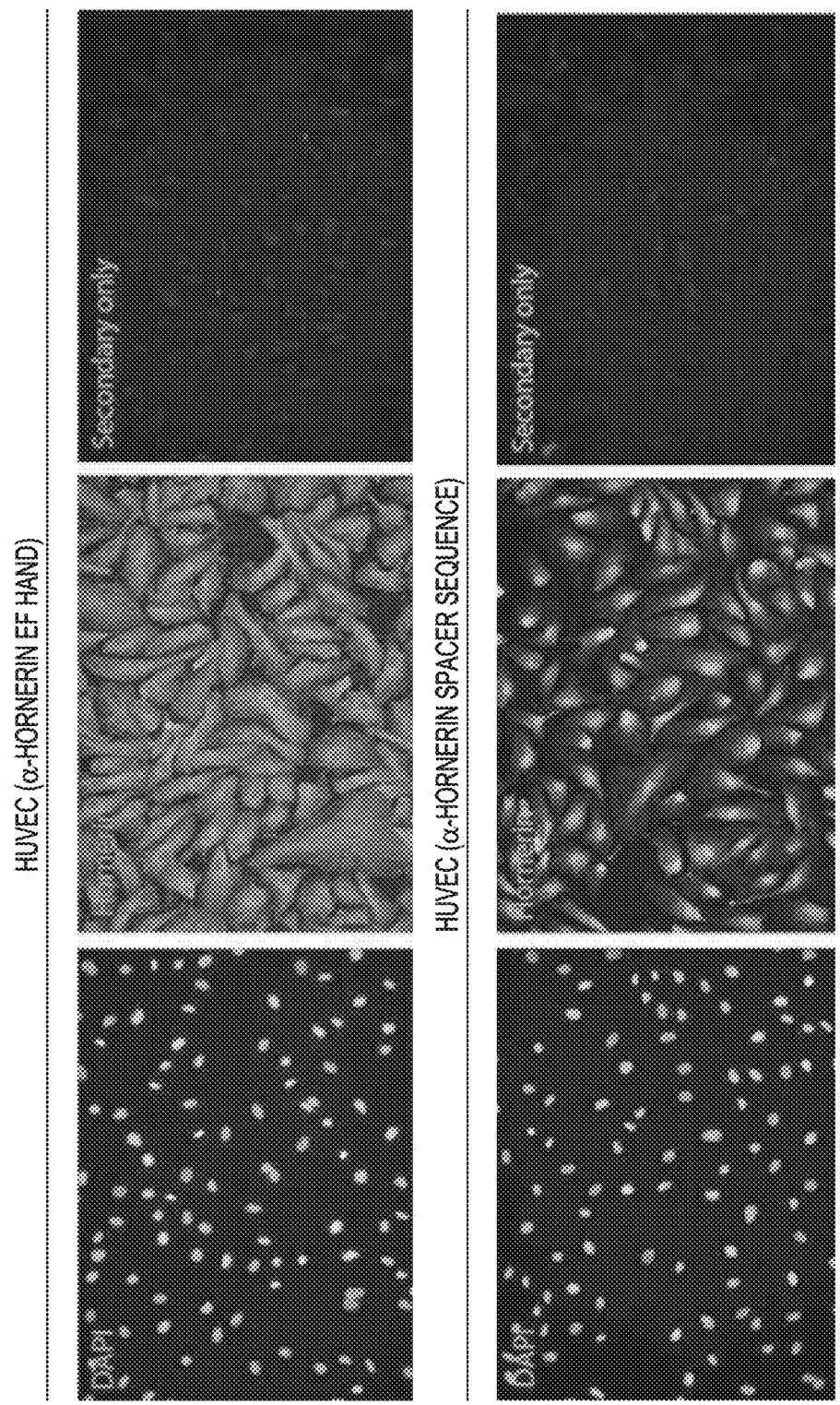

FIG. 35 depicts immunofluorescence images of hornerin in HUVECs using antibodies against the EF hand domain or spacer region. Note that the antibody against the EF hand domain yielded cytoplasmic staining that was strongest in the perinuclear region (top center), whereas the antibody against the spacer region mainly stained the nucleus.

Figure 36A:
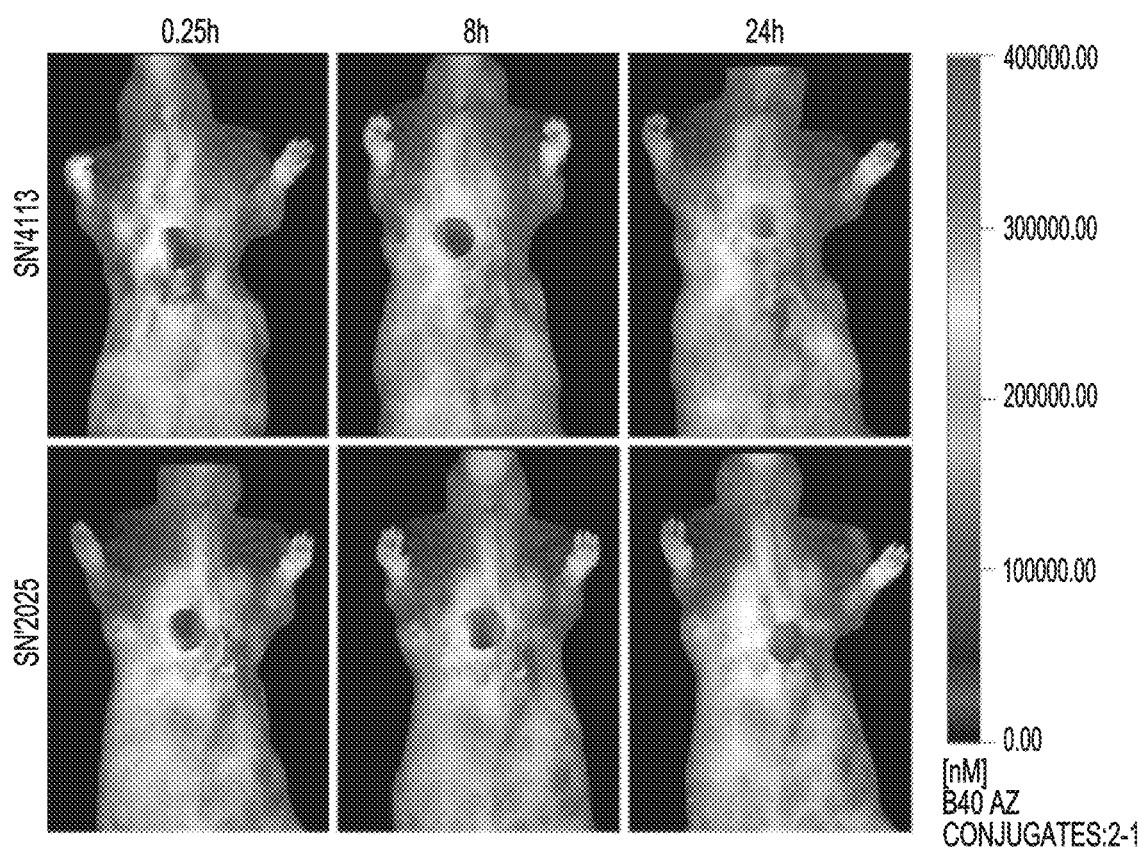
Figure 36B:
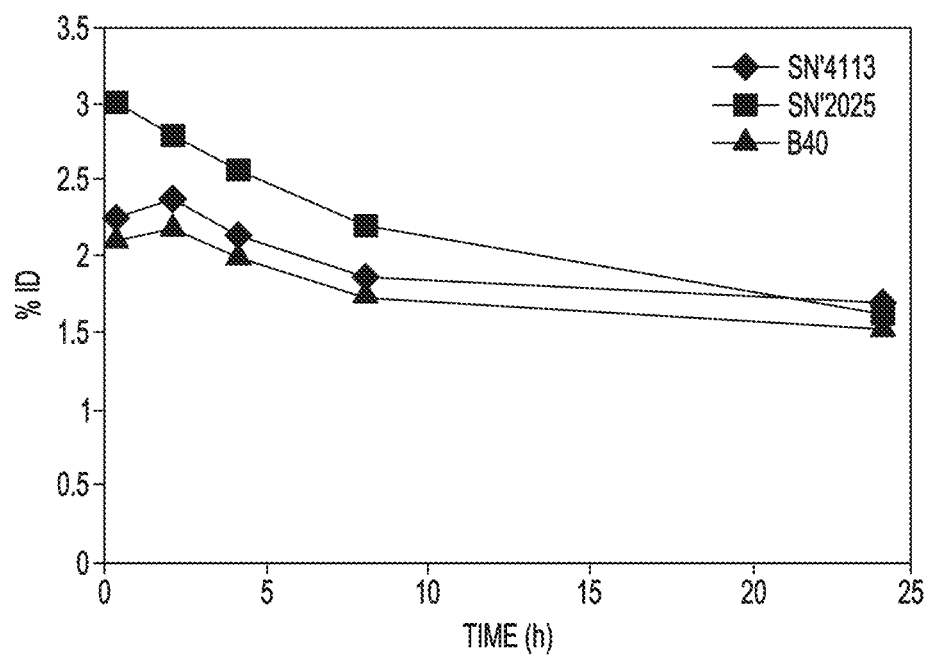

FIGS. 36A-B provide a timeline.

DETAILED DESCRIPTION OF THE INVENTION

Provided herein is the identification of peptides which target specific cell types in the infarct/border zone and use those peptides to target liposomes loaded with regenerative compounds.

Many of the therapeutic approaches being investigated for limiting LV remodeling post-MI involve systemic administration, but suffer from limited efficacy due to poor exposure either due to short half-life or dose-limiting toxicity. Because it is a multiphase event, the therapeutic bioengineering of LV remodeling can require different pharmacologic interventions at different stages of the process. Most drug delivery systems lack specificity for damaged tissue and therefore may adversely affect surrounding or off-target tissue. Optimal drug delivery, therefore, requires the ability to preferentially localize the therapeutic agent to the site(s) of injury, while maintaining a reservoir of drug that is less avidly processed by healthy tissue. One way of increasing local drug concentration is by catheter-based local delivery upon revascularization after percutaneous coronary intervention (PCI) (8). Many of the experimental approaches to treating the post-infarct heart involve supplying growth factors, cytokines, drugs and other biomolecules to the infarct zone. These therapeutic agents have been delivered by direct injection or by biomolecule-loaded nanoparticles through intracoronary infusion. The efficacy of these approaches may be limited by lack of retention of the factors or nanoparticles in the desired area. Furthermore, local delivery that is not performed in conjunction with acute revascularization would require repeat catheterization which is neither practical nor cost-effective (9).

Liposome-based delivery of therapeutic agents has been used successfully to eliminate the off-target effects that often limit the clinical utility of drugs [10]. Liposomes allow for surface modifications with different targeting ligands including antibodies, antibody fragments and peptides that are specific for the diseased tissue. This allows for the efficient accumulation of drugs in the diseased tissue and thus reducing the exposure of healthy tissue to the drug and at the same time increasing the drug half-life. However, the post-infarct heart contains a wide variety of cell types that could be potential targets for therapy, and a comprehensive set of ligands that target the major cell types of therapeutic interest in the post-infarct heart has yet to be reported. Towards this end, using phage display technology, peptides were identified that are specific for activated endothelial cells, ischemic cardiomyocytes, myofibroblasts, and c-Kit positive cells present in the infarct/border zone. In addition to developing molecular imaging agents, a liposomal formulation of an poly(ADP-Ribose) Polymerase-1 (PARP-1) inhibitor (AZ7379) was developed, that enabled the translation of targeted delivery into a pharmacological response. PARP-1 is a nuclear enzyme that is activated in response to oxidative stress (11). It catalyzes the formation of poly (ADP-ribose) (PAR), which can be quantified by ELISA or by immunofluorescence microscopy. The latter technique was used in combination with cardiomyocyte-targeted delivery of AZ7379 to demonstrate cardiomyocyte-specific inhibition of PARP-1. The number of poly (ADPribose) (PAR) positive nuclei 24 h after dosing was used as the pharmacodynamic endpoint to compare the efficacy between various liposomal formulations containing AZ7379. When it was formulated as a liposomal preparation, the presence of total AZ7379 was prolonged in circulation. Furthermore, inclusion of the cardiomyocyte specific I-1 peptide into the formulation increased efficacy almost an order of magnitude in border zone-resident cardiomyocytes, as compared to the same liposomes bearing a negative control peptide (NCP). The results of this benefits therapeutic strategies including cardiac regeneration, wherein the therapeutic agent needs to be delivered precisely to the infarct/border zone in order to minimize off-target effects.

For the purposes of clarity and a concise description, features can be described herein as part of the same or separate embodiments; however it will be appreciated that the scope of the invention may include embodiments having combinations of all or some of the features described.

Definitions

The following definitions are included to provide a clear and consistent understanding of the specification and claims.

As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment," "an embodiment," etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is di-substituted.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including," "includes," "having," "has," "with," or variants thereof, are intended to be inclusive similar to the term "comprising."

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group.

Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating," "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit," "inhibiting," and "inhibition" refer to the slowing, halting, or reversing the growth or progression of a disease, infection, condition, group of cells, protein or its expression. The inhibition can be greater than about 20%, 40%, 60%, 80%, 90%, 95%, or 99%, for example, compared to the growth or progression that occurs in the absence of the treatment or contacting.

A "targeting molecule" or "targeting agent" is a peptide or other molecule that binds to a targeted component). Optionally, the binding affinity of the targeting molecule may be in the range of 1 nM to 1 µM. In some embodiments, the targeting molecule may be an antagonist of a receptor on the surface of a targeted cell.

A "therapeutic agent," "active agent," or "drug" refers to any molecule used in the treatment, cure, prevention, or diagnosis of a disease or other medical condition. Examples of therapeutic agents include, but are not limited to, FDA-approved drugs, experimental drugs, antibiotics, and nucleic acids (e.g., siRNA, DNA).

As used herein, a "nanoparticle" refers to a micelle or liposome. A delivery vehicle can mean the vehicle alone or one loaded with a therapeutic and/or a diagnostic agent and/or also comprising a targeting peptide of Table 1 or related thereto (e.g., 95% identity).

The term lipid includes mono-, di- and triacylglycerols, phospholipids, free fatty acids, fatty alcohols, cholesterol, cholesterol esters, and the like.

The term "phospholipid" as used herein refers to a glycerol phosphate with an organic head-group such as choline, serine, ethanolamine or inositol and zero, one or two (typically one or two) fatty acids esterified to the glycerol backbone. Phospholipids include, but are not limited to, phosphatidylcholine, phosphatidylethanolamine, phosphatidylserine and phosphatidylinositol as well as corresponding lysophospholipids.

The terms "active agent," "therapeutic agent," "drug," and the like, are readily recognized by those of kill in the art. The micelles and liposomes described herein can encapsulate various drugs, such as those drugs exemplified in the description herein, or another therapeutic or otherwise active agent known in the art.

The terms "cell," "cell line," and "cell culture" as used herein may be used interchangeably. All of these terms also include their progeny, which are any and all subsequent generations. It is understood that all progeny may not be identical due to deliberate or inadvertent mutations.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, including at least about 75%, at least about 90%, or at least about 95% of the nucleotide residues of the first portion are capable of base pairing with nucleotide residues in the second portion. In some embodiments, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCCS' and 3'TATGGCS' share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

As an example of linker technology, see Bausch et al. Clin Cancer Res. 2011 Jan. 15; 17(2): 302-309; in which the Tetramericplectin-1-targeted peptide (tPTP-4 (βAKTLLPTPGGS(PEG5000))KKKDOTAβA-NH2) SEQ ID NO: 252) was synthesized. In other words, four plectin-targeted peptides (PTPs) were tied to a single DOTA chelator by (4) PEG5000 linkers. The DOTA, of course, then binds a payload, such as therapeutic drug or diagnostic (e.g., radioactive element needed for imaging).

Spacers are also of use in the invention, such as a PEG spacer.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "otherwise identical sample," as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "peptide" typically refers to short polypeptides.

As used herein, the term "peptide ligand" (or the word "ligand" in reference to a peptide) refers to a peptide or fragment of a protein that specifically binds to a molecule, such as a protein, carbohydrate, and the like. A receptor or binding partner of the peptide ligand can be essentially any type of molecule such as polypeptide, nucleic acid, carbohydrate, lipid, or any organic derived compound. Specific examples of ligands are peptide ligands of the present inventions (e.g., those in Table 1).

As used herein, the term "pharmaceutically-acceptable carrier" means a chemical composition with which an appropriate compound or derivative can be combined and which, following the combination, can be used to administer the appropriate compound to a subject. "Pharmaceutically acceptable" means physiologically tolerable, for either human or veterinary application. As used herein, "pharmaceutical compositions" include formulations for human and veterinary use.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "providing a prognosis" refers to providing information regarding the impact of the presence of the heart disease/disorder (e.g., as determined by the diagnostic methods of the present invention) on a subject's future health.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

By the term "specifically binds to," as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

As used herein, a "subject in need thereof" is a patient, animal, mammal, or human, who will benefit from the method of this invention.

As used herein, a "substantially homologous amino acid sequences" includes those amino acid sequences which have at least about 95% homology, at least about 96% homology, at least about 97% homology, at least about 98% homology, or at least about 99% or more homology to an amino acid sequence of a reference antibody chain Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO$_4$, 1 mM EDTA at 50° C. with washing in 2× standard saline citrate (SSC), 0.1% SDS at 50° C.; preferably in 7% (SDS), 0.5 M NaPO$_4$, 1 mM EDTA at 50° C. with washing in 1×SSC, 0.1% SDS at 50° C.; preferably 7% SDS, 0.5 M NaPO$_4$, 1 mM EDTA at 50° C. with washing in 0.5×SSC, 0.1% SDS at 50° C.; and more preferably in 7% SDS, 0.5 M NaPO$_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, at least 20%, at least 50%, at least 60%, at least 75%, at least 90%, or at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22: 1859-1862, 1981, and Matteucci et al., J. Am. Chem. Soc. 103:3185, 1981.

Targeting Peptides

The peptides of Table 1 (below; cardiovascular targeting peptides) can be prepared by well-known synthesis schemes. The peptides encompass those peptide sequences in Table I and those that have one or more substitutions, deletions and/or additions as compared to the sequences provided in Table 1 (such as those that comprise 1 or 2 substitutions, deletions and/or additions). The peptides may encompass one or more substitutions, such as conservations substitutions. They also encompass deletions and additions of one or more amino acids and non-natural amino acids. For example, the targeting peptide consists of about 5 to about 25 amino acids or about 3 to about 7, including 5, 6 and/or 7 amino acids. At least a portion of the amino acid sequence of the targeting peptide is homologous (identical) to at least 3, 4 or 5 consecutive amino acids of those peptides found in Table 1. One or more targeting peptides can be used in the practice of the invention herein.

Multiple targeting peptides of the same or different sequence can be encompassed in a formulation. Peptides other than targeting peptides can also be included. These peptides include, but are not limited to, peptides with membrane penetrating functions, nuclear targeting functions, cytosolic targeting functions, and/or endosome dissolution function (TAP peptide; buffering compounds added to the liposome compositions (polyethylamine) to burst endosome).

The peptides can be extended away from the delivery vehicle (e.g., liposome) via the use of a chain extender, such as a PEG chain extender/spacer, so that the peptide is extended away from, for example, the liposomal surface.

In one embodiment, one or more peptides are conjugated directly or indirectly via a spacer or linker molecule to a payload and optionally includes a delivery vehicle.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |

| Full Name | Three-Letter Code | One-Letter Code |
| --- | --- | --- |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity (e.g., peptidomimetic for making peptides protease resistant). Additionally, a disulfide linkage may be present or absent in the peptides of the invention.

Amino acids have the following general structure:

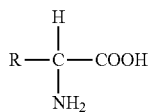

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp Embodiments of this application relate to cardiovascular tissue/cell (e.g., cardiac) targeting peptides that are selective for cardiovascular tissue/cells, in particular tissues/cells of the infarct border. The targeting peptide consists of about 5 to about 25 amino acids or about 3 to about 7, including 5, 6 and/or 7 amino acids. At least a portion of the amino acid sequence of the targeting peptide is homologous (identical) to at least 3, 4 or 5 consecutive amino acids of those peptides found in Table 1.

In some embodiments, the targeting peptides described herein includes an amino acid sequence of one or more of those presented in Table 1. In other embodiments, the targeting peptide has an amino acid sequence that consists of a sequences found in Table 1. The targeting peptide can be targeted to and selectively bind to cardiovascular tissue when administered to a subject. The targeting peptide can bind to the cardiovascular tissue with a higher affinity than non-cardiovascular tissues.

A targeting peptide of the present invention can be synthesized using any well-known method previously described. Following peptide synthesis, peptides can be analyzed to insure proper synthesis. For example, proper synthesis can be confirmed using mass spectrometry and/or purity of the peptides can be verified using reverse phase liquid chromatography.

Delivery Vehicles

Delivery vehicles are those formulations which in combination with the targeting peptides disclosed herein deliver the payload (e.g., therapeutic drug, protein or diagnostic compound) to a cardiovascular cell, such as a cell associated with an infarct border. The formulations can include, but are not limited to, liposomes, micelles, non-liposomal nanoparticles, nanoparticles made of drug, microbubbles, nanoparticles of polymer, metal oxide and/or lipid, dendrimers, and/or adeno-associated virus (AAV) vectors. Essentially any type of formulation that can be used to deliver a payload can be made to be specific with the selective approach discussed herein (the use of a peptide of Table 1 to target cardiac cells). Thus, term "delivery vehicle" refers to the vehicle itself, such as a liposome or an AAV vector, and also refers to a vehicle loaded with a payload (e.g., a pharmaceutic or diagnostic) and associated with targeting peptides.

Liposomes and Micelles

A liposome is a spherical vesicle having at least one lipid bilayer. Liposomes are most often composed of phospholipids, especially phosphatidylcholine, but may also include other lipids, such as egg phosphatidylethanolamine, so long as they are compatible with lipid bilayer structure. A liposome can include any suitable polymer, such as polymers that are currently in use or are being developed for controlled drug delivery in vivo. For example, the biodegradable polymer can be a polyester, a polylactone, a polycarbonate, a polyamide, or a polyol. The polyester can include of poly(lactic acid), commonly known as PLA, poly (glycolic acid), commonly known as PGA, and their copolymers, commonly known as poly(lactic-co-glycolic) acid or PLGA. Nanoparticles composed of PLGA can have any ratio of PLA and PGA, e.g., a lactic acid:glycolic acid ratio (e.g., molar ratio) of about 95:5 to about 5:95, such as about 75:25 to about 25:75, including about 50:50. The PLGA copolymer can be a random copolymer or block copolymer of lactic acid and glycolic acid. The block copolymers can have 2, 3, 4, or more blocks of PLA and PGA. The lactic acid component can be racemic, enantomerically enriched with the D or the L isomer, or enantiopure. A liposome design may employ surface ligands (e.g., targeting peptides) for attaching to unhealthy tissue.

The major types of liposomes are the multilamellar vesicle (MLV, with several lamellar phase lipid bilayers), the small unilamellar liposome vesicle (SUV, with one lipid bilayer), the large unilamellar vesicle (LUV), and the cochleate vesicle.

Liposome formation technology is well established in the art (liposomes can be created by sonicating a dispersion of amphipatic lipids, such as phospholipids, in water; they can also be created by other methods including, but not limited to, extrusion and Mozafari method). The liposomes can be prepared in any manner depending on the nature of components to be included. For example, the preparation methods for biodegradable microparticles can be used to prepare the liposomes of the invention. Most preparations are based on solvent evaporation or extraction techniques (see, for example, D. H. Lewis "Controlled Release of Bioactive Agents from Lactide/Glycolide Polymers" in Biodegradable Polymers as Drug Delivery Systems, Marcel Dekker, p. 1 (1990)). The simplest methods involve dissolving the polymer in an appropriate organic solvent and suspending this solution in an aqueous continuous phase which contains an appropriate surfactant. Continuous stirring then allows for evaporation of the organic solvent and hardening of the microparticles. The factors that control the size and size distribution of these particles are the polymer concentration in the solvent, the amount and type of surfactant, and the stirring rate. The solvents used in these techniques can include dichloromethane, acetone, methanol, ethyl acetate, acetonitrile, chloroform, and carbon tetrachloride.

In general, the inventive liposomes can be prepared by combining at least one of the inventive peptides, e.g., one or more peptides listed in Table 1, and other components of the liposome, such as phospholipids, in water to form a solution, and then manipulating the solution to form the liposome. Phospholipids suitable for use in the present invention can be natural phospholipids and/or can be purchased from commercial sources.

Micelles are also useful in the present invention.

In addition, the delivery vehicle can include additional components including hydrophobic or hydrophilic drugs, encapsulated in the micelle or liposome interior, or in the liposome bilayer. Various drugs conjugated to PEG or a lipid, such as a phospholipid, can also be incorporated into the nanoparticles (either as a cargo molecule or conjugated to a lipid).

The delivery vehicles include targeting molecules on their surfaces, such as those listed in Table 1 or derivative thereof. The peptides can be conjugated to the delivery vehicle in a two-step process. In the first step, the surfaces of the delivery vehicle are activated by suspending the delivery vehicles in borate buffer (50 mM, pH 5.0) by sonication for 30 sec on an ice bath. This is followed by the addition of DENACOL (40 mg), an epoxy that helps conjugation of the peptide on the surface, and the catalyst zinc tetrahydrofluroborate hydrate (50 mg), which are dissolved in an equal volume of buffer to the nanoparticle solution. This mixture can be stirred gently for example, for 30 minutes at 37° C. delivery vehicles can then be separated by ultracentrifugation for example at 30000 rpm for 20 minutes at 4° C. Any unreacted DENACOL can be removed by multiple wash steps.

In the second step, the peptide can be conjugated to the surface of the activated delivery vehicles by suspending the delivery vehicles in borate buffer (4 ml) and stirring into a solution containing an amount of the targeting peptides in borate buffer. This reaction can be carried out, for example, for 2 hours at 37° C. The unreacted peptide can then be removed by ultracentrifugation and the final delivery vehicle suspension can be lyophilized for 48 hours.

In various embodiments, the invention provides pharmaceutical compositions comprising a plurality of delivery vehicles and a pharmacologically acceptable excipient. The delivery vehicle may have a therapeutic agent coupled to the outer portion of the particle, as well as a targeting agent coupled to the surface. Administration of drug loaded or drug conjugated delivery vehicles can treat heart conditions/cells by contacting the tissue or cells and being taken up by the cells, and degrading to release the therapeutic agent(s).

For example, one embodiment relates to a method of delivering one or more active agents (e.g., a therapeutic and/or a diagnostic agent) to cardiac tissue of a subject. Systemic delivery of agents contained within a polymeric carrier nanoparticle conjugated to a targeting peptide having one or more sequences as provided in Table 1 enhances the uptake of the agents into cells of the cardiac tissue. It is contemplated that encapsulating a therapeutic and/or diagnostic agent of interest into a delivery vehicle (e.g., a PLGA polymeric nanoparticle) tagged with a targeting peptide can provide a targeting encapsulated active agent capable of homing to the cardiac tissue upon systemic administration to a subject. The targeting peptide, when conjugated to a delivery vehicle, such as a polymeric complex can direct the delivery vehicle (e.g., polymeric carrier nanoparticle composition) to the injured cardiovascular tissue, such as the myocardium. The delivery vehicle, such as the polymer, can then release the encapsulated active agent(s) into the area of injury. Thus, a delivery vehicle described herein can be used in a method of delivering a therapeutic and/or diagnostic agent to cardiac tissue of a subject. In some embodiments the composition is administered systemically.

A nanoparticle/delivery vehicle composition described herein can include a polymeric carrier and a therapeutic and/or diagnostic agent. Delivery vehicles can generally entrap or encapsulate the therapeutic and/or diagnostic agent in a stable and reproducible manner. The delivery vehicle composition is conjugated to a cardiac tissue targeting peptide described herein consisting of about 5 to about 25 amino acids or about 3 to about 7, including 5, 6 and/or 7 amino acids. At least a portion of the amino acid sequence of the cardiac tissue targeting peptide is homologous (identical) to at least 3, 4 or 5 consecutive amino acids of those peptides found in Table 1. In some embodiments, the cardiac tissue targeting peptide is selective for and targets a weakened, ischemic, and/or peri-infarct region of a subject's cardiac/myocardial tissue.

In some embodiments, the nanoparticle can be a particle of approximately spherical shape measuring less than about 1000 nm in diameter. In one embodiment, the nanoparticles can have a diameter of about 10 nm to about 1000 nm. In another embodiment, the nanoparticles can have a diameter of about 50 to about 500 nm, such as from about 100 to about 400 nm, and including from about 100 to about 250 nm.

Payload

A therapeutic or diagnostic agent, termed herein as a payload, delivered by a delivery vehicle can be any compound, agent or mixture. In some embodiments, the therapeutic agent includes one or more drugs (e.g., small molecules), proteins, peptides, cytokines, nucleic acids (including a gene coding for a protein), RNA, including shRNA, iRNA, microRNAs and/or antagomiRs, hormones, steroids, enzymes or mixtures thereof.

Gene Therapy

Gene therapy is a viable therapeutic regimen for many conditions. Originally, gene therapy was aimed at partial or total replacement of a diseased or mutated gene, and, thus, at reducing the pathological manifestations of this gene. In recent years a number of models for gene therapy against various pathological manifestations have been presented. These include gene replacement, gene therapy and oligonucleotide therapy (Brigham et al., 1993, Rosenecker et al., 1998). Several approaches for DNA transfection vectors have been used including various viruses' vectors and bacterial plasmid DNA (see review by Schreier, 1994).

The plasmid DNA transfection approach, using liposomes as the gene delivery system, has several advantages, especially when only transient (days or weeks) treatment is required. Among the advantages are convenience of use; pharmaceutical universality; safety (no viral structure is included and the natural phospholipids are non-immunogenic, a repeated administration can be safe for use as required); and shelf life (gene encapsulated liposomes can be lyophilized to achieve a prolonged shelf life (Allon et al., 1997). In addition, the bacterial plasmid DNA does not integrate with the host genome, and, thus, is not limited to a specific cell. This transient effect provides better control over the degree and duration of the expression.

The ability to prepare vectors/plasmids is known in the art.

In one embodiment, the therapeutic payload is a gene encoding a therapeutic protein such as VEGF, bFGF, and/or SDF-1. In this embodiment, the gene encoding the therapeutic protein may be contained in a plasmid.

In another embodiment, the therapeutic payload is an antisense oligonucleotide. As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

In another embodiment, the therapeutic payload is a therapeutic drug or protein. Therapeutic agents include, but are not limited to, anti-inflammatory agents, diuretics, vasodilators, angiotensin converting enzyme (ACE) inhibitors, angiotensin receptor agonists, beta-blockers such as certain angiogenic growth factors, p38 MAP kinase inhibitors, pro-angiogenic compounds, such as angiopoietin-1, RhoA, Rac1, VEGF and bFGF, IGF-1, adeno-cyclin A2, erythropoietin, ATP-sensitive potassium channel openers, antineoplastic agents, PARP-1 (Poly(ADP-ribose) polymerase 1) inhibitor AZ7379, hormones, analgesics, anesthetics, neuromuscular blockers, antimicrobials or antiparasitic agents, antiviral agents, interferons, antidiabetics, antihistamines, anticoagulants, small molecule drugs (including those that are <9 Daltons in molecular weight) and the like. Proteins, chemokines, and cytokines, that when administered to the target cells can include, for example: insulin-like growth factor (IGF)-1, sonic hedgehog (Shh), transforming growth factor $\beta$ (TGF-$\beta$); IL-I $\beta$, PDGF, VEGF (or 787, a PTK VEGFR2 inhibitor), TNF-a, PTH, thymosin $\beta$4, and/or hypoxia inducible factor la (HIF-1). In one embodiment, the payload comprises molecules for cardiac regeneration, angiogenesis promotion and/or proliferative agents. Of course, delivery vehicle, such as liposomes or micelles may include combinations of various encapsulated drugs, diagnostic compounds and various drug-conjugated lipids in their various compositions and formulations.

Diagnostic

A diagnostic agent included with the delivery vehicle or conjugated to a peptide of the invention can include any diagnostic agent used for in vivo contrast imaging such as myocardial contrast echocardiography (MCE) and other imaging modalities used to provide contrast in cardiovascular tissue such as computed tomography (CT), magnetic resonance imaging (MRI) coronary angiogram, electroanatomical mapping, fluoroscopy and single-photon emission computed tomography (SPECT). It will be appreciated that other imaging techniques that can define a weakened, ischemic, and/or peri-infarct region in a subject can also be used.

Diagnostic agents include rare earth metals such as manganese, ytterbium, gadolinium, europium, as well as irons, fluorophores (fluorescein, dansyl, quantum dots, and fluorocarbons).

Radionuclides are also useful both as diagnostic and therapeutic agents. Typical diagnostic radionuclides include 99mTc, 95Tc, mIn, 62Cu, 64Cu, 67Ga and 68Ga, and therapeutic nuclides include 186Re, 188Re, 153Sm, 166Ho, 177Lu, 149Pm, 90Y, 212Bi, 103Pd, 109Pd, 159 Gd, 140La, 198Au 199Au, 169Yb, 175Yb, 165Dy, 166Dy, 67Cu, 105Rh, mAg, and 192 Ir. Means to attach various radioligands to the delivery vehicles of the invention are understood in the art.

The therapeutic and/or diagnostic agent and delivery vehicle may be combined in a number of different ways depending upon the application of interest. For example, the therapeutic and/or diagnostic agent may be non-covalently associated with the delivery vehicle, e.g., nanoparticle, may be coupled to the delivery vehicle, e.g., nanoparticle, or may be coupled to the delivery vehicle, e.g., nanoparticle through spacer moieties or may not contain a delivery vehicle be associated with the peptide (optionally with a vehicle.

Pharmaceutical Formulations

The delivery vehicles described herein can be used to prepare therapeutic pharmaceutical compositions, for example, by combining the delivery vehicles with a pharmaceutically acceptable diluent, excipient, or carrier. The delivery vehicles described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The delivery vehicles described herein may be systemically administered in combination with a pharmaceutically acceptable vehicle, such as an inert diluent or an assimilable edible carrier. For oral administration, delivery vehicles can be enclosed in hard or soft shell gelatin capsules, compressed into tablets, or incorporated directly into the food of a patient's diet. Delivery vehicles may also be combined with one or more excipients and used in the form of ingestible tablets, buccal tablets, troches, capsules, elixirs, suspensions, syrups, wafers, and the like. Such compositions and preparations typically contain at least 0.1% of the delivery vehicles. The weight percentage of the delivery vehicles in the preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the delivery vehicles may be incorporated into sustained-release preparations and devices. The delivery vehicles may be administered intravenously or intraperitoneal by infusion or injection. Solutions of the delivery vehicles can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the delivery vehicles for the extemporaneous preparation of sterile injectable or infusible solutions or dispersions. The ultimate dosage form for injection or infusion should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the delivery vehicles in the required amount in the appropriate solvent or carrier with various other ingredients enumerated above, as required, optionally followed by filter sterilization. In the case of sterile powders for the preparation of sterile injectable solutions, methods of preparation can include vacuum drying and freeze drying techniques, which yield a powder of the delivery vehicles plus any additional desired ingredient present in the composition.

For topical administration, delivery vehicles may be applied in pure form or as a solution. However, it will generally be desirable to administer the delivery vehicles to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which delivery vehicles can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the delivery vehicles described herein where an ingredient of such compositions can optionally be replaced by a compound or composition described herein, or a compound or composition described herein can be added to the composition.

Useful dosages of the delivery vehicles described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of delivery vehicles required for use in treatment will vary not only with the particular active compound of the delivery vehicles but also with the route of administration, the nature of the condition being treated, and the age and condition of the patient, and will be ultimately at the discretion of an attendant physician or clinician.

The active compound of the delivery vehicles can be conveniently administered in a unit dosage form, for example, containing 5 to 1000 mg/m², conveniently 10 to 750 mg/m², most conveniently, 50 to 500 mg/m² of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Delivery vehicles, e.g., nanoparticles, loaded with a therapeutic and/or diagnostic agent conjugated to cardiac tissue targeting peptides can be administered systemically at a dose ranging from 10 µg of nanoparticles to 100 g of nanoparticles.

The delivery vehicles described herein can be effective in heart treatments and have higher potency and/or reduced toxicity as compared to the corresponding free active drug. The invention provides therapeutic methods of treating heart conditions in a mammal, which involve administering to a mammal having a heart conditions an effective amount of a delivery vehicles composition described herein. A mammal includes a primate, human, rodent, canine, feline, bovine, ovine, equine, swine, caprine, bovine and the like.

Treatment of Heart Conditions

The invention further provides methods for delivering a drug or other therapeutic to a cardiovascular cell/tissue, such as a heart cell/tissue, in vitro or in vivo, for example, in a patient. The invention also provides methods for treating heart conditions in a patient. The methods can include contacting a cardiovascular cell/tissue with a pharmaceutical composition described herein. The methods can also include administering to a subject in need of therapy an effective amount of a pharmaceutical composition described herein. The composition can include a drug-conjugated lipid or encapsulated drug or drug conjugated to a peptide, wherein the drug is effective for treating the heart conditions/disease, and wherein the composition may be taken up by cardiovascular cell/tissue, for example, in the subject, and the composition releases the drug to the heart cells.

The invention thus provides novel compositions as described herein. The invention further provides for the use of the compositions described herein for use in medical therapy. The medical therapy can be treating heart conditions, for example, to areas of the heart where cardiomyocytes have been disturbed due to infection, surgery or injury, such as by a heart attack. The treatment is directed to diseases/disorders associated with death of myocytes or other cardiovascular cells/tissues (e.g., the treatment of cardiovascular disease). These include, but are not limited to, cardiomyopathy, ischemic cardiomyopathy, ischemic cardiac disease, myocardial infarction (MI), cardiovascular disease, atherosclerosis, and/or myocarditis, such as viral myocarditis. The invention also provides for the use of a composition as described herein for the manufacture of a medicament to treat a disease in a mammal, for example, heart conditions in a human. The medicament can include a pharmaceutically acceptable diluent, excipient, or carrier.

As used herein the term "cardiomyopathy" refers to the deterioration of the function of the myocardium (i.e., the actual heart muscle) for any reason. Subjects with cardiomyopathy are often at risk of arrhythmia, sudden cardiac death, or hospitalization or death due to heart failure.

As used herein, the term "ischemic cardiomyopathy" is a weakness in the muscle of the heart due to inadequate oxygen delivery to the myocardium with coronary artery disease being the most common cause.

As used herein the term "ischemic cardiac disease" refers to any condition in which heart muscle is damaged or works inefficiently because of an absence or relative deficiency of its blood supply; most often caused by atherosclerosis, it includes angina pectoris, acute myocardial infarction, chronic ischemic heart disease, and sudden death.

As used herein the term "myocardial infarction" refers to the damaging or death of an area of the heart muscle (myocardium) resulting from a blocked blood supply to that area.

The following Examples are intended to illustrate the above invention and should not be construed as to narrow its scope. One skilled in the art will readily recognize that the Example suggests many other ways in which the invention could be practiced. It should be understood that numerous variations and modifications may be made while remaining within the scope of the invention.

EXAMPLES

Example 1

Materials and Methods
Lipids for Liposome Preparation 1,2-Dioleoyl-sn-glycerol-3-phosphocholine (DOPC), 1,2-dipalmitoyl-sn-glycerol-3 phosphocholine (DPPC), 1,2-disteroyl-sn-glycerol-3-phosphocholine (DSPC) cholesterol, 1,2-distearoyl-sn-glycero-3-phosphoethanolamine-N-[methoxy(polyethylene glycol)-2000 (DSPE-PEG$_{2000}$) and DSPE-PEG$_{3400}$-maleimide were purchased from Avanti polar lipids, Miami, Fla. 1,1'-Dioctadecyl-3,3,3'3'-tetramethylindotricarbocyanine iodide (DiR) was purchased from Invitrogen, Carlsbad, Calif. Peptides were synthesized using standard FMOC chemistry and Rink-Amide resin (Tufts University, Boston, Mass.).

FMT Imaging and Immunofluorescence in Heart Tissues

Phage clones from the in vivo screen were conjugated to the fluorophore VivoTag 680 (VT 680) using the monoreactive NHS ester of VT 680 (PerkinElmer, Waltham, Mass.) Immunohistochemistry for border zone cells was performed using the following antibodies: rat anti-mouse CD31 at 1:250 dilution (endothelial marker)(BD Biosciences, San Jose, Calif.), rat anti-mouse myoglobin at 1:200 (cardiomyocyte marker) (Santa Cruz Biotechnology Inc, Dallas, Tex.), anti-alpha-smooth muscle actin (aSMA) conjugated with Alexa Fluor 488 at 1:200 (myofibroblast marker) (Sigma Chemical Co., St. Louis, Mich.), rabbit anti-mouse c-Kit at 1:150 (cardiac progenitor cell marker) (Santa Cruz Biotechnology Inc, Dallas, Tex.), and goat anti-DDR2 at 1:200 (myofibroblast marker) (Santa Cruz Biotechnology Inc, Dallas, Tex.). In addition, extracellular matrix was identified by immunohistochemistry using anti-collagen 3 A at 1:200 dilution (Abcam, Cambridge, Mass.). Appropriate secondary antibodies were employed as needed to identify the primary antibodies:goat anti-rat Alexa Fluor 488 (1:250) (Abcam, Cambridge, Mass.), donkey anti-goat Alexa fluor 594 (1:200) (Life Technologies, Frederick, Md.) and goat anti-rabbit Alexa Fluor 488 (1:250) (Abcam, Cambridge, Mass.).

Induction of Reperfused MI in Mice

Male C57BL/6J mice (8-12 week old) were used for the in vivo screening of a phage display library. These same mice were also used to study the specificity of various phage clones after the third round of in vivo screen. The Ph.D-7 phage library (New England Biolabs, Ipswich, Mass.) was used for the first round of biopaning. Myocardial infarction in mice was induced by ligating the left anterior descending (LAD) artery for 40 minutes followed by reperfusion. Briefly, the mice were anesthetized with pentobarbital (100 μg/gram body weight), intubated, and mechanically ventilated with room air. The third and fourth ribs were cut to expose the heart and the pericardium was removed. The LAD was located and ligated with the help of a 7-0 silk suture. The suture was removed at the end of 40 min to allow for reperfusion, thus simulating the clinical standard of care. The chest was then sutured closed in multiple layers and the mouse was recovered with inhaled oxygen.

Phage Administration, Recovery and Consecutive Rounds of Biopanning

Four days post-MI, $1 \times 10^{12}$ phage clones from the phage library (Ph.D.-7, New England Biolabs) were injected intravenously into two mice and allowed to circulate for 4 h before the mice were euthanized. Phage titers were determined in 3 different regions of the left ventricle and in various other organs. Organs were weighed before they were lysed so that phage titer could be reported as percent injected dose/gram of organ. For each round of biopanning, $1 \times 10^{12}$ phage clones were injected. At the end of each round, phage recovered from border zone of the infarct were amplified in E. coli strain ER2738 and used for the next round of biopanning. For the second round of biopanning, phage from border region was pooled from 2 mice from round 1 and injected into mouse on day 4 post-MI. In the initial round of screening, TTC (triphenyltetrazolium chloride) was used to enhance differentiation between infarcted and viable myocardium. No adverse effects of TTC on phage infectivity or titer were detected, but TTC staining was not performed in the subsequent two rounds of biopanning since the infarct was visually apparent without staining at day 4 post-MI. In this study, the border zone was operationally defined as the 1-2 mm thick swath of viable myocardium surrounding the necrotic infarct zone.

Amplification and Titration of Phage from the Border Zone

Phage recovered from the border zone of the infarct were amplified with early-log phase ER2738 in LB media for 4.5 h, and then centrifuged to remove residual bacteria. The supernatant was mixed with PEG/NaCl (20% w/v polyethylene glycol-8000, 2.5 M NaCl in distilled water), incubated overnight at 4° C. and centrifuged to collect the amplified phage pellet. Collected phage were rinsed with PBS, precipitated with PEG/NaCl, and resuspended in PBS for the next round of biopanning Titers of the amplified phage pools were determined according to manufacturer's protocol. Percent inject dose (% ID) was calculated to determine phage enrichment from different regions of the infracted heart.

Final Amplification of Phage Clones and DNA Sequencing

Following the third and final round of selection, both the infarct and border zone tissues were amplified so that 50 phage clones from each tissue type could be selected for DNA sequencing of the peptide insert. Thus 50 phage clones from infarct region and 50 clones from the border region were selected for DNA sequencing. To determine the amino acid sequences expressed by the selected phage clones, the insert in the integrated section of the phage was amplified by direct polymerase chain reaction (PCR) with unique primer pairs: forward primer=5' CCTTTAGTGGTACCTTTCTAT 3' (SEQ ID NO:1), reverse primer=5' GCCCTCATAGT-TAGCGTAACG 3' (SEQ ID NO:2). DNA sequences were then determined at the DNA Sequencing Core (UVA) using the reverse primer and automated dideoxy sequencing. Peptide sequences were translated from DNA sequences and analyzed by alignment to known peptide sequences. Individual phage clones were pooled into groups of four based on peptide phylogeny for subsequent determination of affinity for the post-MI heart as determined by Fluorescence Molecular Tomography (FMT) imaging [12].

Figure 7A:
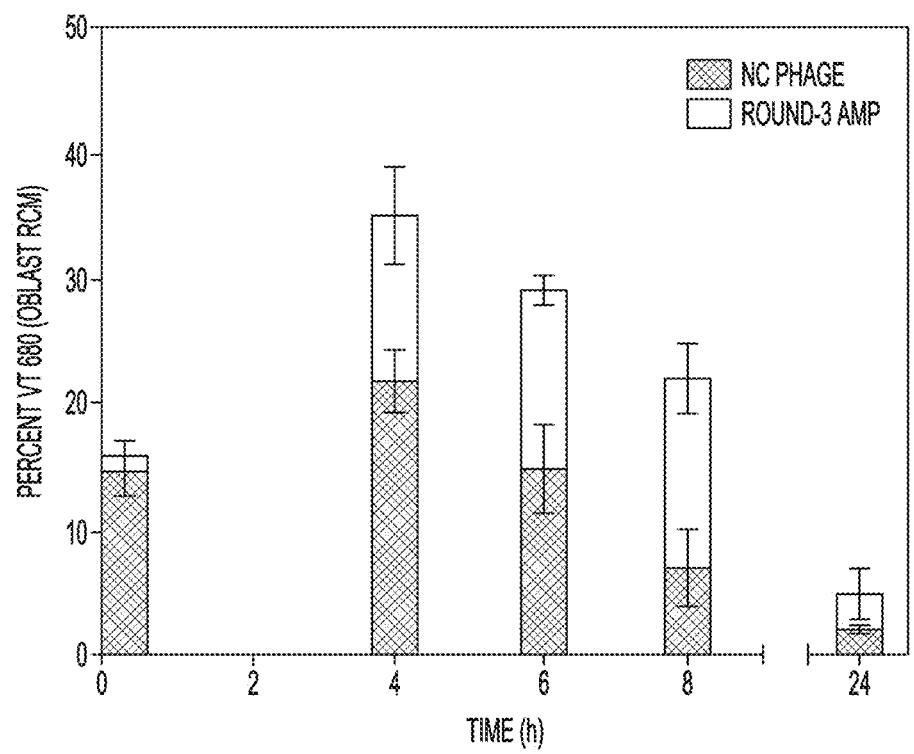
Figure 7B:
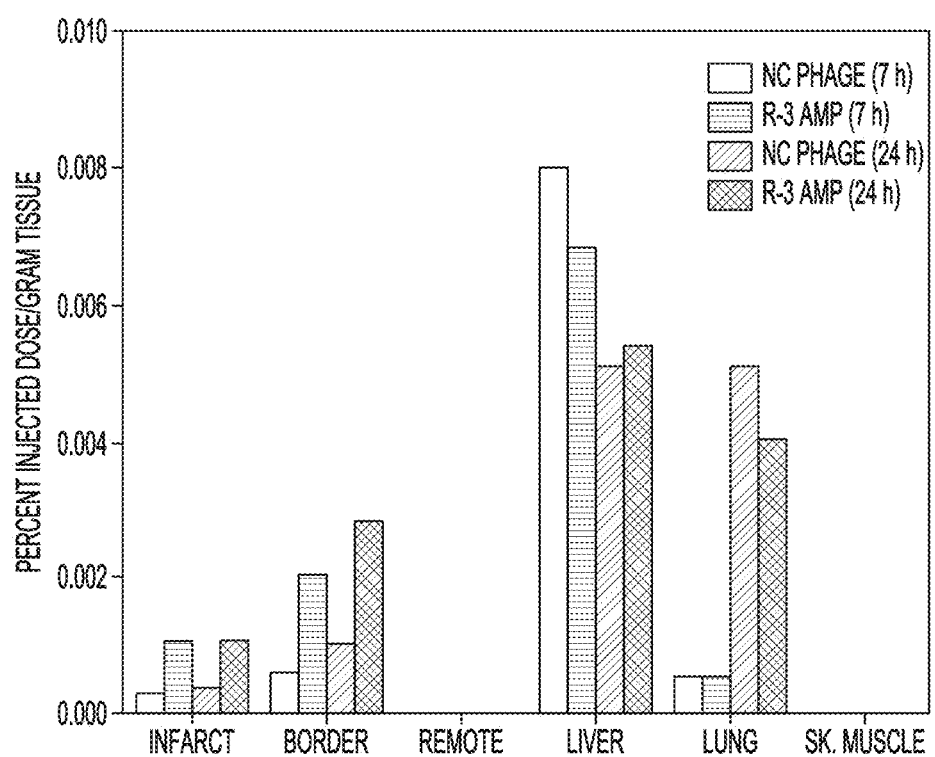

Assessing the Affinity of Round-3 Amplified Phage Clones for the Post-Infarct Heart After the third round of biopanning, FMT imaging was performed using round-3 amplified phage as compared to Panc-27 (negative control phage=NCP). NCP was an intentionally off-target peptide (Panc-27) (previously shown to be specific for pancreatic cancer cells) [13]. The objective of the FMT imaging was to confirm that the in vivo biopanning conducted 4 h post injection did indeed contain phage clones with affinity for the post-infarct heart. This was accomplished by using fluorescent phage to compare the distribution of NCP phage with that of the phage clone pools over time after injection in regions of interest (ROI) over the heart and liver. Phage clones from the in vivo screen were thus conjugated to fluorophore vivo tag 680 (VT 680) using the mono NHS ester of VT 680 (Perkin Elmer). In brief, approximately $1.5 \times 10^{12}$ phage particles were added to 12.5 μl of VT 680 NHS ester (10 mg/ml in DMSO). After 1 h at RT, the labeled phage was purified by PEG precipitation and there were about 430 dye molecules per round-3 amplified phage and 488 dye molecules per NCP phage. Six mice were then subjected to MI (40 min occlusion followed by reperfusion) and after 4 days, $7.5 \times 10^{11}$ of labeled phage particles were injected into 2 mice separately. Imaging (FMT 2500-PerkinElmer, Waltham, Mass.) was carried out to quantify phage particles in the heart (target) and liver (off-target) from animals from both groups every 2 h. One animal from each group of 2 was euthanized 7 h post injection and the other at the end of 24 h. The hearts and livers were also imaged ex vivo and phage titers were determined from the infarct and remote regions of the LV and 3 other organs including liver (FIG. 7B). A small fraction of the heart tissue was used for immunofluorescence and the rest was used for determining phage titer. Fluorescence intensities in ROIs over the heart were quantified using TrueQuant (PerkinElmer Inc, Waltham, Mass.) software and the same size/shape ROIs were used for image analysis at subsequent time points [12]. Three dimensional regions of interest (ROI) were manually segmented to define heart and liver. For visualization and analysis purposes, the FMT 2500 system software (TrueQuant) provided 3D images and total amount of fluorescence (in pmoles) in different organ sites that was automatically calculated relative to internal standards generated with known concentrations of appropriate FR/NIR dyes. Quantification by non-invasive FMT correlates well with both fluorescence from tissue homogenates as well as with ex vivo organ 3D images [12].

Specificity of Phage Clones by FMT

After sequencing, phage clones were grouped together (4 clones each group) based on their phylogeny using the Jotun Hein algorithm [14] and sequence similarity (FIG. 7A), which resulted in 23 groups. All 23 groups were screened for their heart/liver specificity as compared to the NCP negative control phage clone (Panc-27) by FMT imaging Each group of 4 clones was labeled with a near IR fluorescent dye (VT 680 from Perkin Elmer, Waltham, Mass.) and mixed with negative control phage clone (Panc-27) labeled with a second dye (VT 750). The specificity was determined by measuring heart:liver VT 680/heart:liver VT 750 at times 0.25 and 4 h post-injection on day 4 post-MI. The fluorescence intensity (VT 680) of each phage group was normalized by fluorescence intensity of the control phage clone Panc-27 (VT 750) to account for any variations in injected dose.

Immunofluorescence

Following ex vivo imaging of heart and liver, hearts from the mice under study were fixed in 4% paraformaldehyde for 1 h followed by equilibration in 30% sucrose for overnight at 4° C. The hearts were washed 3-4 times in DPBS (Dulbecco's phosphate-buffered saline) and placed in OCT medium (Sakura Finetek USA, Inc, Torrance, Calif.) and frozen by placing over liquid N2 vapors. The embedded tissue samples cut into 5-7 µm sections using a cryostat (Leica Microsystems Inc, Buffalo Grove, Ill.), for subsequent imaging with a fluorescence microscope fitted with appropriate filter sets (Olympus BX41). Cell types of interest in the infarct/border zone were identified by immunohistochemistry using the following antibodies: rat anti-mouse CD 31 at 1:250 dilution (endothelial marker)(BD Biosciences, San Jose, Calif.), rat anti-mouse myoglobin at 1:200 (cardiomyocyte marker) (Santa Cruz Biotechnology Inc, Dallas, Tex.), anti-alpha-smooth muscle actin (aSMA) conjugated with Alexa Fluor 488 at 1:200 (myofibroblast marker) (Sigma Chemical Co., St. Louis, Mo.), and rabbit anti-mouse c-Kit at 1:150 (cardiac progenitor cell marker) (Santa Cruz Biotechnology Inc, Dallas, Tex.). In addition, extracellular matrix was identified by immunohistochemistry using anti-collagen 3 A at 1:200 dilution (Abcam, Cambridge, Mass.). Appropriate secondary antibodies were employed as needed to identify the primary antibodies:goat anti-rat Alexa Fluor 488 (1:250) and goat anti-rabbit Alexa Fluor 488 (1:250) (Abcam, Cambridge, Mass.). Binding of I-1 and B-50 phage clones to cardiomyocytes and c-Kit+ cells was determined by flow cytometry. The RL-14 cardiomyocyte cell line (ATCC) was used to test the binding of fluorescently labeled I-1 phage (VivoTag 645) and myocardial infarct derived cardiac and bone marrow cells to test the binding of fluorescently labeled B-50 phage (VivoTag 680).

Preparation of Liposomes

Figures 3A, 3B, 3C:
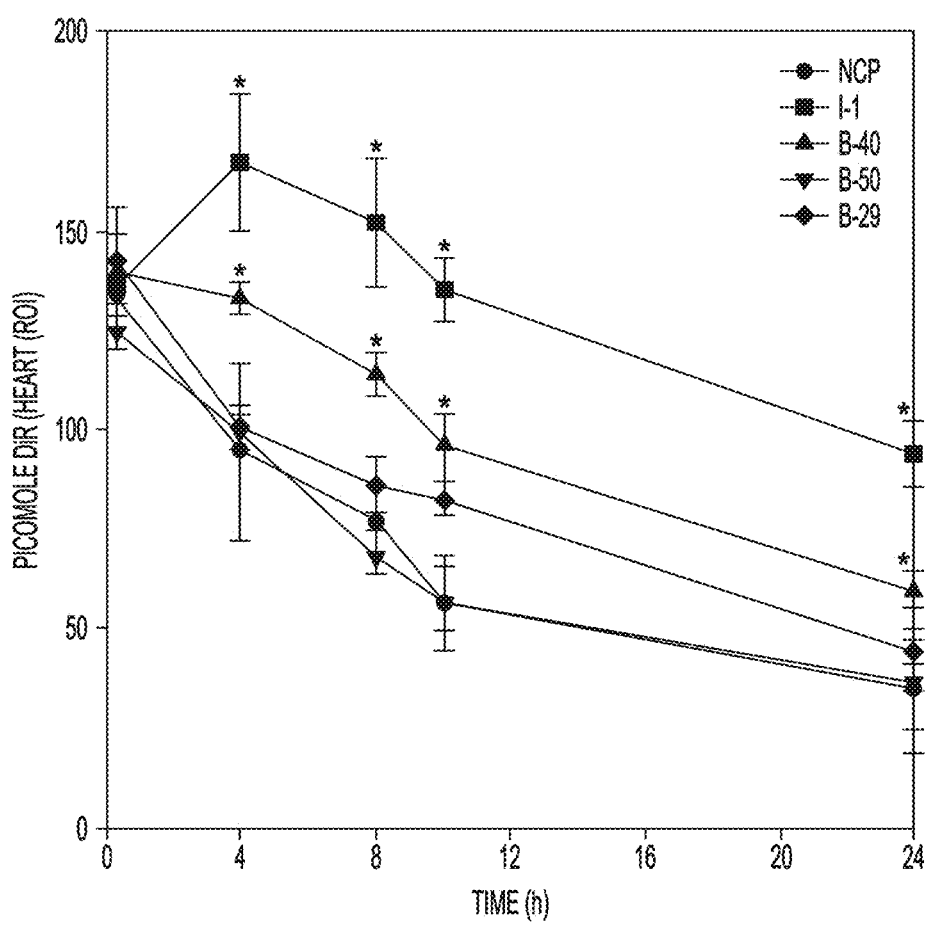
FIGS. 3A-F depict that peptide-modified liposomes are also specific for cell types of interest in the infarct/border zone. A) Table showing the ratio of lipid shell component including DiR (a lipophilic near infrared fluorophore). B) Using a two-compartment model fit, half-life and area-under-the-curve (AUC) were determined for the five different peptide-conjugated liposomes. C) Graph showing pharmacokinetics of five different peptide-conjugated liposomes obtained using FMT imaging followed by image analysis using the heart as the region of interest (ROI). FMT imaging of the liposomal preparations was performed in live mice (n=9) on day 4 post-MI. Liposomes displaying a negative control peptide (NCP) were included to compare random vs. targeted liposome kinetics. In this instance, targeted liposome accumulation was largely consistent with the density of available cellular targets. D) FMT images of 24 h post-MI mice injected with liposomes targeted to cell types of interest in the border zone. E) Percent injected dose of peptide conjugated liposomes from heart, liver and other tissues 24 h post-injected animals (n=9) suggested the specificity of peptides for infarct heart. I-1 liposomes were significantly higher in the heart compared to NCP liposomes (*indicates p<0.05 versus any other peptide in the same tissue by one way ANOVA analysis) (F) I-1 peptide-conjugated liposomes co-localize with cardiomyocytes present in the infarct border zone (top) and not with cardiomyocytes in the remote region (bottom). (Scale bar; 20 μm).
Figure 3D:
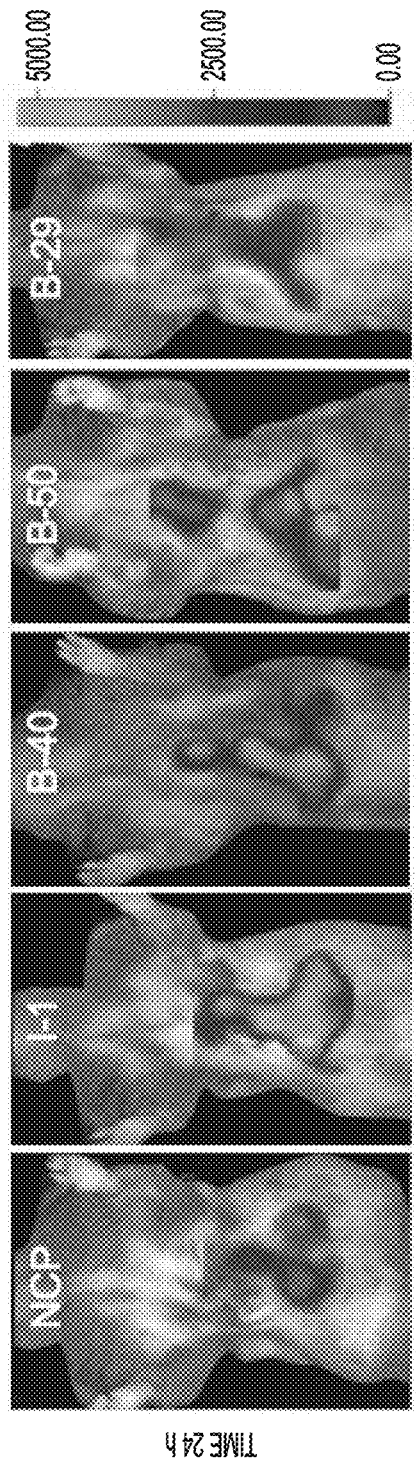

Peptides (7-mers) identified in the phage screen were chemically synthesized with the following modifications on the C-terminus: 7-mer-GGSK (FAM)C. The cysteine at the C-TERMINUS OF THE PEPTIDE WAS CONJUGATED TO DSPE-PEG$_{3400}$-MALEIMIDE AS FOLLOWS: DSPEPEG$_{3400}$-maleimide (9.5 mg) was first dissolved in 200 µl of methanol PBS/0.5 mM EDTA (800 µl) was then added to prepare the aqueous micellar solution. The peptides were immediately dissolved in the micellar solution of DSPE-PEG$_{3400}$-maleimide under argon. The reaction mixture was left at 4° C. overnight followed by dialysis in PBS (1×2 liters) followed by dialysis in water (2×2 liters), to remove free peptide and salts from the conjugated micelles. The purified peptide-PEG-DSPE was then lyophilized and this lipid powder was used in liposomal preparations. Liposomes were prepared by hydration of lipid film prepared with 1,2-dioleoyl-sn-glycerol-3-phosphocholine (Avanti Polar Lipids, Miami, Fla.) (DOPC):cholesterol:1,2-distearoyl-sn-glycero-3-phosphoethanolamine-N-[methoxy (polyethylene glycol)-2000 (DSPE-PEG$_{2000}$):DiR:DSPE-PEG$_{3400}$-peptide at 46:46:6:1:1 molar ratio (9.5, 4.5, 4.5, 1, and 0.5 mg, respectively) (FIG. 3A). 1, 1'-Dioctadecyl-3,3, 3'3'-tetramethylindotricarbocyanine iodide (DiR, Invitrogen, Carlsbad, Calif.) was incorporated into the lipid bilayer as a nonexchangeable fluorescent lipid dye that provided for FMT imaging of the peptide-conjugated liposomes in post-MI mice. The lipid mixture was dissolved in 1 ml of chloroform, dried using a rotary evaporator and left in a vacuum desiccator overnight to completely remove residual chloroform. Next day, the lipid film was hydrated with 1 ml of saline and the resulting lipid solution was extruded 41 times using a syringe extruder containing a 0.2 µm Nuclepore filter (Thermo Fisher Scientific Inc, Waltham, Mass.) [15]. The resulting liposomes were characterized by Nanosight NS300 (Malvern Instruments Ltd, Worcestershire, UK) to determine particle size and concentration. The absorbance of FAM on the peptides enabled the determination of the number of peptides that were incorporated in each liposomal formulation. Each of the peptide-conjugated liposomes was later injected via tail vein in post-MI mice to determine their pharmacokinetics using FMT imaging. Animals (n=8) were injected with 2 mg of lipid (100 µl containing 1×10$^{11}$ liposomes) and DiR present in heart ROI was imaged using the 750 nm laser of the FMT instrument. Following in vivo imaging, the cellular targets of peptide binding were determined by immunohistochemistry using antibodies recognizing various cell types of interest in the infarct/border zone. The presence of FAM on the peptides quickly enabled us to identify the cell types recognized by the peptide-targeted liposomes by co-localization with antibodies against CD31 (endothelial marker), α-smooth muscle actin (aSMA, myofibroblast marker), caveolin-3 (cardiomyocytes), and c-Kit (marker of progenitor cells). The extent of co-localization of FAM-labeled peptides with each of the antibodies was determined using JACoP plug-in in ImageJ software (National Institutes of Health, Bethesda, Md.). JACoP calculates Mander's overlap coefficient values from two fluorescent images that can be represented graphically in scatterplots where the intensity of one color is plotted against the intensity of the second color for each pixel, similar to the output provided for flow cytometry data. The scatterplots use Pearson's correlation coefficient (PCC) as a statistic for quantifying colocalization and values range from 1 (for two images where fluorescence intensities are perfectly, linearly related) to −1 (for two images where fluorescence intensities are perfectly, but inversely, related to one another). Values near zero reflect distributions of probes that are not correlated with one another [16].

Remote Loading

Different methods to separate and load the drug were carried out to determine the best loading procedure with least loss of drug and lipid (FIGS. 17-19). The structure of liposomes are various stages of remote loading are depicted in FIG. 20.

For remote loading of AZ7379, liposomes were prepared by reverse phase evaporation [15]. In brief, the lipid mixture was dissolved in 1 mL of chloroform and to this 3 mL of ethyl ether and 1 mL of 0.25 M ammonium sulfate solution was added. This lipid mixture was sonicated with a probe sonicator (XL2020, Misonix Inc, Farmingdale, N.Y.) to prepare water-in-oil emulsion, and with a help of a rotary evaporator, organic solvents were removed under vacuum. The volume of the resulting lipid slurry was then adjusted to 1 mL with water. Liposomes were prepared by passing through a 0.2 µm Nuclepore filter using a syringe extruder. Before remote loading, the ammonium sulfate present outside of the liposomes was removed by passing twice through size-exclusion, Zeba Spin desalting columns (Thermo Scientific, Rockford, Ill.). Zeba spin columns were washed three times with 10 mM HEPES buffer (pH 7.4) by spinning columns in a swinging bucket rotor at 1500×g for 1 min before loading ammonium sulfate liposomes. One-half mg of AZ7379 (2.5 mg/mL in 10 mM HEPES pH 7.4) was then incubated with 5 mg of lipid (20 mg/mL) at 55° C. for 1 h. The free drug was removed by passing through Zeba spin columns that were washed with 10 mM HEPES buffer, and the drug to lipid ratio for the purified liposomes was determined by HPLC using a combination of spectrophotometric and evaporative light scattering detectors.

AZ7379 Release Kinetics

The efficiency of remote loading was typically 100-120 µg of AZ7379 per mg of lipid and this was quantified by HPLC methods. The size and concentration of the liposomes was determined using Nanosight. This enabled one to quantify the amount of AZ7379 that was present in each of the liposomal formulations and at the same time to determine the number of peptides present in each preparation by measuring the absorbance at 480 nm. AZ7379-loaded liposomes were mixed with 50% fetal bovine serum in saline and the release was assessed at regular time points by measuring the amount of drug released into 50% FBS by HPLC. Release rates were plotted for each of the liposomal formulations as cumulative % release over time.

Ex Vivo Induction of PARP-1 and Pharmacodynamic Measurement (PD)

As PARP-1 activity on Day 4 post-MI as assessed by PAR accumulation was very little with about 5-6 cells per field (~150 cells) (data not shown), it became necessary to induce its activity ex vivo by incubating the heart tissue at room temperature in PBS for 90 min. Four groups of mice were examined (tail vein injections) (n=5 mice/group): the first group was injected with empty (drug-free) I-1 liposomes (1 mg lipid per mouse), the second with AZ7379 (100-120 µg per mouse) in 10 mM HEPES, the third with NCP liposomes loaded with AZ7379 (100-120 µg/mg lipid per mouse) and the fourth with I-1 liposomes loaded with AZ7379 (100-120 µg/mg lipid per mouse). After 24 h, mice were euthanized, hearts recovered, and 2 mm thick tissue slices were cut along the short axis near the apex of the heart. PARP-1 activity was induced in the tissue sections by incubation in saline for 90 min at room temperature. The 2 mm short-axis sections were then fixed in 4% paraformaldehyde and frozen in OCT so that 5 µm sections could be prepared using a cryostat. PARP-1 activity was assessed by quantitative image analysis as the percentage of poly (ADP-ribose) (PAR) positive nuclei present in the infarct and border zones. PAR accumulation was assessed in two 5 µm sections taken from either side of each 2 mm slice of tissue using antibody recognizing PAR (Abcam, Cambridge, Mass.). In the image analysis of each mouse, a total of six 60× images (~150 nuclei/field) and ten 20× images (~700 nuclei/field) were used for PAR quantification. Along with PAR, cardiomyocytes were identified by immunostaining for caveolin-3 (Abcam, Cambridge, Mass.) and macrophages by mac-2 (Cedarlane Labs, Burlington, N.C.). PAR+ nuclei in each group were quantified in the infarct and border zones. Using ImageJ, it was determined that total PAR+ nuclei located within either cardiomyocytes or macrophages and reported the results as percent PAR+ nuclei from all images examined.

Quantification of Lipids

Lipid concentrations were measured using an HPLC system (HP/Agilent 1040/1050) equipped with evaporative light-scattering detector (ELSD) (Varex MKIII, Alltech). Briefly, DOPC, DPPC, DSPC, Chol and PEG-conjugated lipids were separated at 40° C. on a C4 column (150 mm×4.6 mm; 5 mm; Phenomenex). The lipids were sequentially monitored using an ELSD. The ELSD conditions were as follows: the drift tube temperature was set at 90° C. and the airflow was 2.3 L/min. The flow rate was 1.0 mL/min for the mobile phases (mobile phase A, 2 mM ammonium acetate buffer (pH 4.0) and mobile phase B, 2 mM ammonium acetate in methanol). The mobile phase gradient condition was as follows: 8% A and 92% B at 0-2.5 mM, the binary linear gradient began from a mixture of 8% A and 92% B and ended at 3% A and 97% B in 1 min, and 3% A and 97% B was maintained for 1.9 min After that, the mobile phase composition changed back to its initial composition. Standard lipid solutions were prepared by dissolving each lipid in methanol. The liposome samples were directly diluted with methanol to the lipid concentration within the calibration range. The sample injection volume was 10 µL.

AZ7379 Quantification

AZ7379 was measured using HPLC under the following conditions. The separation was performed at 40° C. on a C8 solvent miser column (150 mm×2.1 mm; 5 mm; Alltech). The flow rate was 0.3 mL/min for the mobile phase, which consisted of buffers A (2 mM ammonium acetate buffer (pH 4.0) and B (2 mM ammonium acetate in methanol) in the ratio A/B=3/97 (encapsulation analysis) or 10/90 (release profile analysis). The sample injection volume was 5 (encapsulation analysis) or 20 µL (release profile analysis). The UV absorbance of AZ7379 was detected at 224 or 274 nm. AZ7379 concentration was calculated using a standard curve.

Statistical Analysis

All experiments were repeated at least three times, and statistical analysis of the data was performed by one-way analysis of variance (ANOVA). All data presented are expressed as mean±SD of at least three independent measurements. For all comparisons, $p<0.05$ was considered significant.

Results

Enrichment of Infarct/Border Specific Phage Clones

Figure 1B:
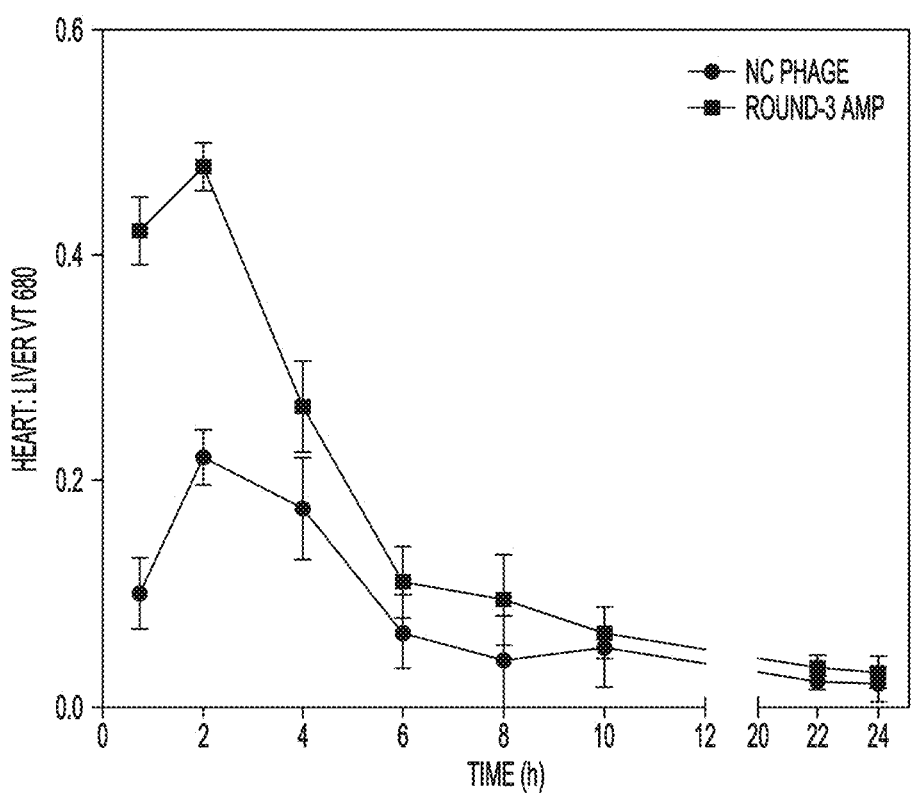

The Ph.D.-7 library ($1\times10^{12}$ pfu) was injected intravenously in mice on day 4 post-MI and was allowed to circulate for 4 h before animals were euthanized. The phage were recovered from the infarct, border and remote regions of the left ventricle and also from other organs including the liver to determine the selectivity of the phage pool for the infarct/border zone. The phage amplified from the border zone was used in subsequent rounds of biopanning for a total of 3 rounds of selection. The region of myocardium extending 1-2 mm from the outer edge of the infarct was considered as border zone. After the second round, a significant enrichment of phage clones specific for infarct (1.7% ID from round 1 vs. 7.2% ID from round 2) was noted, along with a very small increase in phage specific for the border region (1.9% ID vs. 2.1% ID). In the third round, no further enrichment of phage clones specific for either the border zone (2.1% ID from round 2 vs. 1.1% ID from round 3) or the infarct zone (7.2% ID from round 2 vs. 3.2% ID from round 3) was observed. This suggested that 2 rounds of biopanning were enough to obtain phage clones specific for the infarct heart unlike other targets that may require 3-4 rounds of biopanning. Phage clones accumulating in the liver decreased between each of the three rounds. To further test the specificity of the phage for infarct/border zone, FMT imaging was performed using the round 3 amplified phage pool and negative control phage clone (Panc-27, a phage clone specific for plectin [17, 18]) conjugated to VT680 in mice on day 4 post-MI. It was observed that at 2 hours post injection, the round 3 amplified phage pool had a two-fold higher specificity for the post-MI heart (as assessed by heart:liver ratio) when compared with the Panc-27 phage bearing the negative control peptide (NCP, see FIG. 1B).

Figure 1C:
Figure 1D:
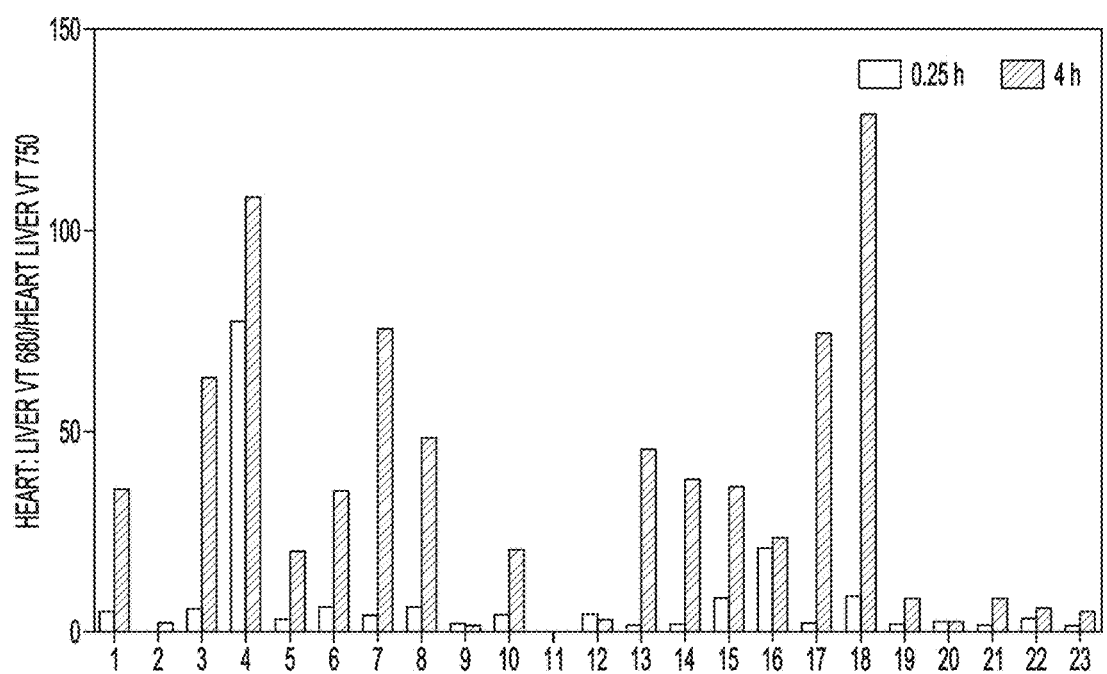
Figure 1E:
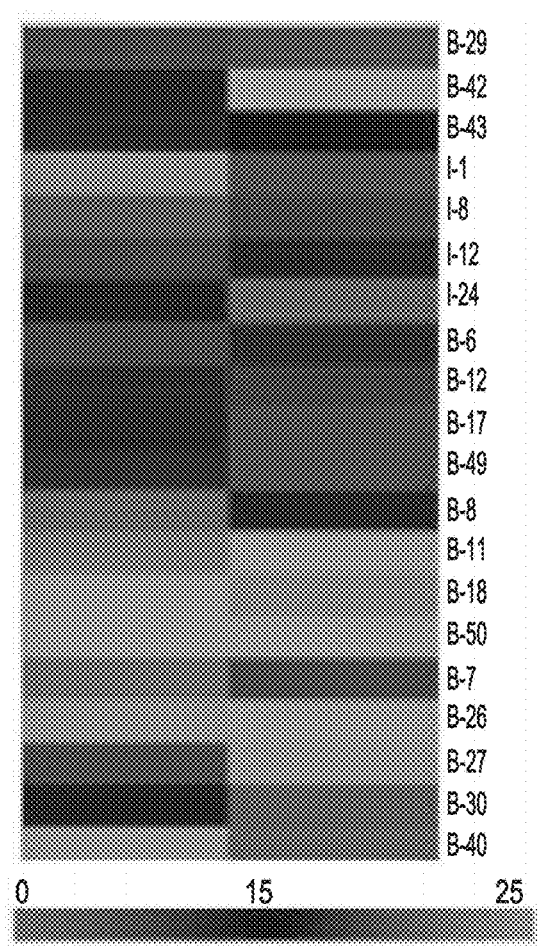
Figure 1F:
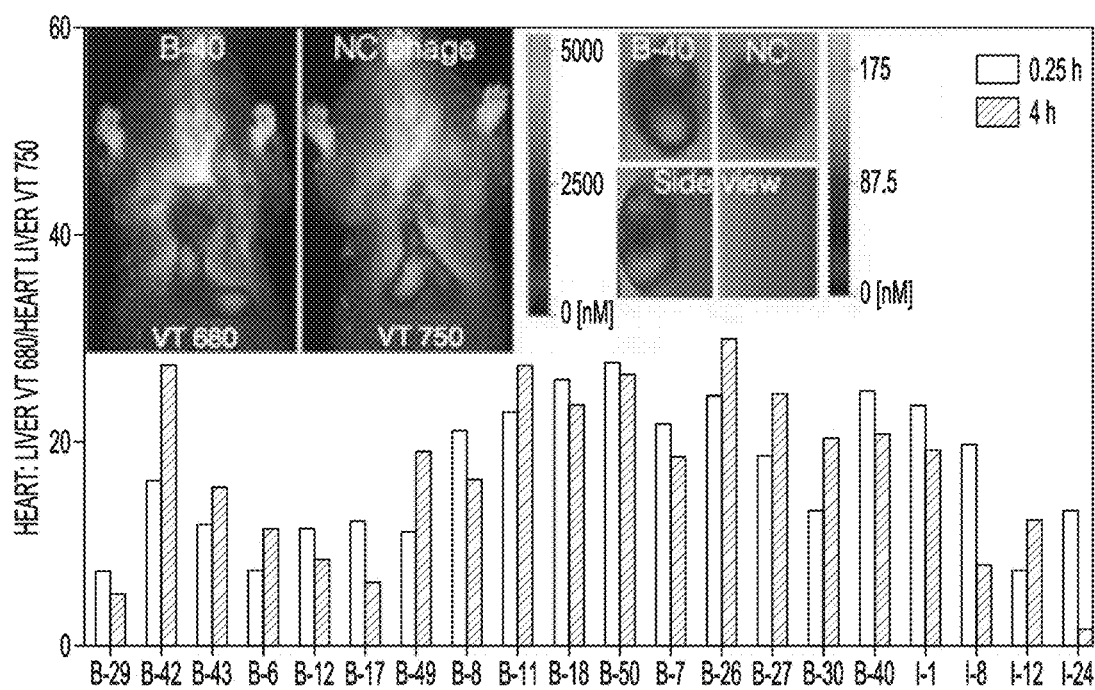

To expedite the screening of specific clones, phage clones were then grouped (4 clones/group) based on their phylogeny using the Jotun Hein algorithm and sequence similarity (FIG. 7A), which resulted in 23 groups that were each subject to a second round of FMT analysis. Eleven of 23 groups (44 clones) demonstrated high levels of specificity (heart to liver FMT ratios greater than 20, see FIGS. 1C and E). A total of 27 individual clones from these groups were subsequently screened individually for their specificity for the post-infarct heart (FIG. 1F). Of the 27 phage clones that were individually screened, 7 phage clones that were identified as rapid amplifiers due to known amplification bias (clones marked red in FIG. 7) and these clones were excluded from further analysis. The specificities of the remaining 20 phage clones are reported in FIGS. 1D and 1F. Interestingly, some of these phage clones showed evidence of specific binding within 15 minutes post injection. After in vivo FMT analysis, animals were euthanized and hearts were explanted for ex vivo imaging via FMT (FIG. 1F). Ex vivo analysis revealed a focal accumulation of the phage clones in the apical anterior left ventricle, indicating that phage clones were specific for the infarct/border zone region with less uptake in remote regions of the heart (FIG. 1F). Quantification by non-invasive FMT correlates well with both fluorescence from tissue homogenates as well as with ex vivo organ 3D images [12].

Identification of Phage Clones Specific for Cell Types of Interest

Figure 8A:
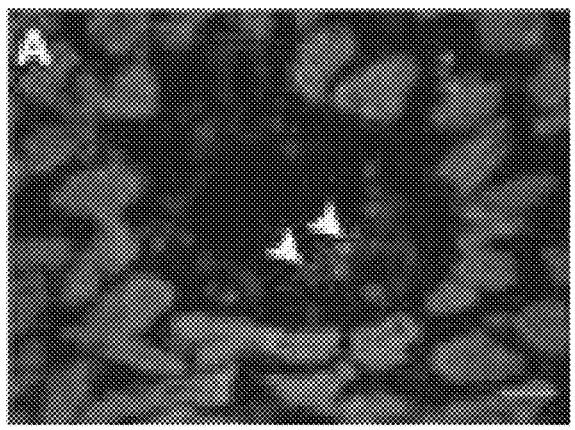
Figure 8B:
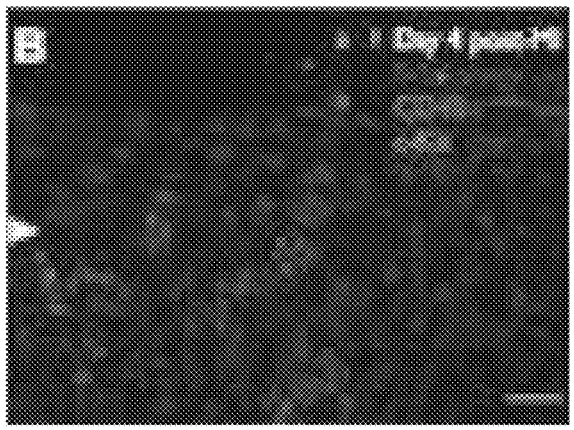
Figure 8C:
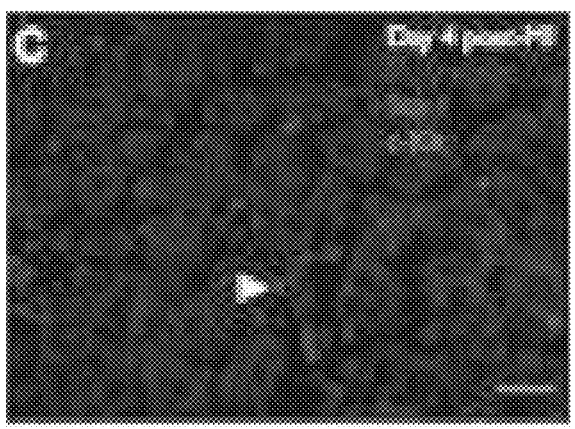
Figure 8D:
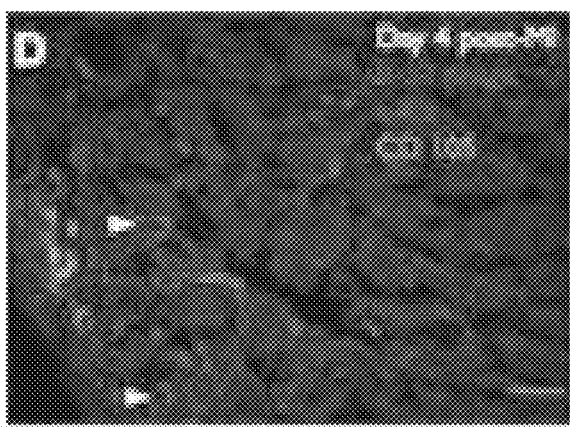
Figure 8E:
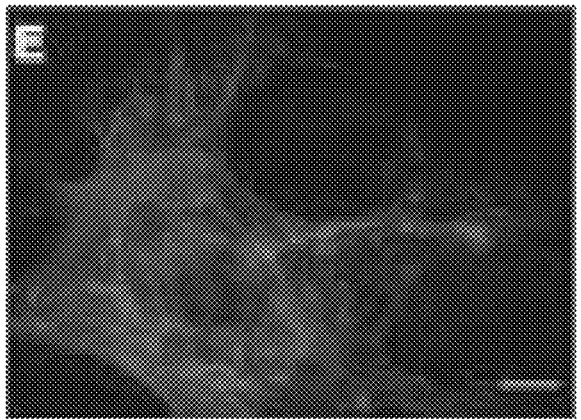
Figure 8F:
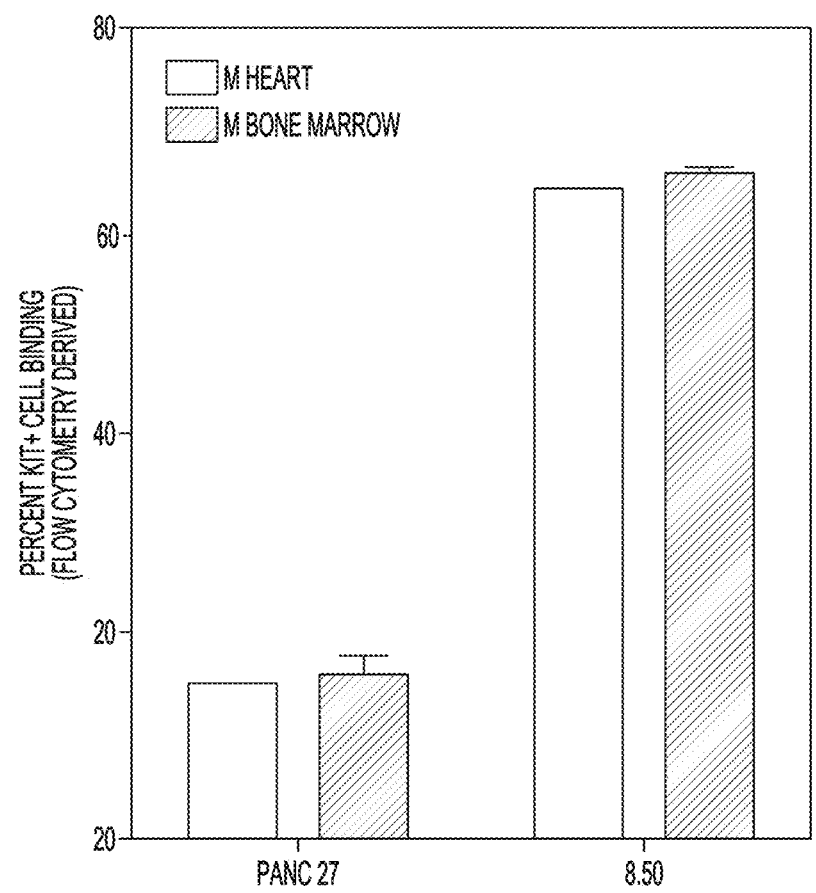
Figure 8G:
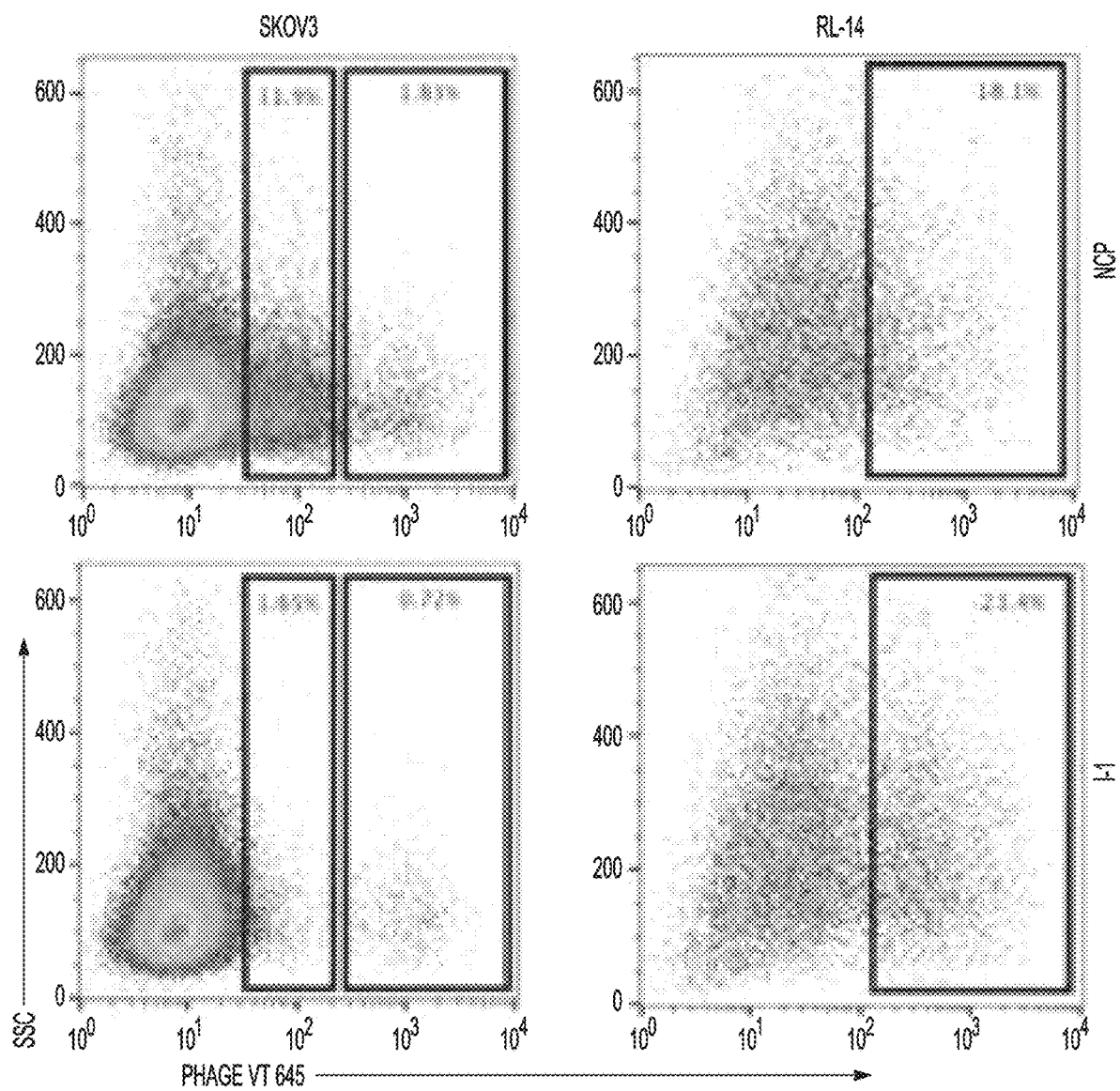
Figures 9A, 9B:
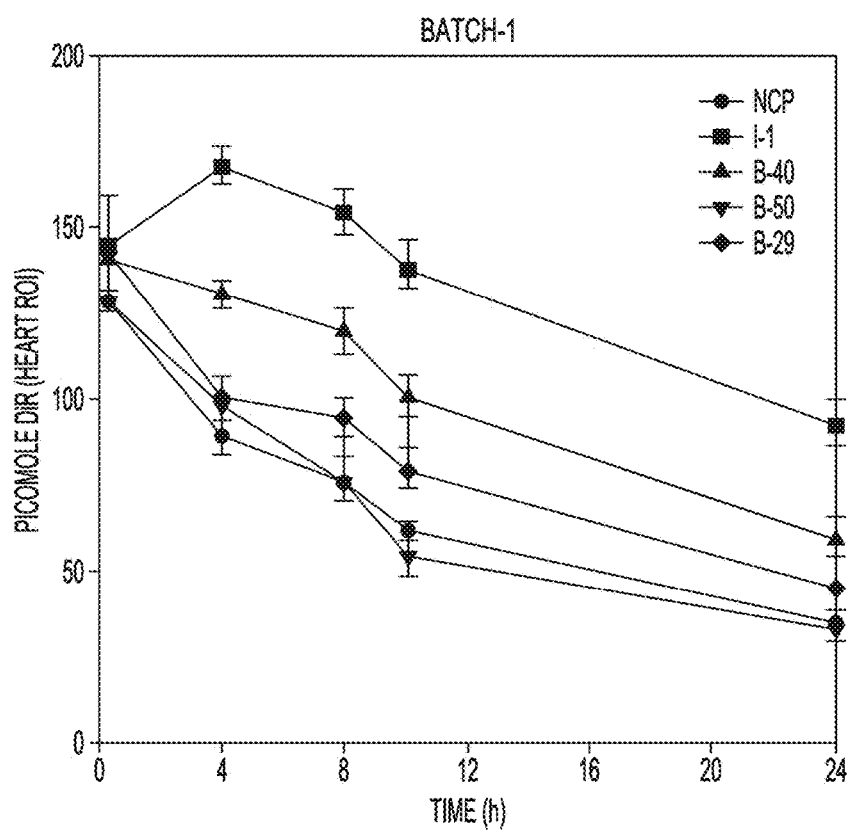
Figure 9C:
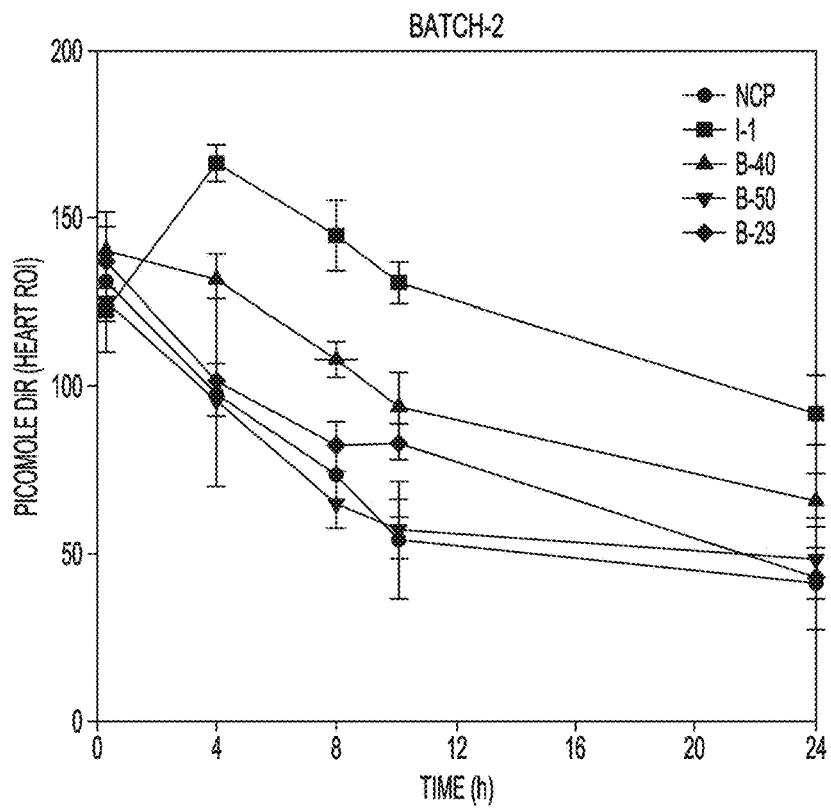
Figure 9D:
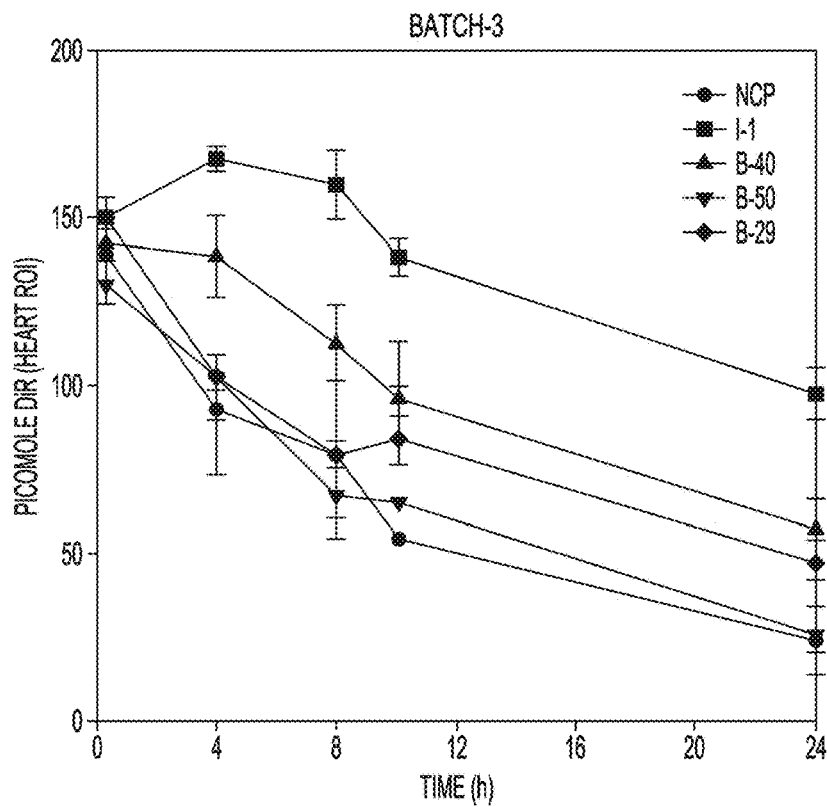

Following the in vivo screen of individual clones via FMT imaging, heart tissue sections were immunostained with antibodies specific for cell types of interest in the infarct/border zone (FIG. 2). Using this approach, phage clones were identified with specificity for endothelial cells (clones B-40, B-47), cardiomyocytes (clones I-1, B-42), myofibroblasts (clones B-7, B-29), c-Kit+ cells (clones B-50, B-27) and extracellular matrix (clones B-11, B-43) present in the infarct/border zone. The ability of I-1 phage to bind to cardiomyocytes was confirmed by in vitro incubation of the cell line RL-14 and fluorescent phage followed by flow cytometric analysis. The ability of the B-50 phage clone to bind to c-Kit+ cells was also confirmed by performing flow cytometry on cells isolated from Day 4 post-MI hearts and bone marrow (FIG. 8). The results presented in FIG. 8D are an average of three flow cytometry experiments using cells isolated from Day 4 post-MI hearts and bone marrow. Control and B-50 phage were fluorescently labeled with VT 680 and c-Kit+ cells were identified using c-Kit antibody conjugated with Alexa Fluor 488. Flow cytometry indicated that B-50 phage were specific for c-Kit+ cells isolated from heart and bone marrow.

Specificity and Pharmacokinetics of Peptide-Conjugated Liposomes

Peptide-conjugated liposomes were prepared and their pharmacokinetics studied (FIG. 3). The size of the peptide conjugated liposomes prepared by the hydration method ranged from 100-120 nm and the number of peptides per liposome ranged from 500-800 per liposome (FIG. 9 and Table 1). All the peptides used in this study had a charge of +2. For the pharmacokinetic experiments, 2 mg ($1 \times 10^{12}$) of liposomes were injected into mice and animals were imaged at the indicated time points to determine liposome specificity for the post-infarct heart using FMT. As the liposomes were labeled with DiR, FMT imaging was also used to quantitate liposomes in the heart by ROI analysis. The pharmacokinetics and accumulation were fit using a two-compartment model (FIG. 3). Pharmacokinetics were measured in at least 9 animals for each liposome type prepared from three different batches (FIG. 9) and the results indicated that the density of peptides used in these experiments (between 500-800 peptides/liposome) did not significantly alter pharmacokinetics. After pharmacokinetics, biodistribution experiments were performed.

Figure 3F:
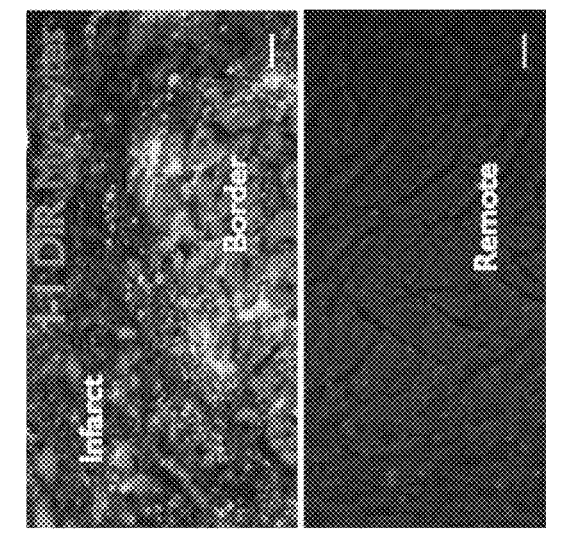
Figure 3E:
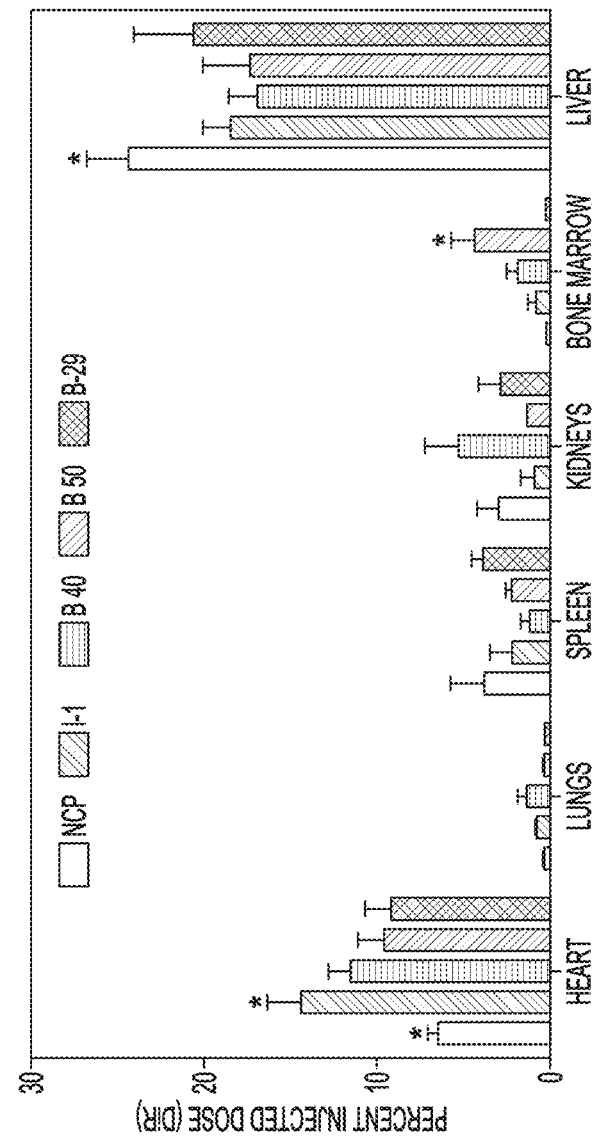
Figure 6A:
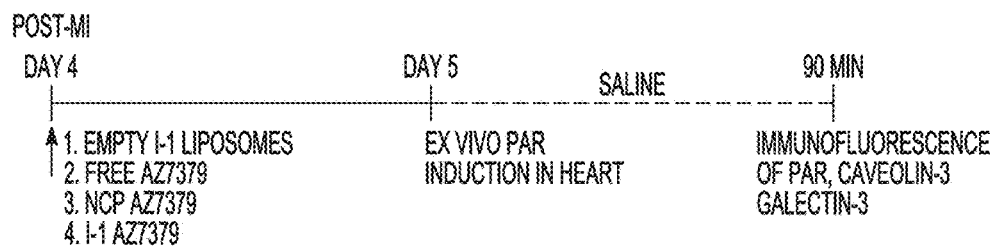
Figure 6B:
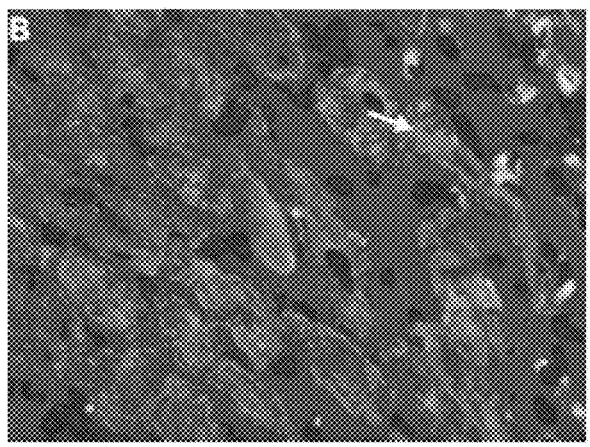
Figure 6C:
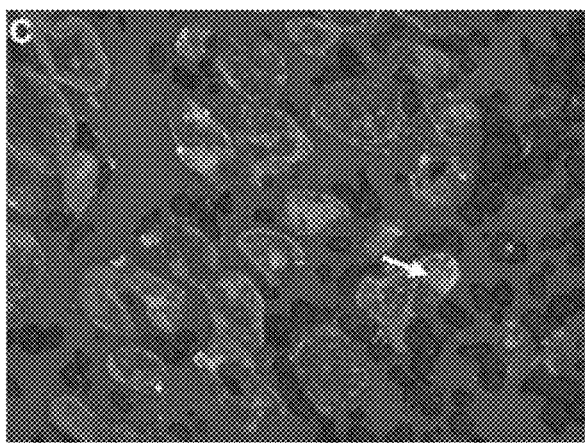
Figure 6D:
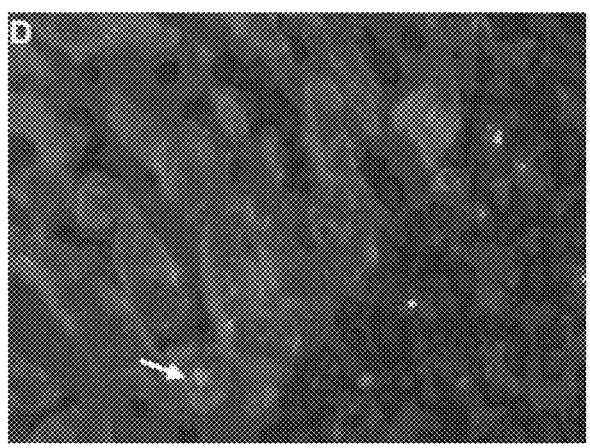
Figure 6E:
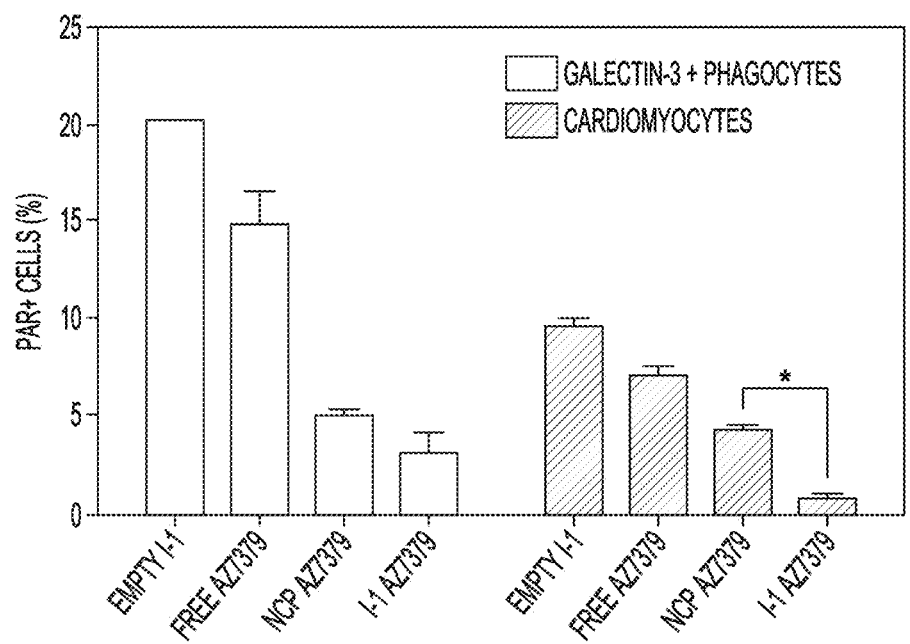

The biodistribution of peptide-conjugated liposomes 24 h post-injection suggest that peptide-conjugated liposomes have higher accumulation in the post-infarct heart than NSP-liposomes. As expected, organs of the reticuloendothelial system (liver and spleen) also accumulated liposomes, as has been reported previously [19-24]. NCP-liposomes had significantly higher accumulation in the liver than the cardiac-targeted peptide-conjugated liposomes, indicating that a shift in distribution away from the liver towards the post-infarct heart as a result of peptide targeting. Intriguingly, B-50 liposomes also accumulated in the bone marrow—confirming the phage-based experiments that demonstrated binding of the peptide to c-Kit+ cells from bone marrow (FIG. 8). Consistent with the phage display screen, all of the peptide-conjugated liposomes were found only in the infarct and border zones, while essentially no liposomes could be detected in the remote region of the heart, as illustrated using liposomes targeted with the I-1 peptide (FIG. 3F). The specificities of four of these peptides for the corresponding target cell types were then systematically validated through immunofluorescence analysis of post-infarct heart tissue samples collected 4 h post injection. The presence of the FAM fluorophore on the peptide in each liposome construct enabled visualization of the cellular target in the post-infarct heart using fluorescence microscopy. The tissue sections were co-stained with antibodies specific for cell types of interest present in the infarct/border zone. Using the ImageJ plug-in JACoP, it was determined that the Mander's overlap coefficient, which describes the extent of overlap between the peptide and the cell type marker. From this analysis, it was possible to conclude that these peptides could improve liposome targeting of endothelial cells, cardiomyocytes, and c-Kit+ cells by 2-3 fold as compared to other cell types (FIG. 4A-E). Since there is no target for the NCP in the post-infarct heart, the non-targeted liposomes are readily taken up by macrophages, a finding congruent with previous publications [25-27]. The overall goal of this project was to shift the cellular localization of the liposomes away from macrophages towards other cell types of interest in the post-infarct heart. By using the I-1 peptide, the liposomes were shifted away from macrophages and towards cardiomyocytes. As seen in FIG. 4F the immunofluorescence data and statistical analysis using Mander's overlap coefficient provide evidence to support this shift in cell binding. The majority of I-1 targeted liposomes were associated with cardiomyocytes, but not exclusively.

TABLE 1

| | Top 92 peptides from initial screen including parasitic sequences | | Top 158 peptides from next-gen sequencing of phage from first round of biopanning | |
|---|---|---|---|---|
| Designation | Peptide Sequence | | Peptide Sequence | Copy # |
| B-9 | NQLPLHA | (SEQ ID NO: 3) | NQLPLHA (SEQ ID NO: 3) | *8939* |
| I-20 | FPSTITP | (SEQ ID NO: 4) | ASVHLPP (SEQ ID NO: 97) | 8166 |
| I-46 | QPWPTSI | (SEQ ID NO: 5) | ANTTPRH (SEQ ID NO: 98) | 7490 |

TABLE 1-continued

| | Top 92 peptides from initial screen including parasitic sequences | | Top 158 peptides from next-gen sequencing of phage from first round of biopanning | |
|---|---|---|---|---|
| Designation | Peptide Sequence | | Peptide Sequence | Copy # |
| B-29 | RPPALAP (SEQ ID NO: 6) | | QNSQLSR (SEQ ID NO: 99) | 6501 |
| B-26 | SHPASHD (SEQ ID NO: 7) | | LPSYHVP (SEQ ID NO: 100) | 6192 |
| B-43 | ESRQVTP (SEQ ID NO: 8) | | WPTPPYA (SEQ ID NO: 101) | 5521 |
| B-18 | DPRATMY (SEQ ID NO: 9) | | FPSTITP (SEQ ID NO: 4) | 5496 |
| B-22/B-40* | SLLNRMP (SEQ ID NO: 10) | | VQTYARV (SEQ ID NO: 102) | 4698 |
| I-30 | LTPVPGQ (SEQ ID NO: 11) | | ITAPHPH (SEQ ID NO: 103) | 4238 |
| B-1 | HFYPSLL (SEQ ID NO: 12) | | YRAPWPP (SEQ ID NO: 104) | 4049 |
| B-10 | HSVPTPT (SEQ ID NO: 13) | | ATLTHPP (SEQ ID NO: 105) | 3952 |
| B-11 | TMQHDG (SEQ ID NO: 14) | | TAPSARH (SEQ ID NO: 106) | 3724 |
| B-12 | SAPGSSP (SEQ ID NO: 15) | | HKYISAT (SEQ ID NO: 107) | 3231 |
| B-15 | RMSPYDA (SEQ ID NO: 16) | | QSPDEVW (SEQ ID NO: 108) | 3150 |
| B-17 | YATQSSP (SEQ ID NO: 17) | | TDSLRLL (SEQ ID NO: 109) | 3084 |
| B-19 | ATNGFAQ (SEQ ID NO: 18) | | QPWPTSI (SEQ ID NO: 5) | 3020 |
| B-21 | LQPPHAK (SEQ ID NO: 19) | | AFPVSHN (SEQ ID NO: 110) | 3016 |
| B-24 | TLLPTSH (SEQ ID NO: 20) | | AAGQQFP (SEQ ID NO: 111) | 3003 |
| B-25 | TVVPKAT (SEQ ID NO: 21) | | GPMLARG (SEQ ID NO: 112) | 2945 |
| B-27 | SHSNARS (SEQ ID NO: 22) | | HTIQFTP (SEQ ID NO: 113) | 2938 |
| B-28 | SPQITRL (SEQ ID NO: 23) | | SPQMTLS (SEQ ID NO: 114) | 2877 |
| B-30 | LPLNSHS (SEQ ID NO: 24) | | TIPSRVL (SEQ ID NO: 115) | 2858 |
| B-31 | FSPFRHV (SEQ ID NO: 25) | | ELSSQLA (SEQ ID NO: 116) | 2782 |
| B-32 | DISSHAR (SEQ ID NO: 26) | | SEPGRSL (SEQ ID NO: 117) | 2768 |
| B-37 | SPQWRSS (SEQ ID NO: 27) | | SSLPLRK (SEQ ID NO: 118) | 2740 |
| B-38 | LQGPTQV (SEQ ID NO: 28) | | ACASNKS (SEQ ID NO: 119) | 2721 |
| B-39 | TPSSSLE (SEQ ID NO: 29) | | AMSSRSL (SEQ ID NO: 120) | 2699 |
| B-41 | HQENTKL (SEQ ID NO: 30) | | AAKTPTE (SEQ ID NO: 121) | 2594 |
| B-42 | AMRPPLN (SEQ ID NO: 31) | | TMPGKTS (SEQ ID NO: 122) | 2549 |
| B-44 | STLKAPG (SEQ ID NO: 32) | | APPTRYH (SEQ ID NO: 123) | 2460 |
| B-45 | TAQPRLI (SEQ ID NO: 33) | | ALNSLTN (SEQ ID NO: 124) | 2451 |
| B-46 | EVYAPPR (SEQ ID NO: 34) | | QVQTHHN (SEQ ID NO: 125) | 2373 |
| B-47 | ATMSRAP (SEQ ID NO: 35) | | ALHSARV (SEQ ID NO: 126) | 2359 |
| B-49 | TPGGKSP (SEQ ID NO: 36) | | QAPSRTH (SEQ ID NO: 127) | 2348 |
| B-5 | YNYGTLV (SEQ ID NO: 37) | | NTSAVSV (SEQ ID NO: 128) | 2338 |
| B-50 | GLSQLQR (SEQ ID NO: 38) | | ALIPKPR (SEQ ID NO: 129) | 2301 |
| B-6 | YPNHASP (SEQ ID NO: 39) | | TSPTSFD (SEQ ID NO: 130) | 2216 |
| B-7 | SDTWSSR (SEQ ID NO: 40) | | KWPLSHP (SEQ ID NO: 131) | 2176 |
| B-8 | TLAQIHH (SEQ ID NO: 41) | | AGNGTTP (SEQ ID NO: 132) | 2156 |
| I-1 | TALPRLN (SEQ ID NO: 42) | | FPGRPSP (SEQ ID NO: 133) | 2149 |

TABLE 1-continued

| | Top 92 peptides from initial screen including parasitic sequences | Top 158 peptides from next-gen sequencing of phage from first round of biopanning | |
|---|---|---|---|
| Designation | Peptide Sequence | Peptide Sequence | Copy # |
| I-10 | RDLQRPY (SEQ ID NO: 43) | THLPWQT (SEQ ID NO: 134) | 2141 |
| I-11 | QTAHHVQ (SEQ ID NO: 44) | ATPLWLK (SEQ ID NO: 135) | 2123 |
| I-12 | SALPNLY (SEQ ID NO: 45) | VYPHPER (SEQ ID NO: 136) | 2104 |
| I-13 | SVRTLQA (SEQ ID NO: 46) | NQLTTLN (SEQ ID NO: 137) | 2093 |
| I-14 | ELHKPQH (SEQ ID NO: 47) | ATSIRYT (SEQ ID NO: 138) | 2084 |
| I-15 | TAQTISD (SEQ ID NO: 48) | STIHGST (SEQ ID NO: 139) | 1961 |
| I-2 | AADMVVF (SEQ ID NO: 49) | KSYVSPS (SEQ ID NO: 140) | 1941 |
| I-23 | SSVSLES (SEQ ID NO: 50) | SPSMLQK (SEQ ID NO: 141) | 1917 |
| I-24 | AITTRHQ (SEQ ID NO: 51) | GTWLSRG (SEQ ID NO: 142) | 1904 |
| I-26 | YDYSASS (SEQ ID NO: 52) | SVESAWR (SEQ ID NO: 143) | 1885 |
| I-29 | NLPHRTS (SEQ ID NO: 53) | QNGGPSV (SEQ ID NO: 144) | 1873 |
| I-32 | ANRLLTP (SEQ ID NO: 54) | STDKVPL (SEQ ID NO: 145) | 1811 |
| I-33 | WQYPSRA (SEQ ID NO: 55) | SPTGWAP (SEQ ID NO: 146) | 1799 |
| I-34 | YVQGTAS (SEQ ID NO: 56) | QRLPQTA (SEQ ID NO: 147) | 1785 |
| I-37 | HQVPHSM (SEQ ID NO: 57) | HVVSPPP (SEQ ID NO: 148) | 1782 |
| I-38 | STYTVSS (SEQ ID NO: 58) | TITNPRP (SEQ ID NO: 149) | 1770 |
| I-4 | LTTDWTS (SEQ ID NO: 59) | TQYFYLP (SEQ ID NO: 150) | 1756 |
| I-40 | QACELSL (SEQ ID NO: 60) | GNTPSRA (SEQ ID NO: 151) | 1754 |
| I-42 | SLGARTP (SEQ ID NO: 61) | TDTESKR (SEQ ID NO: 152) | 1752 |
| I-47 | FQDQHPQ (SEQ ID NO: 62) | WVPSTWG (SEQ ID NO: 153) | 1729 |
| I-49 | FDAINQP (SEQ ID NO: 63) | HRADMHF (SEQ ID NO: 154) | 1698 |
| I-7 | AAHALMK (SEQ ID NO: 64) | YQLTSSL (SEQ ID NO: 155) | 1693 |
| I-8 | TSLSDSQ (SEQ ID NO: 65) | WTPSVRP (SEQ ID NO: 156) | 1670 |
| I-17 | HAIYPRH (SEQ ID NO: 66) | NKNYIQH (SEQ ID NO: 157) | 1648 |
| I-16 | YLTMPTP (SEQ ID NO: 67) | TIVLTPK (SEQ ID NO: 158) | 1641 |
| B-16/I-5 | STASYTR (SEQ ID NO: 68) | IPTPQPF (SEQ ID NO: 159) | 1632 |
| B-23 | ILGVLP (SEQ ID NO: 69) | GQSLSNT (SEQ ID NO: 160) | 1603 |
| B-13 | ATTVPAS (SEQ ID NO: 70) | DRMSVRT (SEQ ID NO: 161) | 1590 |
| I-9 | SMYGSYN (SEQ ID NO: 71) | YAGPYQH (SEQ ID NO: 162) | 1588 |
| I-25 | MNSGAVS (SEQ ID NO: 72) | AQSETAP (SEQ ID NO: 163) | 1588 |
| I-45 | WALDRGA (SEQ ID NO: 73) | LPLQKIS (SEQ ID NO: 164) | 1583 |
| B-29 | RPPALAP (SEQ ID NO: 74) | TEMPTFP (SEQ ID NO: 165) | 1580 |
| B-26 | SHPASHD (SEQ ID NO: 75) | SKSITAT (SEQ ID NO: 166) | 1553 |
| B-35 | TVAPSAN (SEQ ID NO: 76) | SGLTSGL (SEQ ID NO: 167) | 1549 |
| B-43 | ESRQVTP (SEQ ID NO: 77) | SWNTFLL (SEQ ID NO: 168) | 1513 |
| I-31/I-35 | TRAGLDF (SEQ ID NO: 78) | QHHAPLT (SEQ ID NO: 169) | 1496 |
| I-28 | SHSLLHH (SEQ ID NO: 79) | IQPDARD (SEQ ID NO: 170) | 1493 |

TABLE 1-continued

| | Top 92 peptides from initial screen including parasitic sequences | | Top 158 peptides from next-gen sequencing of phage from first round of biopanning | |
|---|---|---|---|---|
| Designation | Peptide Sequence | | Peptide Sequence | Copy # |
| I-44 | LAREPTS (SEQ ID NO: 80) | | AAQTSTP (SEQ ID NO: 171) | 1486 |
| I-48 | YHQTTIT (SEQ ID NO: 81) | | STSGRLP (SEQ ID NO: 172) | 1481 |
| B-3 | QHWFSPM (SEQ ID NO: 82) | | SNYNLPV (SEQ ID NO: 173) | 1473 |
| I-3 | QSNAQLE (SEQ ID NO: 83) | | NLPTVDT (SEQ ID NO: 174) | 1468 |
| B-33 | SHTTVNP (SEQ ID NO: 84) | | SYMAPMD (SEQ ID NO: 175) | 1450 |
| B-2 | STARAPT (SEQ ID NO: 85) | | GDHLPHQ (SEQ ID NO: 176) | 1449 |
| I-50 | GVQIMGR (SEQ ID NO: 86) | | LRHPSIP (SEQ ID NO: 177) | 1446 |
| B-48 | VSASALT (SEQ ID NO: 87) | | LPPGPLQ (SEQ ID NO: 178) | 1433 |
| I-18 | NDLPRRT (SEQ ID NO: 88) | | SPYSLYA (SEQ ID NO: 179) | 1422 |
| I-36 | ALMHGTS (SEQ ID NO: 89) | | ATPSWWA (SEQ ID NO: 180) | 1409 |
| B-18 | DPRATMY (SEQ ID NO: 90) | | YLPNGPR (SEQ ID NO: 181) | 1365 |
| B-14 | THSPSTH (SEQ ID NO: 91) | | YGDALFA (SEQ ID NO: 182) | 1336 |
| I-21 | DSGFPLP (SEQ ID NO: 92) | | SPQPFEE (SEQ ID NO: 183) | 1326 |
| B-36 | HLHYALP (SEQ ID NO: 93) | | GPQSGLQ (SEQ ID NO: 184) | 1320 |
| B-20 | EHQLNRA (SEQ ID NO: 94) | | LPLLDLN (SEQ ID NO: 185) | 1315 |
| I-39 | QLTIIPQ (SEQ ID NO: 95) | | GLPPYHS (SEQ ID NO: 186) | 1299 |
| B-4 | LPRNYPS (SEQ ID NO: 96) | | RPPALAP (SEQ ID NO: 187) | 1296 |
| | | | TNYAVNV (SEQ ID NO: 188) | 1295 |
| | | | SCTKHLC (SEQ ID NO: 189) | 1284 |
| | | | ANTLRSP (SEQ ID NO: 190) | 1270 |
| | | | SSFPPLL (SEQ ID NO: 191) | 1250 |
| | | | VIPHVLS (SEQ ID NO: 192) | 1240 |
| | | | TTQVPSF (SEQ ID NO: 193) | 1232 |
| | | | HSLAPTQ (SEQ ID NO: 194) | 1231 |
| | | | SHPASHD (SEQ ID NO: 195) | 1224 |
| | | | VSPPSSY (SEQ ID NO: 196) | 1215 |
| | | | HFRSGSL (SEQ ID NO: 197) | 1198 |
| | | | WTGSYRW (SEQ ID NO: 198) | 1182 |
| | | | QTSPHGK (SEQ ID NO: 199) | 1180 |
| | | | ATPQPLP (SEQ ID NO: 200) | 1173 |
| | | | SLTTLGS (SEQ ID NO: 201) | 1164 |
| | | | YSYPRDS (SEQ ID NO: 202) | 1147 |
| | | | ASFMPLQ (SEQ ID NO: 203) | 1145 |
| | | | GPSVRLQ (SEQ ID NO: 204) | 1138 |
| | | | LAHTLPL (SEQ ID NO: 205) | 1124 |
| | | | VQTPARM (SEQ ID NO: 206) | 1123 |
| | | | GLAPRSA (SEQ ID NO: 207) | 1116 |

TABLE 1-continued

| Top 92 peptides from initial screen including parasitic sequences | | Top 158 peptides from next-gen sequencing of phage from first round of biopanning | |
| --- | --- | --- | --- |
| Designation | Peptide Sequence | Peptide Sequence | Copy # |
| | | FPWSLDG (SEQ ID NO: 208) | 1104 |
| | | AHTSAIP (SEQ ID NO: 209) | 1082 |
| | | SHVPMNP (SEQ ID NO: 210) | 1078 |
| | | YMDSTRR (SEQ ID NO: 211) | 1077 |
| | | SSLVRTA (SEQ ID NO: 212) | 1077 |
| | | CWAMLRN (SEQ ID NO: 213) | 1076 |
| | | SKHHAPH (SEQ ID NO: 214) | 1065 |
| | | TSGTPQL (SEQ ID NO: 215) | 1059 |
| | | KQTLPSA (SEQ ID NO: 216) | 1058 |
| | | TQNEVRS (SEQ ID NO: 217) | 1041 |
| | | TFQYVST (SEQ ID NO: 218) | 1030 |
| | | HVVKMRG (SEQ ID NO: 219) | 1019 |
| | | TLHSLPP (SEQ ID NO: 220) | 1015 |
| | | ATLEMPP (SEQ ID NO: 221) | 1014 |
| | | QAHTIST (SEQ ID NO: 222) | 1012 |
| | | ALTPTPP (SEQ ID NO: 223) | 1005 |
| | | FVNPLSP (SEQ ID NO: 225) | 980 |
| | | KPAYPPH (SEQ ID NO: 226) | 978 |
| | | YPPHGVV (SEQ ID NO: 227) | 975 |
| | | SQPIENK (SEQ ID NO: 228) | 973 |
| | | TIEQHPP (SEQ ID NO: 229) | 971 |
| | | AGALHQF (SEQ ID NO: 230) | 969 |
| | | QHPAKTA (SEQ ID NO: 231) | 965 |
| | | ASPITKF (SEQ ID NO: 255) | 964 |
| | | ASTLKWA (SEQ ID NO: 232) | 962 |
| | | SSVWHST (SEQ ID NO: 233) | 955 |
| | | APALFPI (SEQ ID NO: 234) | 951 |
| | | GPHMWLV (SEQ ID NO: 235) | 949 |
| | | NHDYVTW (SEQ ID NO: 236) | 947 |
| | | SNRFEQQ (SEQ ID NO: 237) | 946 |
| | | TNSERIH (SEQ ID NO: 238) | 946 |
| | | AATLFPL (SEQ ID NO: 239) | 942 |
| | | SLLGQTP (SEQ ID NO: 240) | 936 |
| | | VPAWAGH (SEQ ID NO: 241) | 936 |
| | | TVAPSAN (SEQ ID NO: 242) | 930 |
| | | TTMPYIA (SEQ ID NO: 243) | 919 |
| | | NPPSRHP (SEQ ID NO: 244) | 919 |

TABLE 1-continued

| Top 92 peptides from initial screen including parasitic sequences | | Top 158 peptides from next-gen sequencing of phage from first round of biopanning | |
|---|---|---|---|
| Designation | Peptide Sequence | Peptide Sequence | Copy # |
| | | WAPWSPA (SEQ ID NO: 245) | 909 |
| | | TPQRDLR (SEQ ID NO: 246) | 900 |
| | | KFPMPQY (SEQ ID NO: 247) | 890 |
| | | SESTGTF (SEQ ID NO: 248) | 885 |
| | | LSMTGRD (SEQ ID NO: 249) | 880 |
| | | MTAAPVH (SEQ ID NO: 250) | 877 |
| | | ERAPMQS (SEQ ID NO: 251) | 872 |

Table 1 presents 250 peptide sequences obtained from phage clones recovered from the border zone of infarct after three rounds of in vivo biopanning (traditional phage screen) (92 clones) and peptide sequences obtained from next-gen sequencing (158 clones) of the phage pool amplified from the border region after the first round of biopanning minus the parasitic peptide sequences (in one embodiment, the peptide is not hornerin). Peptide sequences obtained from traditional screen were validated by FMT imaging for their specificity for post-infarct hearts. Rapid amplifiers or parasitic sequences were not removed from the initial screen list because many had nevertheless shown binding by FMT. In contrast, parasitic sequences were excluded from the next-gen list since the quantitative nature of next-gen sequence analysis weights these clones more heavily than warranted. The lists of parasitic sequences were obtained from previous studies that used the same phage display library. Three of the peptide sequences were seen in both the initial and next-gen analyses (in bold, italic font). * Indicates a phage clone sequence identified in an angiogenic screen of pancreatic cancer.

Pharmacodynamic Evidence of AZ7379 Drug Delivery Using Peptide-Targeted Liposomes.

To test the efficacy of targeted delivery of AZ7379 (FIG. 5), I-1 conjugated liposomes were prepared in 0.25 M ammonium sulfate solution for remote loading of AZ7379 using the reverse phase evaporation method (FIG. 10). Excess AZ7379 that was not loaded into the liposomes was removed by size exclusion chromatography. A sample of this liposome mixture was used to determine the final drug to lipid ratio using HPLC.

Figure 11A:
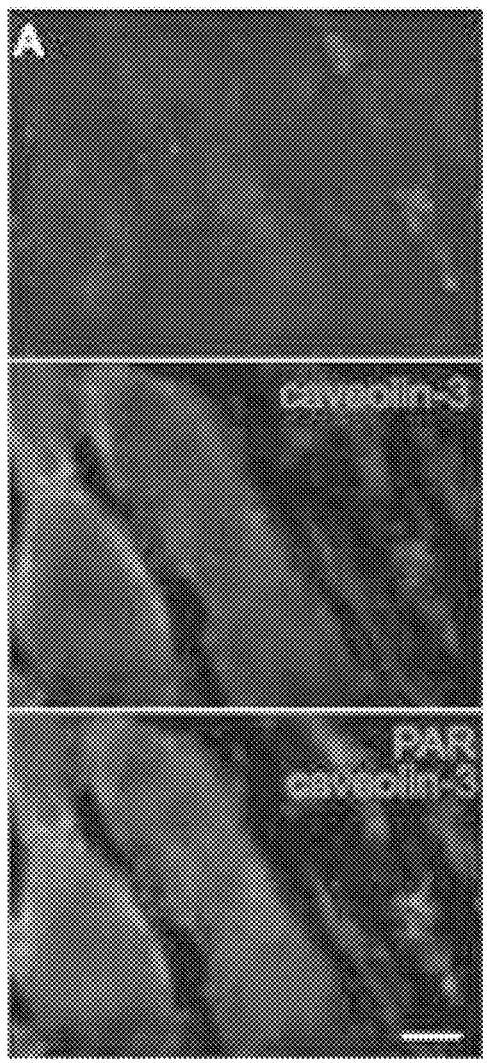
Figure 11B:
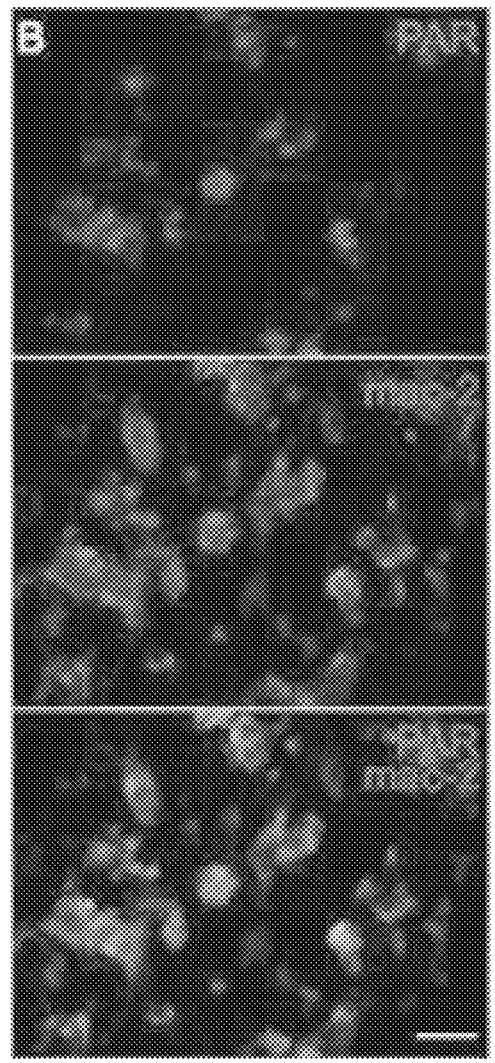
Figure 11C:
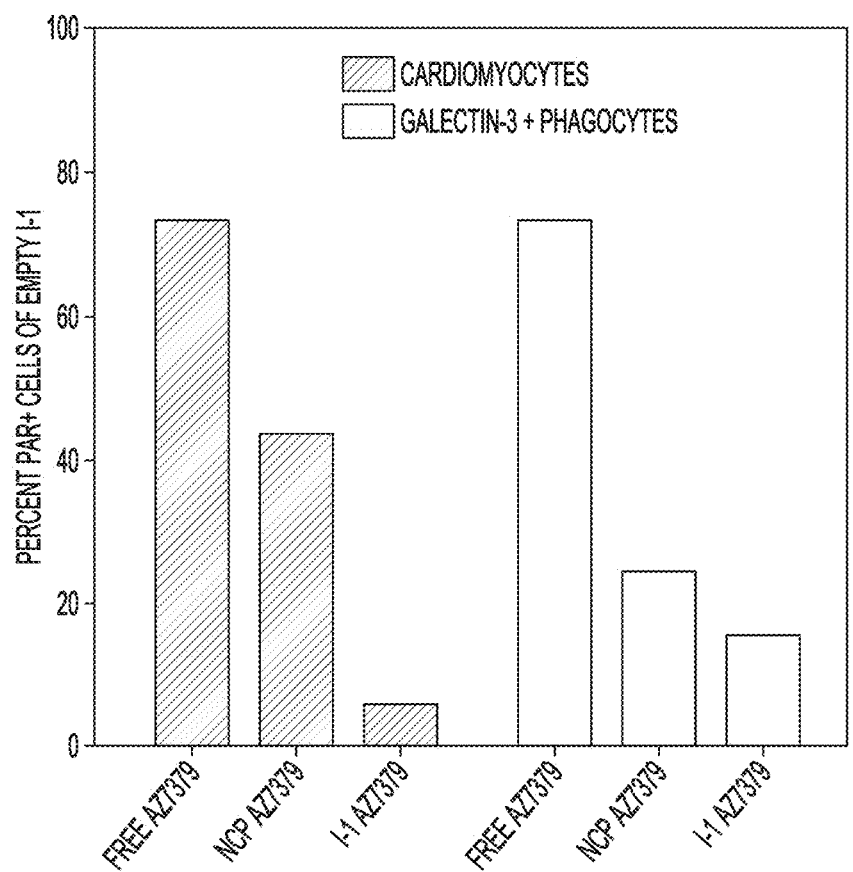
Figure 11D:
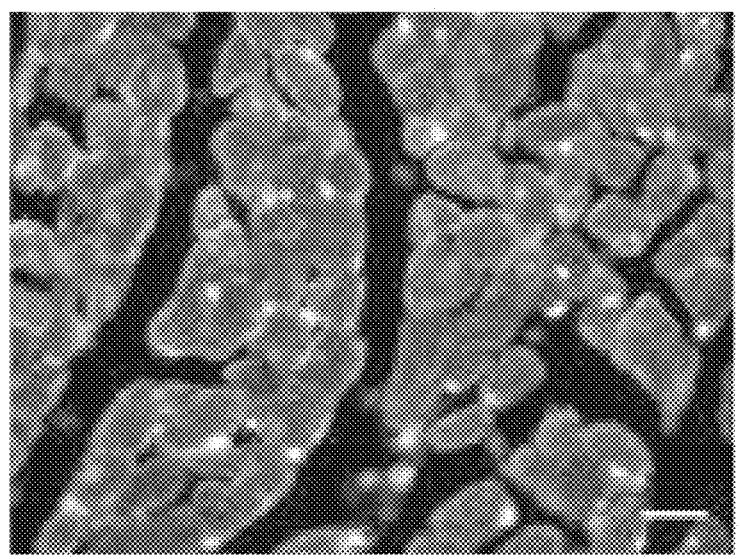

The size exclusion columns retained a small fraction of the liposomal lipid, but the final drug to lipid ratio could be estimated at 100-120 µg AZ7379 per mg of lipid. The drug loaded liposomes were characterized by Nanosight analysis for their size and concentration followed by structural analysis by TEM (FIG. 10B). Most of the I-1 liposomes with and without AZ7379 were spherical with a distinct lipid bilayer, but some liposomes exhibited an irregular structure which might be attributable to sample preparation for cryo TEM. The size of I-1 liposomes loaded with AZ7379 was also slightly larger than NCP liposomes (FIG. 5C). Prior to pursuing in vivo studies, release kinetics in 50% fetal bovine serum (FBS) were also determined in vitro from liposomes prepared with three types of phosphatidyl choline lipids. Liposomes formulated with DOPC were found to release AZ7379 somewhat more slowly than those formulated with DPPC or DSPC (FIG. 5D). For this reason, all subsequent experiments involving AZ7379 were conducted with DOPC liposomes. The presence of FBS in the liquid phase prevented the direct quantification of AZ7379 release, and thus represents an analytical limitation in these studies. Pharmacodynamic measurements were made after targeted delivery of AZ7379-loaded, I-1 targeted liposomes by measuring the percent of PAR+ nuclei in the infarct and border regions. Herein, PAR+ cells from mice injected with I-1 liposomes loaded with AZ7379 were compared with those injected with NCP liposomes loaded with AZ7379. In addition, mice injected with empty (i.e., drug-free) I-1 liposomes were included in the study as a relevant negative-control group (FIG. 6A). 29.6% PAR+ cells (20.2% phagocytes and 9.4% cardiomyocytes) were observed in empty I-1 liposome injected hearts and 21.7% PAR+ cells with free AZ7379 injected hearts (14.9% phagocytes and 6.8% cardiomyocytes). Free AZ7379 showed very little efficacy at 24 h post-injection as very little drug still remains in the mouse at the time. The comparison between free AZ7379 and the targeted liposomal formulation thus illustrates the delay in pharmacokinetics anticipated from liposomal delivery. Liposomes loaded with AZ7379, but targeted by the negative control peptide (NCP) had about 8.9% PAR+ cells (4.9% phagocytes and 4% cardiomyocytes), but AZ7379-loaded liposomes targeted with the I-1 peptide were effective in reducing that value to only 3.54% PAR+ cells (3.08% phagocytes and 0.46% cardiomyocytes) (FIG. 6E) [27]. When the PD of AZ7379-loaded, I-1 targeted liposomes was analyzed further, it was found that they were 9- and 1.5-fold more effective in reducing PAR in cardiomyocytes and macrophages, respectively, as compared with NCP liposomes (FIG. 11A). Thus the I-1 targeted drug delivery strategy was able to increase the availability of AZ7379 at the target site for an extended duration compared to free drug, and at the same time we was able to deliver more drug on target as compared to NCP liposomes. The cardiomyocyte specific peptide I-1 was also significantly more effective in reducing PAR production in cardiomyocytes as compared with NCP liposomes. Similar liposome-based therapeutic approaches could be implemented in the future to deliver cell type specific therapeutic molecules that might help improve cardiac function or reverse LV remodeling following a myocardial infarction.

Discussion

Coronary artery disease (CAD) imposes a tremendous toll, not only on the lives of individual patients, but also upon the healthcare systems of every nation in the western world [1-4]. The LV remodeling that occurs in response to MI is the major cause of heart failure and currently none of the available treatment strategies (short of cardiac transplant) are effective in preventing or reversing the LV remodeling process [28]. Recommended medical treatment options include beta-blockers, ACE inhibitors and angiotensin II receptor blockers (ARBs), but while these are effective in slowing the progression of heart failure, they cannot prevent it in cases of large or repeat MI. Further, the clinical utility of these mainline therapies is limited by their off-target effects at higher doses: chiefly hypotension [29-31]. This loss of blood pressure can be particularly problematic in patients with reduced cardiac function (such of those who have suffered an MI) and effectively place a "cap" on the doses that can be administered long-term (often for the life of the patient). It can therefore be argued that new therapeutic strategies are desperately needed to improve the ratio of on-target to off-target effects, not only for the existing pharmacopeia used to treat or prevent heart failure, but also for more novel strategies such as cardiac regeneration. Herein, in vivo biopanning with a phage display library was assessed by FMT and fluorescence microscopy to identify 7-mer peptides with specificity for cellular therapeutic targets of interest to regenerative medicine in the post-MI heart at 4 days post-reperfusion including endothelial cells, cardiomyocytes, myofibroblasts, c-Kit+ cells and extracellular matrix. Liposomes bearing these peptides as targeting ligands open the opportunity to deliver both conventional and novel drugs to specific cell types in the heart at specific time frames after the index event (MI). As the progression of LV remodeling after reperfused MI is a multi-step process involving a variety of different cell types [5], it follows that a platform technology such as the one described here will be needed to deliver the proper dose of drug, to the intended cellular target, at exactly the appropriate time during the evolution of LV remodeling post-MI. The work described herein was undertaken with the premise that such levels of precision control would ultimately be needed to implement rational design principles in the bioengineering of the LV remodeling process initiated by myocardial infarction.

With regard to local delivery to the post-infarct heart, it is noted that the current standard of care for treating acute MI is PCI [8]. PCI provides the opportunity to focus drug delivery not only on the heart, but also even on the region of the heart that suffered ischemia as a result of coronary thrombosis. One can therefore predict that this opportunity will be more fully exploited in the near future, as new drugs are developed to curtail reperfusion injury, inhibit apoptosis, or otherwise curtail the initial size of MI following reperfusion. Depending on the clinical scenario, it is conceivable that transcatheter delivery may suffice to "bioengineer" the function of neutrophils and perhaps even M1 macrophages in the early sub-acute phase post-MI, This, in part, provides rationale for our selection of 4 days post-MI as the timepoint for the phage display screen reported here, not only have most patients left the hospital by 4 days post-MI, this time marks the transition from acute inflammation to wound healing [32-34].

Liposomal formulations are increasingly used to deliver small molecules and there are now numerous formulations in clinical use [35]. Liposomes are ideal vehicles to deliver small molecules specifically to diseased tissue through ligand-mediated targeting [36]. These are modular synthetic constructs that accommodate a wide variety of customization. For example, the targeting peptides and drug payloads can easily be changed depending on the target cell and drug target of interest. Hydrophilic and/or lipophilic compartments of the liposomes can both be loaded with therapeutic molecules for targeted drug delivery [37]. The circulation time and drug release profiles of targeted liposomes can be fine-tuned as needed to optimize the therapeutic effect. For example, the external PEG brush and the composition of the lipid shell can be altered to adjust blood half-life or to control the kinetics of drug release, respectively.

In conclusion, the delivery of small molecule drugs via targeted liposomes has already impacted modern medicine and holds considerable potential for future applications, particularly in the field of regenerative medicine. Towards this end, liposomal formulations displaying the targeting peptides identified herein are useful in facilitating the delivery of therapeutic molecules to cell types of interest to regenerative medicine, providing for the right drug to be delivered to the right cell at the right time to redirect the wound healing process initiated by myocardial infarction, thus preventing heart failure through purposeful and methodical bioengineering of the LV remodeling process.

BIBLIOGRAPHY

1. S. Go, et al. Disease and Stroke Statistics-2013 Update A Report From the American Heart Association. Circulation. 127 (2013) e6-e245.
2. Seronde M F, et al. The Am. J. Medicine 127: 954-962 (2014).
3. Miura T and Mild T. Basic Res Cardiol. 103: 501-513 (2008).
4. Frangogiannis N G. Antioxidants and redox signaling. 8 (11&12): 1907-1939, (2006).
5. Frangogiannis N G. Nature Reviews Cardiol. 11: 255-265, (2014).
6. Xiang F, et al. European journal of heart failure 13: 254-263, (2011).
7. Stanton L W, et al. Circulation research 86: 939-945, (2000).
8. Frohlich G M, et al. Eur Heart J. 34: 1714-1722 (2013).
9. Miura T and Mild T. Basic Res Cardiol 103: 501-513 (2008).
10. Bornmann, C, et al. Cancer Chemother Pharmacol. 61:395-405, (2008).
11. A. Palfi, et al. J. Mol. Cell Cardiol. 41: 149-159, (2006)
12. Kristine O V, et al. PLoS one. 6: e20594-e20594, (2011).
13. Kelly K A, et al. PLoS Medicine 5: 657-668 (2008).
14. Hein J, Jensen J L, and Pedersen C N. PNAS 100: 14960-14965 (2003).
15. Francis S, Demetrios P. PNAS. 75: 4194-4198, (1978).
16. Dunn K W, et al. Am J Physiol Cell Physiol. 300: C723-C742, (2011).
17. Kelly K A, et al. PLoS Med. 5(4): e85 (2008).
18. Bausch D, et al. Clin Cancer Res. 17(2): 302-309 (2011).
19. Immordino M L, et al. Int J Nanomedicine 1(3): 297-315 (2006).
20. Koning G A, et al. J Lipo Res. 12: 107-119 (2002).
21. Mayer L D, et al. JPET 280: 1406-1414 (1997).
22. Nag O K and Awasthi V. Pharmaceutics 5:542-569 (2013).
23. Vuarchey C, et al. Nanotech Dev. 1(e2): 4-10 (2011).
24. Laverman P, et al. JPET 298: 607-612 (2001).
25. Ishida T, et al. J Controlled Release 105 (3): 305-317 (2005).
26. Naresh N K, et al. Monocyte and/or macrophage infiltration of heart after myocardial infarction: M R imaging by using T1-shortening liposomes 27. Moghimi S M, et al. Pharmacological reviews 53(2): 283-318 (2001).
28. French B A and Kramer C M. Drug Discov Today Dis Mech. 4(3): 185-196 (2007).
29. Frishman W H. Hypertension. 11 (3): 1121-1129 (1988).
30. Lama P J. Am J Ophthalmol. 134(5): 749-760 (2002).
31. Brown N J, Circulation. 97:1411-1420 (1998).
32. Weber K T, et al. Clin. Cardiol. 19: 447-455 (1996).
33. Frangogiannis N G, et al. Cardiovas. Res. 53: 31-47 (2002).
34. Nahrendorf M, et al. Circulation 121:2437-2445 (2010).
35. Allen T M and Cullis P R. Adv Drug Del Rev. 65: 36-48 (2013).
36. Torchilin V. Nature Rev. Drug Disc. 4: 145-160 (2005).
37. Cagdas M, et al. Liposomes as potential drug carrier systems for drug delivery. Chapter in Book-Nanotechnology and Nanomaterials: application of nanotechnology in drug delivery. Sezer AD (Ed), InTech (2014).

Example 2

Neovascularization in the Infarct Zone Post-MI can be Modulated Using Hornerin-Targeted Liposomes for Endothelial-Specific Delivery of VEGFR2 Inhibitor
Introduction Liposomes are an important class of drug delivery vehicles that have been studied since the mid-1960s [1]. Liposomes serve as effective particulate drug carriers as they improve pharmacokinetic (PK) and pharmacodynamic (PD) profiles of small molecule drugs [2]. In addition, remote loading methods can be used to improve the encapsulation efficiency, as in the example of Doxil: a liposomal formulation used in the setting of cancer [3-4]. With the recent FDA approval of Onivyde (liposomal irinotican) and the previous approvals of Doxil, Depocyte, Daunoxome, and Ambisome, the liposome field has reached clinical utility. However, all of these drug preparations are non-targeted and are for the treatment of cancer [5]. None of these formulations are actively targeted, but adding target-specific ligands to the surface of liposomes can further improve the therapeutic index of this new class of drugs [6]. The liposomal surface can readily be modified by adding a wide variety of targeting ligands including antibodies, antibody fragments and peptides that have affinity for cell types and tissue components of interest [6-8]. The targeting ligand provides for efficient accumulation of drugs in the tissue target of choice, thus reducing the drug exposure in non-target tissues.

Cardiovascular diseases impose a tremendous toll, not only on the lives of individual patients, but also upon the healthcare systems of every nation in the Western world. The clinical standard of care focuses on expediting the reperfusion of ischemic heart muscle, but even the prompt and successful reperfusion of occluded coronary arteries is often inadequate to prevent the death of heart muscle tissue. Myocardial infarction (MI) initiates a three-phase wound healing process: inflammation, proliferation and scar formation [9]. The inflammatory phase involves cytokine/chemokine signaling and the infiltration of neutrophils to clear necrotic cardiomyocytes and cellular debris from the infarct zone. This is followed by the proliferative phase that is initiated by monocytes that invade the infarct zone and differentiate into macrophages. During this phase, lasting 2-7 days post-MI in mice, neovessels are formed to support the proliferation of myofibroblasts in the infarct zone [10]. These myofibroblasts are responsible for the elaboration of collagen during the third phase, and the condensation of the collagen matrix produces the scar tissue characteristic of mature infarcts.

To facilitate the targeted delivery of small molecules to post-infarct heart, an in vivo phage display screen was carried out in a mouse model of cardiac ischemia/reperfusion injury [11]. One of the phage clones identified from this screen (B-40) was identical in sequence to a phage clone that was previously identified from a screen on pancreatic cancer endothelium (PTEM 9). Hornerin was identified as the molecular binding partner of PTEM 9, and its role in tumor progression is detailed in another manuscript that is currently under revision [12]. But in the setting of MI, it was found that the peak of hornerin expression in post-infarct hearts correlated with the peak of neovessel formation.

To study the effects of cell type-specific delivery of small molecule drugs in the context of LV remodeling after myocardial infarction (MI), the delivery of a VEGFR2 inhibitor (PTK787) using liposomes targeted by B-40 or I-1 peptides was studied. Peptide-targeted liposomes focus drug delivery on diseased tissue and minimize the off-target effects that result from systemic exposure. It was hypothesized that cell-type specific delivery would improve the therapeutic index of peptide-targeted liposomes relative to non-targeted liposomes or free drug, and thus might lower the amount of drug needed to achieve an equivalent therapeutic effect. The current report goes one step further than tissue-targeted delivery to determine if it were possible to target liposomes to one cell type or another within the same tissue by virtue of the peptide displayed on the liposome surface. More specifically, it was sought to determine whether the VEGFR2 inhibitor PTK787 could manifest differential effects in the infarct zone post-MI depending upon whether it was delivered via liposomes displaying cardiomyocyte-specific (I-1) or endothelial cell-specific (B-40) peptides. VEGFR2 belongs to VEGF family of tyrosine kinase receptors that is known to mediate almost all of the known cellular responses to VEGF and has been implicated in neovascularization of the infarct zone following reperfused MI [13-14].

Using PTK787-loaded, B-40 targeted liposomes, >10-fold lower ED50 value was observed as compared to free PTK787 in preventing neovessel formation following MI in mice. The systemic delivery of PTK787 at 100 mg/kg-d resulted in significant depression of neovascular formation as compared with control untreated animals (vessel volume fraction, VVF of 0.063 vs. 0.021). However, the B-40 liposomal formulation of PTK787 was also able to significantly depress neovessel formation at a dose of only 10 mg/kg-d (VVF of 0.063 vs. 0.008). Further, the ED50 of endothelial-targeted liposomes displaying the B-40 peptide was reduced by about 30% in comparison to cardiomyocyte-targeted liposomes displaying the I-1 peptide and carrying the same payload of PTK787 (6.2 vs. 8.8 mg/kg-d). And while the prevention of neovessel formation is not a therapeutic goal in the post-MI heart, these results provide proof-of-principle that B-40 targeted liposomes can deliver small molecule drugs 10-fold more efficiently than via systemic delivery, and that such delivery can significantly alter an anatomically and physiologically significant endpoint in vivo. These results will expedite novel therapeutic strategies such as the use of small molecules to program cardiac regeneration, where cell type-specific delivery of these agents is a prerequisite for obtaining effective results in the infarct border zone while minimizing deleterious off-target effects. Further, the results demonstrate that the concept of "off-target" can be extended to the cellular level, and that differential effects can be obtained by targeting one cell type versus another within the same tissue.

Materials and Methods

Lipids for Liposome Preparation 1,2-Dioleoyl-sn-glycerol-3-phosphocholine (DOPC), 1,2-dipalmitoyl-sn-glycerol-3-phosphocholine (DPPC), 1,2-disteroyl-sn-glycerol-3-phosphocholine (DSPC) cholesterol, 1,2-distearoyl-sn-glycero-3-phosphoethanolamine-N-[methoxy(polyethylene glycol)-2000 (DSPE-PEG$_{2000}$) and DSPE-PEG$_{3400}$-maleimide were purchased from Avanti Polar Lipids, Miami, Fla. 1,1'-Dioctadecyl-3,3,3'3'-tetramethylindotricarbocyanine iodide (DiR) was purchased from Invitrogen, Carlsbad, Calif. Peptides were synthesized using standard FMOC chemistry and Rink-Amide resin (Tufts University, Boston, Mass.).

FMT Imaging and Immunofluorescence in Heart Tissues

The B-40 phage clone was conjugated to the fluorophore VivoTag 680 (VT680) using the mono-reactive NHS ester of VT680 (PerkinElmer, Waltham, Mass.) for in vivo imaging by Fluorescence Molecular Tomography (FMT, PerkinElmer). Immunohistochemistry for border zone cells was performed using the following antibodies: rat anti-mouse CD31 (endothelial cell marker) at 1:250 dilution (BD Biosciences, San Jose, Calif.) and rabbit anti-hornerin at 1:200 (Sigma Aldrich, St. Louis, Mo.). Appropriate secondary antibodies were employed as needed to identify the primary antibodies:goat anti-rat Alexa Fluor 488 (1:250) (Abcam, Cambridge, Mass.) and goat anti-rabbit Alexa Fluor 488 (1:250) (Abcam, Cambridge, Mass.). For imaging functional vessels, lectin labeled with Alexa Fluor 647 (Life Technologies, Frederick, Md.) was injected iv into mice 10 min before euthanasia to stain the vessels.

Induction of Reperfused MI in Mice

Myocardial infarction was induced in male C57BL/6J mice (8-12 weeks old) by ligating the left anterior descending (LAD) artery for 40 minutes followed by reperfusion. Briefly, the mice were anesthetized with pentobarbital (100 µg/gram body weight), intubated, and mechanically ventilated with room air. The third and fourth ribs were cut to expose the heart and the pericardium was removed. The LAD was located and ligated with a 7-0 silk suture. The suture was removed at the end of 40 min occlusion to allow for reperfusion, thus simulating the clinical standard of care where reperfusion is typically achieved. The chest was then sutured closed in multiple layers and the mouse was recovered with inhaled oxygen.

Staining of Neovessels in the Infarct Region

On day 7 post-MI, 5 µg of lectin conjugated with Alexa Fluor 647 (AF 647) in saline was injected via tail vein and animals were euthanized 10 minutes after injection. The hearts were explanted, and 2 mm short axis sections were made so that neovessels could be imaged by confocal microscopy (Nikon Eclipse TE2000-E2, Nikon, Melville, N.Y., USA). Fifty µm-thick image stacks were acquired from both sides of the 2 mm section and 14 different regions were assessed per animal. The 50 µm-thick image stacks were used to determine various vessel parameters including the number of vessels, vessel diameter, vessel volume fraction (VVF) and vessel length density using RAVE software as previously reported [15].

Immunohistochemistry of Human Myocardium

Human heart tissue from 4 autopsy specimens were obtained from the BTRF (Biorepository Tissue Research Facility) at UVA. The heart tissue sections from the left ventricle included infarct, border and remote regions. The tissue sections were de-paraffinized by standard procedures and blocked with 1% fish skin gelatin in PBS for 3 h at room temperature. The primary antibodies (anti-hornerin (Sigma Aldrich) and rabbit IgG (Abcam) at 1:250 dilution) were incubated overnight at 40 C in 0.5% fish skin gelatin/PBS. The sections were washed 4 times with PBS followed by incubation with goat anti-rabbit HRP antibody at 1:250 dilution in 0.5% fish skin gelatin/PBS (Fisher Scientific) for 1 h at room temperature. Sections were again washed 4 times with PBS followed by 1 min incubation in DAB substrate. The tissues were later counter-stained with hematoxylin for 1 min followed by a rinse in running water for 3-5 min. Sections were immersed in bluing solution for 1 min followed by dehydration and sealing with mounting media and a glass cover slip.

Preparation of Peptide-Conjugated Liposomes

The 7-amino acid long NSP and B-40 peptides were synthesized with the following modifications on the C-terminus: 7-mer-GGSK(FAM)C as described previously [11]. Conjugation of the C-terminal Cys to DSPE-PEG3400-Maleimide (Avanti Polar Lipids, Miami, Fla.) was confirmed by mass spectrometry. Liposomes were prepared by hydration of lipid film prepared with 1,2-dioleoyl-sn-glycerol-3-phosphocholine (Avanti Polar Lipids) (DOPC):cholesterol:1,2-distearoyl-sn-glycero-3-phosphoethanolamine-N-[methoxy(polyethylene glycol)-2000 (DSPE-PEG2000): DiR:DSPE-PEG3400-peptide at 46:46:6:1:1 molar ratio (9.5, 4.5, 4.5, 1, and 0.5 mg, respectively) (FIG. 15A). 1,1'-Dioctadecyl-3,3,3'3'-tetramethylindotricarbocyanine iodide (DiR, Invitrogen, Carlsbad, Calif.) was incorporated into the lipid bilayer as a non-exchangeable fluorescent lipid dye that provided for FMT imaging of the peptide-conjugated liposomes in post-MI mice. The lipid film was hydrated with 1 ml of saline and the resulting lipid solution was extruded 41 times through a syringe extruder containing a 0.2 µm Nuclepore filter (GE Healthcare Bio-sciences, Pittsburgh, Pa.) [16].

Remote Loading of PTK787

For remote loading of PTK787, liposomes were prepared by reverse phase evaporation [17]. In brief, the lipid mixture was dissolved in 1 mL of chloroform and to this 3 mL of ethyl ether and 1 mL of 0.25 M ammonium sulfate solution was added. This lipid mixture was sonicated with a probe sonicator (XL2020, Misonix Inc, Farmingdale, N.Y.) to prepare a water-in-oil emulsion, from which organic solvents were removed under vacuum in a rotary evaporator. The volume of the resulting lipid slurry was then adjusted to 1 mL with water. Liposomes were prepared by passing through a 0.2 µm Nuclepore filter using a syringe extruder. Before remote loading, the ammonium sulfate present outside of the liposomes was removed by passing twice through size-exclusion, Zeba Spin desalting columns (Thermo Scientific, Rockford, Ill.). Zeba spin columns were washed three times with saline by spinning columns in a swinging bucket rotor at 1500×g for 1 min. One-half mg of PTK787 (5 mg/mL in saline) was then incubated with 5 mg of lipid (20 mg/mL) at 55° C. for 1 h. The free drug was removed by passing through Zeba spin columns that were washed with saline, and the drug to lipid ratio for the purified liposomes was determined by HPLC using a combination of spectrophotometric and evaporative light scattering detectors (see Supplementary methods).

Vessel Volume Fraction as a Measure of Pharmacodynamics

To determine the benefits of cell type-specific delivery over systemic delivery, an anatomical endpoint (vessel volume fraction) was compared after treating post-infarct mice with B-40 peptide-conjugated liposomes loaded with PTK787 vs. free PTK787. Six groups of animals were examined by morphometric analysis, including mice treated with: 1) Unloaded B-40 liposomes (3 injections over 7 days, n=5), 2) Free PTK787 (7 injections at 20 mg/kg-d, n=4), 3) Free PTK787 (7 injections at 100 mg/kg-d, n=4), 4) I-1 liposomes loaded with PTK787 (5 injections at 14 mg/kg over 7 days, mean of 10 mg/kg-d, n=4), 5) B-40 liposomes with PTK787 (5 injections of 14 mg/kg over 7 days, mean of 10 mg/kg-d, n=5), and 6) B-40 liposomes with PTK787 (3 injections of 14 mg/kg over 7 days, mean of 6 mg/kg-d, n=4). Ten min prior euthanasia on day 7, mice were injected with 10 µg of lectin AF 647 to stain functional vessels. The hearts were removed and cut along the short axis into four, 2 mm-thick sections. Using the last 2 sections from the apex, 50 µm image stacks were acquired by confocal microscopy from 14 different regions per animal (Nikon Eclipse TE2000-E2, Nikon, Melville, N.Y., USA). From these image stacks, infarct regions were segmented in Image J (NIH, Bethesda, Md.) for the determination of the vessel volume fraction (VVF) using RAVE software [18]. Vessel volume fraction (VVF) was reported as mean+/−standard error. Based on the VVF values from the various groups, Imax modeling was carried out to estimate ED50 values for each group. ED50 values were then used to assess the efficacy of B-40 liposome-mediated inhibition of neovessel formation.

Estimate of ED50 Values and Statistical Analysis

Imax modeling was applied to the VVR results, according to the equation:

$$E = \text{Baseline} \times \left(1 - \frac{I_{Max} \times Dose^n}{ED_{50}^n + Dose^n}\right)$$

Where the baseline was obtained from untreated animals, n is the Hill factor and ED50 is the dose needed to achieve an effect equal to 50% of its maximum effect. Imax was set to 1. All data where simultaneously modeled, whereas ED50 were estimated as separate parameters in the model. The Hill factor was estimated as a separate parameter for free drug PTK787 compared to the loaded-PTK787 and B-40 targeted liposomes, which were estimated as common parameter. Data was modeled using a Non-Linear Mixed Effects approach as implemented in Phoenix WinNonlin 6.4 and NLME 1.3 (Pharsight Certara, Princeton, N.J.). Interindividual variability was allowed for in baseline values and a power error model was applied (Observed (EObs=E+E^(0.5)×Residual, where Eobs is the observed response, E is the model predicted and Residual is the residual error estimate). To evaluate the model fit and its parameters, the input values were used to generate 1000 randomly-generated datasets by non-parametric bootstrap. The model was then fitted to these datasets and the model fits were used to derive the 5$^{th}$, 50$^{th}$ and 95$^{th}$ percentiles for the parameter estimates (Table 2) dose-response profiles (FIG. 16).

Statistical Analysis

All values in the text, tables and figures are expressed as mean±SEM. Statistical analyses were performed using Prism 5.0 (GraphPad software, La Jolla, Calif.). In the in vivo studies for determining vessel volume fraction, one-way ANOVA was performed followed by Tukey post t test to compare vessel volume fraction from different formulations of PTK787. A p value of p<0.05 was considered statistically significant.

Results

Hornerin expression in the endothelium of mouse and human infarcts.

In previous work, hornerin (Hrnr) was identified as the molecular binding partner of the B-40 peptide. Hrnr is a calcium binding protein and recently shown to be involved in cancers of the breast, kidneys and pancreas. In the post-MI setting, the expression of Hrnr was studied immediately after reperfusion by staining for Hrnr in heart sections. It was observed that Hrnr expression increases from day 2 to day 4 post-MI in mice and peaked by day 7 as seen in FIG. 12A. A 0.025 mm2 area was selected in the infarct and border zone to quantify the Hrnr expression using ImageJ software (FIG. 12B). Very low levels of Hrnr expression were observed in the remote region from day 2 to day 7 post-MI and with no clear trend of increase over the study period. The distribution of neovessels post-MI in the infarct/border zone and remote region was assessed by injecting lectin AF 647 via the tail vein 10 min before euthanizing the mice. Using confocal microscopy of 20 µm-thick heart sections, damaged vessels could be detected in the infarct region on day 2 post-MI (FIG. 12A). On day 4 post-MI, most of the damaged vessels had been cleared, and in some regions new, intact vessels began to appear. By day 7, neovessel formation was largely complete as needed to support the next phase of collagen deposition by myofibroblasts in the infarct region. In order to determine the clinical relevance of Hrnr expression after MI, human MI tissue from autopsy specimens (Biorepository Tissue Research Facility, UVa, Charlottesville) was stained with the same anti-Hrnr antibody, and strong Hrnr expression was observed in endothelial cells of the infarct/border zone (FIG. 12C), but was absent in the remote or healthy regions of the same hearts (FIG. 24).

Figure 13A:
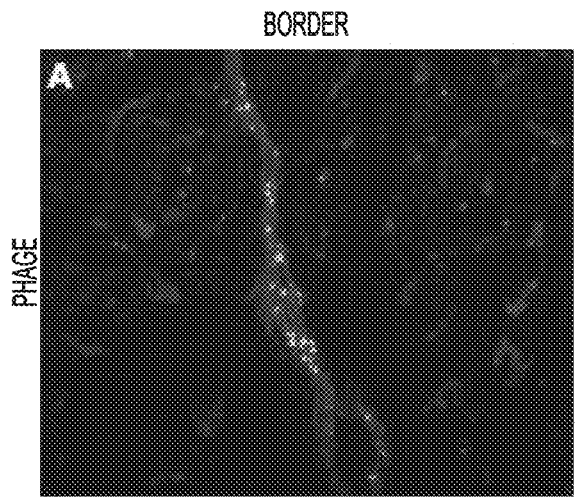
Figure 13B:
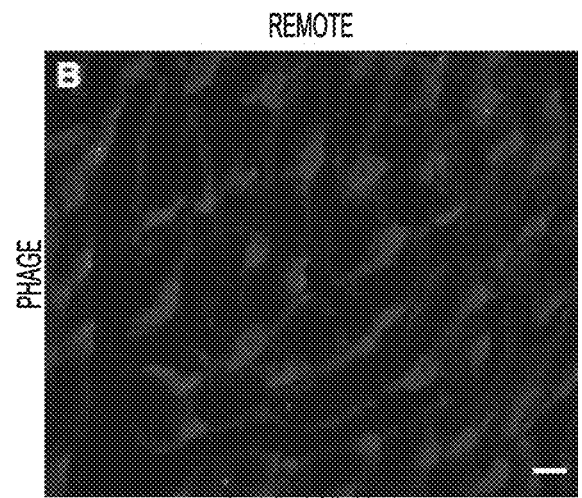
Figure 13C:
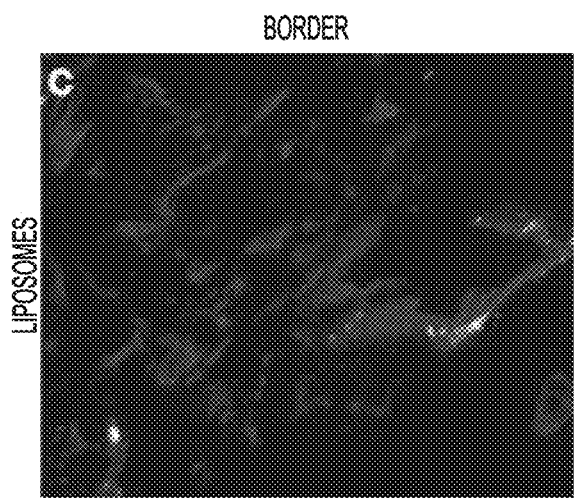
Figure 13D:
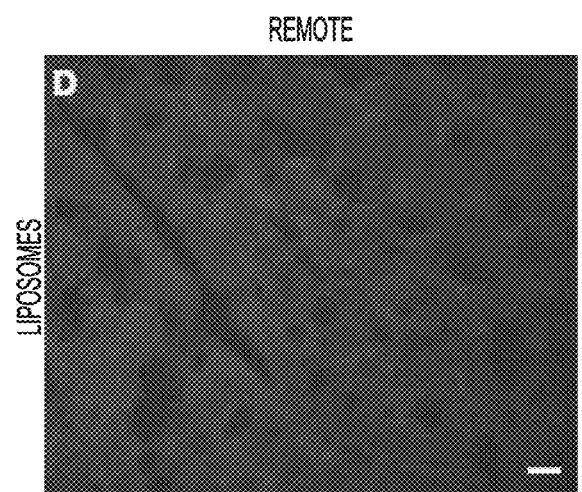

The distribution of B-40 phage and B-40 liposomes in post-MI mouse hearts was studied using in vivo FMT imaging followed by ex vivo tissue immunofluorescence in more than 20 animals using at least 5 different preparations of phage and liposomes. In accord with previous work [11], both the B-40 phage and liposomes were found tightly associated with border zone endothelium (FIGS. 13A&C). In contrast, B-40 phage and liposomes were essentially absent from the remote region (FIGS. 13B&D). Additional data pertaining to the biodistribution and specificity of B-40 liposomes for post-infarct hearts was previously reported, including a comparison with negative control peptide-conjugated liposomes showing that the accumulation of B-40 liposomes was at least 1.5 fold greater than negative control peptide liposomes [11].

Remote Loading of B-40 Liposomes with PTK787

PTK787 was used as a bioactive small molecule herein to demonstrate proof-of-principle for the efficacy of peptide targeting. PTK787 is a VEGFR2 inhibitor that has been widely used as anti-angiogenic therapy in treatment of cancer (FIG. 14A). And while neoangiogenesis is necessary to support scar formation after MI, the loss or prevention of neoangiogenesis as pharmacodynamic measurement was used herein. It was hypothesized that the deficit in neovessel formation could be easily quantified to support comparisons of targeted delivery vs. free-drug efficacy. PTK787 is a neutral small molecule with an IC50 of 37 nM in cell culture and 10 mg/mL solubility in water (FIG. 25). To examine the efficacy of targeted delivery of PTK787, B-40 conjugated liposomes was prepared in 0.25 M ammonium sulfate for remote loading (FIG. 14A) of PTK787 using the reverse phase evaporation method. PTK787 was dissolved in saline at 5 mg/mL and 50 µL was added to liposomes (100 µL of 20 mg/mL lipid) after removal of exterior ammonium sulfate by size exclusion chromatography.

Remote loading was carried out by incubating the mixture at 55° C. for 1 h or at room temperature for 4 h. Excess PTK787 not loaded into the liposomes was removed by size exclusion chromatography. A sample of this liposome mixture was used to determine the final drug to lipid ratio using HPLC. There was a small but negligible loss of lipid to the size exclusion columns, but the final drug to lipid ratio could be estimated at 100-130 μg PTK787 per mg of lipid for both B-40 and I-1 liposomes. The drug-loaded liposomes were further characterized by Nanosight analysis for their size and concentration followed by structural analysis by cryoTEM (FIG. 25). The concentration and size of liposomes at various stages of the remote loading process were characterized by Nanosight analysis (FIG. 14B). The analysis suggested that the size and concentration during various stages of remote loading was similar and that temperature and use of size exclusion columns did not affect the remote loading process. As assessed by cryoTEM, most of the B-40 liposomes (with or without PTK787) were spherical with a distinct lipid bilayer, although some were multilamellar and occasional liposomes exhibited an irregular structure that might be attributed to sample preparation for cryoTEM (FIG. 25).

Pharmacodynamic evidence of PTK787 delivery using B-40 peptide conjugated liposomes.

Figure 15A:
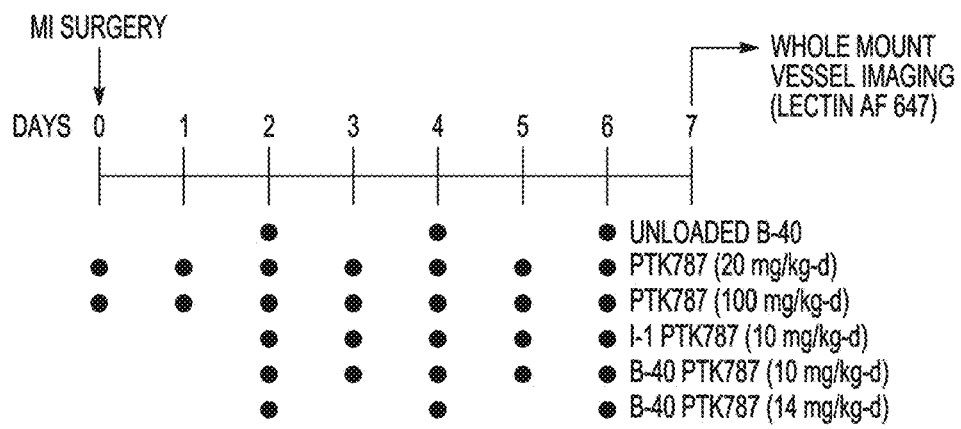
Figure 15B:
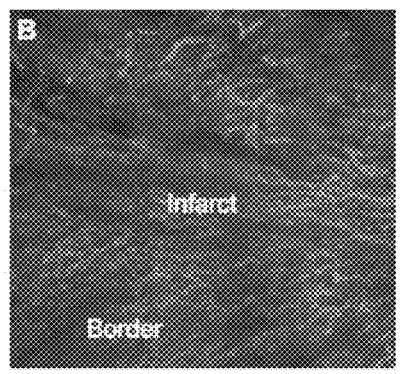
Figure 15C:
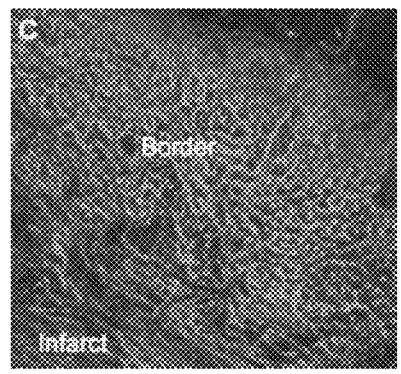
Figure 15D:
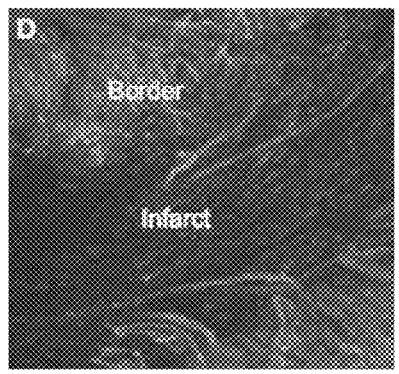
Figure 15E:
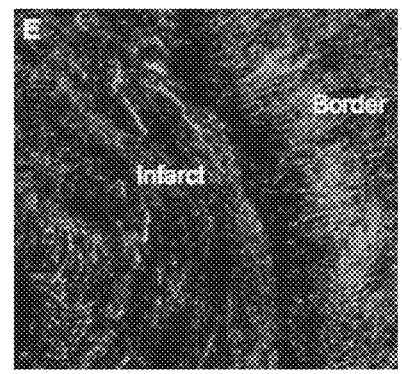
Figure 15F:
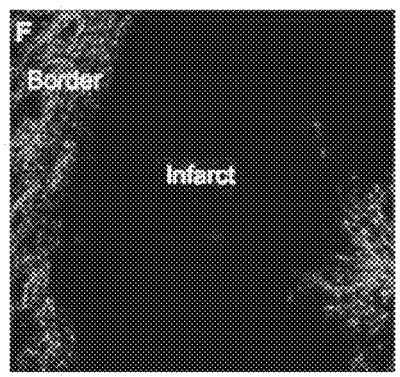
Figure 15G:
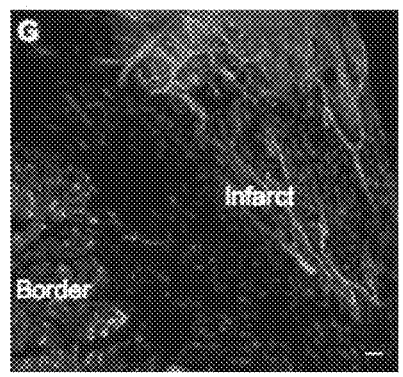

Of the 26 mice undergoing infarct surgery in the pharmacodynamic study, 23 survived until euthanasia for follow-up at the 7 day endpoint. Interestingly, the 3 mice that died unexpectedly all belonged to the study group receiving the highest dose of PTK787-loaded, B-40 targeted liposomes. Following tissue harvest on day 7 post-MI, vessel volume fraction (VVF) in the infarct region was used as a pharmacodynamic (PD) measurement of PTK787 efficacy. B-40 liposomes (specific for border zone endothelial cells) loaded with PTK787 were injected to deliver a mean of either 6 or 10 mg of PTK787 per kg-day (FIG. 15A). Neovessels present in the infarct zone on day 7 post-MI were quantified (as VVF) and compared with groups receiving free drug at two doses (20 and 100 mg/kg-d) delivered over the course of 7 days (day 0 to day 6 post-MI). This experiment also included a negative control group treated with unloaded (drug-free) B-40 liposomes and a group treated with I-1 liposomes (specific for cardiomyocytes) loaded with PTK787 (10 mg/kg-d). Representative heart tissue sections from each of these groups are presented in FIG. 15B-G, and the mean VVF results are plotted in FIG. 16A. A VVF of 0.063 was measured in untreated control hearts (unloaded B-40 liposomes), and VVF values decreased to 0.052 and 0.022 in the groups treated with free PTK787 at 20 and 100 mg/kg-d, respectively (i.e., these doses were 18 and 65 percent effective in reducing neovessel formation). Free PTK787 at 20 mg/kg-d showed only a modest effect in preventing neovessel formation in the infarct region. In contrast, B-40 liposomes loaded with PTK787 and administered at 10 mg/kg-d (VVF=0.008) were 88% effective in preventing neovessel formation while I-1 PTK787 at 10 mg/kg-d (VVF=0.022) was only 65% effective (FIG. 16A). When ED50 values were calculated (FIG. 16B) and compared, B-40 liposomes had a 10-fold lower ED50 than free PTK787 (6.2 vs. 63 mg/kg-d, respectively) and a 1.5 fold lower ED50 as compared with I-1 liposomes (8.8 mg/kg-d) (Table 2). Although I-1 liposomes were predominantly associated with border zone cardiomyocytes, it is speculated that some of the PTK787 may have been released locally, thus inhibiting VEGFR2 in nearby endothelial cells. The tight juxtaposition between capillaries and cardiomyocytes may thus have contributed to I-1 liposome mediated VEGFR2 inhibition in endothelial cells. Viewed in a broader context, the use of B-40 peptide liposomes to deliver pro-angiogenic small molecules to endothelial cells in the infarct border zone after MI may offer an attractive method to stimulate neovascularization in the remodeling infarct. This and other liposome-based therapeutic approaches could be implemented in the future for the cell-type specific delivery of therapeutic small molecules to improve cardiac function or favor cardiac regeneration after MI.

TABLE 2

Imax model fit derived ED50 values from vessel volume fraction for PTK alone, I-1 PTK787 and B-40 PTK787.

| Formulation | Estimated (ED50 (mg/kg-d) | Standard error | Median | $5^{th}$ % tile | $95^{th}$ % tile |
|---|---|---|---|---|---|
| PTX787 | 63 | 11 | 63 | 48 | 96 |
| I-1 PTK787 | 8.8 | 0.5 | 8.8 | 7.8 | 10 |
| B-40 PTK787 | 6.2 | 0.3 | 6.2 | 5.5 | 6.8 |

To further study hornerin, human umbilical vein endothelial cells (HUVECs) grown in cell culture were used. Different molecular weight protein isoforms of hornerin present in HUVECs were observed. The expression of hornerin in human microvascular endothelial cells from cardiac tissue (HMVECs) was compared and an absence of full-length hornerin in HMVECs was discovered (FIG. 34A). The cellular localization of the various hornerin isoforms was also studied and it was found that each of the cellular compartments including the cellular membrane harbored distinct hornerin isoforms (FIG. 34B). This was followed by immunofluorescence confirmation of hornerin localization in HUVECs using antibodies against two different regions of hornerin (FIG. 35).

Discussion

Coronary artery disease (CAD) is the leading cause of morbidity and mortality in developed countries. It is responsible for 1 in 5 deaths in the United States. About 38% of patients that experience a myocardial infarction (MI) will ultimately die from it [18-20]. Current drugs administered to patients after MI are focused primarily on delaying the progression of heart failure rather than on cardiac regeneration. However, the efficacy of these drugs (primarily ACE inhibitors and beta-blockers) is limited by systemic side effects (primarily hypotension) [21-24]. In order to develop a modular target-specific drug delivery platform, a phage display screen was previously carried out to identify novel peptides with specificity for the infarct border zone to enable the preferential delivery of small molecule drugs to cells of interest in the infarct border zone [11].

These peptides/phage clones were validated through sequential in vivo FMT imaging followed by a tissue immunofluorescence microscopy. The VT680 fluorophore that was conjugated to the phage clones for FMT imaging was subsequently used to identify the cellular targets of those clones by microscopy after counter-staining with antibodies against cell types of interest in the infarct. Interestingly, the B-40 phage clone was previously identified in an independent screen designed to identify pro-angiogenic targets in the setting of pancreatic cancer. That screen was carried out in mice bearing human pancreatic tumors with the goal of identifying angiogenic factors that were not VEGF mediated. The B-40 phage clone (B-40) appeared twice in the MI screen of approximately 100 clones [11], and the molecular binding partner was recently identified as Hrnr [12]. Hrnr belongs to the S100 family of calcium binding proteins and is known to be involved in wound healing and in breast cancer [25-27].

Herein, it was first sought to assess the time course of Hrnr expression during neovessel formation in the infarct and border zones after MI in mice. As shown in FIGS. 12A&B, the percentage of Hrnr+ vessels was found to steadily increase between days 2 and 7 post-MI in the border and infarct zones with very few Hrnr+ vessels (<0.2%) found in the remote region at any point in time. It was next sought to confirm the clinical relevance of Hrnr expression in human tissue, and found that Hrnr was highly expressed in endothelial cells located in the infarct border zone of hearts from patients with recent MI, but not in remote regions (FIG. 12C). Further studies of B-40 phage and liposomes confirmed that the B-40 peptide was specific for border zone endothelial cells, but not for endothelial cells in remote regions of hearts from mice with recent MI (FIG. 13).

In order to explore the therapeutic potential of B-40 targeted drug delivery, endothelial-(B-40) and cardiomyocyte-(I-1) targeted liposomes were then loaded with an established inhibitor of the VEGFR2 receptor (PTK787), and resulting liposomes were characterized by Nanosight and HPLC analysis (FIG. 14). The pharmacodynamic (PD) effects of these liposomal formulations were then compared with empty (drug-free) liposomes as well as with free drug administered at multiple doses in a mouse model of reperfused MI (FIG. 15). Quantitative morphometric analysis of these results using the RAVE software package [15] indicated that B-40 targeted liposomes loaded with PTK787 were significantly more effective in preventing neovessel formation than any other formulation tested, including free PTK787 delivered at a 10-fold higher dose (FIG. 16A). Imax modeling was then applied to calculate the ED50 values for each of the formulations examined (FIG. 16B), and confirmed that B-40 liposomes had a 10-fold lower ED50 than free PTK787, and a 33% fold lower ED50 as compared with I-1 targeted liposomes loaded with PTK787 (Table 2). It is therefore conclude that neovessel formation is significantly better inhibited by endothelial (B-40) targeted liposomes than by cardiomyocyte (I-1) targeted liposomes, and that both liposomal formulations are more effective than free drug (PTK787).

Conclusions

Herein it is demonstrated for the first time that the molecular targeting of a small-molecule drug (PTK787) to one cell population (endothelial) or another (cardiomyocyte) within a single tissue (heart) can have differential effects on an anatomical endpoint (neovascularization) depending upon the identity of the cell population that was targeted. The cell type-specific delivery of small molecule drugs demonstrated here opens the possibility of reaping therapeutic efficacy from compounds that would otherwise be contraindicated due to pleiotropic effects in different cell types within the same tissue. In other words, it is demonstrated herein, the ability to deliver one drug to one cell type and another drug to a different cell type even though those two cells are sitting side-by-side in the same tissue.

While the current study provides proof of principle, it also succeeds in demonstrating that the delivery of bioactive small molecules can have differential effects, here an increase in efficacy, depending upon the cell type that is targeted. Building upon this paradigm, one can administer small molecule drugs either together or in sequential fashion after myocardial infarction to curtail excess inflammatory responses and to optimize the heart's reparative response to MI through a rational bioengineering approach. Examples include stimulating the proliferation of border zone cardiomyocytes to replace necrotic regions of myocardium and/or reprogramming myofibroblasts to transdifferentiate into cardiomyocytes instead of elaborating collagenous scar tissue [9]. Ultimately, the cell type-specific drug delivery tools developed here will expedite efforts to modulate the heart's maladaptive response to MI by programming cardiac regeneration with non-invasive, systemically administered therapeutic agents delivered via targeted liposomes.

BIBLIOGRAPHY

1. Allen T M, and Cullis P R. Advanced Drug Del. Rev. 65: 36-48 (2013).
2. Ait-Oudhia A, et al. Pharmaceutics 6(1): 137-174 (2014).
3. Haran G, et al. Biochim Biophys Acta 1151:201-215 (1993).
4. Wu H C, and Chang D K. J Oncol. 723798 (2010).
5. Bozzuto G, and Molinari A. Int J Nanomed. 10: 975-999 (2015).
6. Chang D, et al. PLoS ONE 8(12): e83239 (2013).
7. Nogueira E, et al. Colloids and Surfaces B: Biointerfaces 136: 514-526 (2015).
8. Wnuk M, et al. Am. J. Pathol. 178(4): 1899-1912, (2011).
9. Frangogiannis N G. Antioxidants and redox signaling. 8 (11&12): 1907-1939, (2006).
10. Frangogiannis N G. Nature Reviews Cardiol. 11: 255-265, (2014).
11. Dasa S, et al. J. Control. Release 220: 556-567 (2015).
12. Seaman M E, et al. Nat Comm (revision).
13. Vandervelde S, et al. Cardiovasc. Pathol. 15 (2): 83-90, (2006).
14. Yang Z, et al. Clinica Chimica Acta. 381 (2): 114-118, (2007).
15. Seaman, M. E., et al. PLoS One 6, e20807 (2011).
16. Immordino M L, et al. Int J Nanomedicine 1(3): 297-315 (2006).
17. Francis S, Demetrios P. PNAS. 75: 4194-4198, (1978).
18. Mozaffarian D, et al. Circulation. 131: e29-e322 (2015).
19. Seronde M F, et al. The Am. J. Medicine 127: 954-962 (2014).
20. Miura T and Mild T. Basic Res Cardiol. 103: 501-513 (2008).
21. French B A and Kramer C M. Drug Discov Today Dis Mech. 4(3): 185-196 (2007).
22. Frishman W H. Hypertension. 11 (3): 1121-1129 (1988).
23. Lama P J. Am J Ophthalmol. 134(5): 749-760 (2002).
24. Brown N J, Vaughan D E. Circulation. 97:1411-1420 (1998).
25. Makino, T., et al. J Histochem Cytochem 51, 485-492 (2003).
26. Takaishi, M., et al. J Biol Chem 280, 4696-4703 (2005).
27. Rhode D, et al. J. Cardiovasc. Transl. Res. 3(5): 525-537, (2010).

Example 3

PAR immunofluorescence (IF) in heart sections from DIO mice suggested the presence of PAR in the endothelial cells (CD31), fibroblasts (DDR2) and macrophages (mac-2). But the majority (80-90%) of PAR was seen in the endothelial cells and only about 10% PAR seen in macrophages and fibroblasts.

The conjugation of CRPPR to PEG-DSPE was carried out as described in Zhang H et al. in Biomaterials, 29:1976-1988 (2008). The CRPPR-peptide mediates a 47-fold targeting to the heart via binding to CRIP-2 in the myocardium as well as endothelium. Given that the molecular target is known and expressed in healthy hearts, this allows for binding studies of liposomes in vitro and use of healthy mice for efficacy studies in vivo, respectively. While the testing of CRPPR liposomes in DIO animals was not carried out, VCAM-1 binding liposomes were carried out in DIO mice and a greater association to DIO hearts was observed compared to MI specific liposomes.

As an alternative, an in vivo phage display was carried out to identify peptides specific for DIO hearts and later identify peptides specific for endothelial cells. Phage screen was carried out in 2 healthy and DIO animals and peptides sequences determined using NGS method. A number of promising lead peptides was identified for the DIO heart. Cardiac specificity can be assessed by FMT using ratiometric imaging (as used previously in the MI screen).

With the goal of demonstrating that targeted delivery offers advantage(s) over free AZ7379, efficacious doses of free AZ7379 needed to prevent PAR formation was identified. A single dose of 5 µmol/kg was not effective in reducing PAR formation as seen after 1 and 24 h oral gavage. But a dose of 25 µmol/kg was effective in reducing PAR formation at 24 h and not 1 h after oral gavage.

All publications, patents, and patent applications, Genbank sequences, websites and other published materials referred to throughout the disclosure herein are herein incorporated by reference to the same extent as if each individual publication, patent, or patent application, Genbank sequences, websites and other published materials was specifically and individually indicated to be incorporated by reference. In the event that the definition of a term incorporated by reference conflicts with a term defined herein, this specification shall control.

What is claimed is:

1. An isolated peptide selected from the group consisting of:

| | | |
|---|---|---|
| B-29 | RPPALAP | (SEQ ID NO: 6) |
| B-43 | ESRQVTP | (SEQ ID NO: 8) |
| B-18 | DPRATMY | (SEQ ID NO: 9) |
| B-22/B-40* | SLLNRMP | (SEQ ID NO: 10) |
| B-11 | TMQHDG | (SEQ ID NO: 14) |
| B-17 | YATQSSP | (SEQ ID NO: 17) |
| B-42 | AMRPPLN | (SEQ ID NO: 31) |
| B-47 | ATMSRAP | (SEQ ID NO: 35) |
| B-49 | TPGGKSP | (SEQ ID NO: 36) |
| B-50 | GLSQLQR | (SEQ ID NO: 38) |
| B-6 | YPNHASP | (SEQ ID NO: 39) |
| B-7 | SDTWSSR | (SEQ ID NO: 40) |
| B-8 | TLAQIHH | (SEQ ID NO: 41) |
| I-1 | TALPRLN | (SEQ ID NO: 42) |
| I-12 | SALPNLY | (SEQ ID NO: 45) |
| I-8 | TSLSDSQ | (SEQ ID NO: 65) | wherein said isolated peptide is conjugated to a delivery vehicle containing a payload, wherein said delivery vehicle is a liposome, micelle, non-liposomal nanoparticle, nanoparticle made of drug, microbubble, dendrimer, adeno-associated virus (AAV) vector, or nanoparticle of polymer, metal oxide and/or lipid, wherein said payload is a therapeutic agent or a diagnostic agent, wherein said therapeutic agent is a small molecule, protein, peptide, cytokine, nucleic acid, hormone, steroid, enzyme, or mixtures thereof.

2. The isolated peptide of claim 1, wherein one or more of the amino acids are D-amino acids.

3. The isolated peptide of claim 1, wherein the delivery vehicle is a liposome.

4. The isolated peptide of claim 1, wherein the isolated peptide is associated non-covalently with the delivery vehicle.

5. A composition comprising one or more of the isolated peptides of claim 1 and a pharmaceutically acceptable carrier.

6. A method of delivering a payload to cardiovascular tissue or cell of a subject in need thereof comprising administering to the subject an isolated peptide selected from the group consisting of:

| | | |
|---|---|---|
| B-29 | RPPALAP | (SEQ ID NO: 6) |
| B-26 | SHPASHD | (SEQ ID NO: 7) |
| B-43 | ESRQVTP | (SEQ ID NO: 8) |
| B-18 | DPRATMY | (SEQ ID NO: 9) |
| B-22/B-40* | SLLNRMP | (SEQ ID NO: 10) |
| B-11 | TMQHDG | (SEQ ID NO: 14) |
| B-12 | SAPGSSP | (SEQ ID NO: 15) |
| B-17 | YATQSSP | (SEQ ID NO: 17) |
| B-42 | AMRPPLN | (SEQ ID NO: 31) |
| B-47 | ATMSRAP | (SEQ ID NO: 35) |
| B-49 | TPGGKSP | (SEQ ID NO: 36) |
| B-50 | GLSQLQR | (SEQ ID NO: 38) |
| B-6 | YPNHASP | (SEQ ID NO: 39) |
| B-7 | SDTWSSR | (SEQ ID NO: 40) |
| B-8 | TLAQIHH | (SEQ ID NO: 41) |
| I-1 | TALPRLN | (SEQ ID NO: 42) |
| I-12 | SALPNLY | (SEQ ID NO: 45) |
| I-8 | TSLSDSQ | (SEQ ID NO: 65) | wherein said isolated peptide is conjugated to a payload or a delivery vehicle containing a payload, wherein said payload is a therapeutic agent or a diagnostic agent, wherein said therapeutic agent is a small molecule, protein, peptide, cytokine, nucleic acid, hormone, steroid, enzyme or mixtures thereof, wherein the isolated peptide targets the payload to the cardiovascular tissue or cell thereby delivering the payload to the cardiovascular tissue or cell.

7. The method of claim 6, wherein the administration is systemic or subcutaneous.

8. The method of claim 6, wherein the isolated peptide is selective for a dysfunctional, ischemic and/or peri-infarct region of mammalian cardiovascular tissue.

9. A method of treating a cardiomyopathy in a subject comprising:

administering systemically to a subject in need thereof an effective amount of an isolated peptide selected from the group consisting of:

| | | |
|---|---|---|
| B-29 | RPPALAP | (SEQ ID NO: 6) |
| B-26 | SHPASHD | (SEQ ID NO: 7) |
| B-43 | ESRQVTP | (SEQ ID NO: 8) |
| B-18 | DPRATMY | (SEQ ID NO: 9) |
| B-22/B-40* | SLLNRMP | (SEQ ID NO: 10) |
| B-11 | TMQHDG | (SEQ ID NO: 14) |
| B-12 | SAPGSSP | (SEQ ID NO: 15) |
| B-17 | YATQSSP | (SEQ ID NO: 17) |
| B-42 | AMRPPLN | (SEQ ID NO: 31) |
| B-47 | ATMSRAP | (SEQ ID NO: 35) |
| B-49 | TPGGKSP | (SEQ ID NO: 36) |
| B-50 | GLSQLQR | (SEQ ID NO: 38) |
| B-6 | YPNHASP | (SEQ ID NO: 39) |
| B-7 | SDTWSSR | (SEQ ID NO: 40) |

| | |
|---|---|
| B-8 | TLAQIHH (SEQ ID NO: 41) |
| I-1 | TALPRLN (SEQ ID NO: 42) |
| I-12 | SALPNLY (SEQ ID NO: 45) |
| I-8 | TSLSDSQ (SEQ ID NO: 65) | wherein said isolated peptide is conjugated to a payload or a delivery vehicle containing a payload, wherein said payload is a therapeutic agent, wherein said therapeutic agent is a small molecule, protein, peptide, cytokine, nucleic acid, hormone, steroid, enzyme or mixtures thereof, wherein the effective amount is effective to cause functional improvement in at least one of the following parameters: left ventricular strain, left ventricular volume, left ventricular area, left ventricular dimension, cardiac function or 6-minute walk test.

10. A method of delivering a payload to a cardiovascular cell comprising contacting said cell with an isolated peptide selected from the group consisting of:

| | |
|---|---|
| B-29 | RPPALAP (SEQ ID NO: 6) |
| B-26 | SHPASHD (SEQ ID NO: 7) |
| B-43 | ESRQVTP (SEQ ID NO: 8) |
| B-18 | DPRATMY (SEQ ID NO: 9) |
| B-22/B-40* | SLLNRMP (SEQ ID NO: 10) |
| B-11 | TMQHDG (SEQ ID NO: 14) |
| B-12 | SAPGSSP (SEQ ID NO: 15) |
| B-17 | YATQSSP (SEQ ID NO: 17) |
| B-42 | AMRPPLN (SEQ ID NO: 31) |
| B-47 | ATMSRAP (SEQ ID NO: 35) |
| B-49 | TPGGKSP (SEQ ID NO: 36) |
| B-50 | GLSQLQR (SEQ ID NO: 38) |
| B-6 | YPNHASP (SEQ ID NO: 39) |
| B-7 | SDTWSSR (SEQ ID NO: 40) |
| B-8 | TLAQIHH (SEQ ID NO: 41) |
| I-1 | TALPRLN (SEQ ID NO: 42) |
| I-12 | SALPNLY (SEQ ID NO: 45) |
| I-8 | TSLSDSQ (SEQ ID NO: 65) | wherein said isolated peptide is conjugated to a payload or a delivery vehicle containing a payload, wherein said payload is a therapeutic agent or a diagnostic agent, wherein said therapeutic agent is a small molecule, protein, peptide, cytokine, nucleic acid, hormone, steroid, enzyme or mixtures thereof.

11. A method of treating a cardiovascular disease or disorder comprising administering to a subject in need thereof an effective amount of an isolated peptide selected from the group consisting of:

| | |
|---|---|
| B-29 | RPPALAP (SEQ ID NO: 6) |
| B-26 | SHPASHD (SEQ ID NO: 7) |
| B-43 | ESRQVTP (SEQ ID NO: 8) |
| B-18 | DPRATMY (SEQ ID NO: 9) |
| B-22/B-40* | SLLNRMP (SEQ ID NO:10) |
| B-11 | TMQHDG (SEQ ID NO: 14) |
| B-12 | SAPGSSP (SEQ ID NO: 15) |
| B-17 | YATQSSP (SEQ ID NO: 17) |
| B-42 | AMRPPLN (SEQ ID NO: 31) |
| B-47 | ATMSRAP (SEQ ID NO: 35) |
| B-49 | TPGGKSP (SEQ ID NO: 36) |
| B-50 | GLSQLQR (SEQ ID NO: 38) |
| B-6 | YPNHASP (SEQ ID NO: 39) |
| B-7 | SDTWSSR (SEQ ID NO: 40) |
| B-8 | TLAQIHH (SEQ ID NO: 41) |
| I-1 | TALPRLN (SEQ ID NO: 42) |
| I-12 | SALPNLY (SEQ ID NO: 45) |
| I-8 | TSLSDSQ (SEQ ID NO: 65) | wherein said isolated peptide is conjugated to a payload or a delivery vehicle containing a payload, wherein said payload is a therapeutic agent, wherein said therapeutic agent is a small molecule, protein, peptide, cytokine, nucleic acid, hormone, steroid, enzyme or mixtures thereof, wherein the effective amount treats the disease or disorder.

12. The method of claim 6 wherein two or more isolated peptides having different amino acid sequences are administered.

13. The method of claim 6, wherein two or more isolated peptides comprising two or more different payloads are administered.

14. The method of claim 13, wherein the two or more different payloads are therapeutic agents and imaging agents.

15. The method of claim 13, wherein each payload is delivered to a different cell type.

16. The method of claim 15, wherein the different cell types are located within the same tissue.

17. An isolated peptide selected from the group consisting of:

| | |
|---|---|
| B-29 | RPPALAP (SEQ ID NO: 6) |
| B-26 | SHPASHD (SEQ ID NO: 7) |
| B-43 | ESRQVTP (SEQ ID NO: 8) |
| B-18 | DPRATMY (SEQ ID NO: 9) |
| B-22/B-40* | SLLNRMP (SEQ ID NO: 10) |
| B-11 | TMQHDG (SEQ ID NO: 14) |
| B-12 | SAPGSSP (SEQ ID NO: 15) |

-continued

| | | |
|---|---|---|
| B-17 | YATQSSP | (SEQ ID NO: 17) |
| B-42 | AMRPPLN | (SEQ ID NO: 31) |
| B-47 | ATMSRAP | (SEQ ID NO: 35) |
| B-49 | TPGGKSP | (SEQ ID NO: 36) |
| B-50 | GLSQLQR | (SEQ ID NO: 38) |
| B-6  | YPNHASP | (SEQ ID NO: 39) |
| B-7  | SDTWSSR | (SEQ ID NO: 40) |
| B-8  | TLAQIHH | (SEQ ID NO: 41) |
| I-1  | TALPRLN | (SEQ ID NO: 42) |
| I-12 | SALPNLY | (SEQ ID NO: 45) |
| I-8  | TSLSDSQ | (SEQ ID NO: 65) | wherein said isolated peptide is conjugated to a payload, wherein said payload is a diagnostic agent, wherein said diagnostic agent is a rare earth metal, a radioisotope, a radionuclide or a contrast agent.

18. The isolated peptide of claim 17, wherein the payload is conjugated to the isolated peptide indirectly.

19. The isolated peptide of claim 17 wherein the payload is conjugated to the isolated peptide with one or more linkers and/or spacers.

* * * * *